US006114506A

United States Patent [19]
Reed et al.

[11] Patent Number: 6,114,506
[45] Date of Patent: Sep. 5, 2000

[54] COMPOSITION AND METHOD FOR ENHANCING FIBRINOLYSIS

[75] Inventors: Guy L. Reed, Winchester, Mass.; Linda Harris, Seattle; Jurgen Bajorath, Lynnwood, both of Wash.; Gary Matsueda, Princeton, N.J.; Mei-Yin Hsu, Hillsboro, N.J.; Jiri Novotny, Princeton, N.J.

[73] Assignees: General Hospital Corporation, Boston; President and Fellows of Harvard College, Cambridge, both of Mass.; Bristol-Myers Squibb Company, Princeton, N.J.

[21] Appl. No.: 08/933,983

[22] Filed: Sep. 19, 1997

Related U.S. Application Data
[60] Provisional application No. 60/026,356, Sep. 20, 1996.

[51] Int. Cl.$^7$ .................................................... C07K 16/00
[52] U.S. Cl. .................................... 530/387.3; 530/388.1; 424/130.1; 424/133.1; 424/145.1
[58] Field of Search .......................... 530/388.1, 387.3; 424/130.1, 133.1, 145.1

[56] References Cited

U.S. PATENT DOCUMENTS

| | | | |
|---|---|---|---|
| 4,147,765 | 4/1979 | Stephan et al. | 424/12 |
| 4,198,335 | 4/1980 | Collen | 260/112 |
| 4,245,040 | 1/1981 | Pigeram | 435/13 |
| 4,273,873 | 6/1981 | Sugitachi et al. | 435/180 |
| 4,346,029 | 8/1982 | Collen | 260/112 |
| 4,368,149 | 1/1983 | Masuho et al. | 260/112 |
| 4,414,148 | 11/1983 | Jansen et al. | 260/112 |
| 4,421,735 | 12/1983 | Haber et al. | 424/1.1 |
| 4,455,290 | 6/1984 | Olexa et al. | 424/1.1 |
| 4,470,925 | 9/1984 | Auditore-Hargreaves | 260/112 |
| 4,474,893 | 10/1984 | Reading | 436/547 |
| 4,545,988 | 10/1985 | Nakayama et al. | 424/94.63 |
| 4,671,958 | 6/1987 | Rodwell et al. | 424/1.53 |
| 4,673,573 | 6/1987 | Ferres et al. | 424/94.63 |
| 4,722,903 | 2/1988 | Kudryk et al. | 435/7.93 |
| 4,758,524 | 7/1988 | Bundesen et al. | 435/7.92 |
| 4,833,085 | 5/1989 | Schaumann et al. | 530/388.26 |
| 4,916,070 | 4/1990 | Matsueda et al. | 530/387.9 |
| 4,927,916 | 5/1990 | Matsueda et al. | 435/70.21 |
| 5,116,613 | 5/1992 | Haber et al. | 424/178.1 |
| 5,372,812 | 12/1994 | Reed et al. | 424/145.1 |
| 5,582,862 | 12/1996 | Reed et al. | 424/145.1 |
| 5,585,089 | 12/1996 | Queen et al. | 424/133.1 |

FOREIGN PATENT DOCUMENTS

| | | |
|---|---|---|
| 572125 | 9/1984 | Australia . |
| 0 063 002 A2 | 10/1982 | European Pat. Off. . |
| 0 088 994 A2 | 9/1983 | European Pat. Off. . |
| 0 120 694 A2 | 10/1984 | European Pat. Off. . |
| 0 125 023 A1 | 11/1984 | European Pat. Off. . |
| 0 142 905 A2 | 5/1985 | European Pat. Off. . |
| 0 146 050 A2 | 6/1985 | European Pat. Off. . |
| 0 159 025 A2 | 10/1985 | European Pat. Off. . |
| 0 187 658 A2 | 7/1986 | European Pat. Off. . |
| 0 271 227 A2 | 6/1988 | European Pat. Off. . |
| 0 336 693 | 10/1989 | European Pat. Off. . |
| 61-268630 | 11/1986 | Japan . |
| WO 83/03678 | 10/1983 | WIPO . |
| WO 83/03679 | 10/1983 | WIPO . |
| WO 83/03971 | 11/1983 | WIPO . |
| WO 85/00974 | 3/1985 | WIPO . |
| WO 86/01533 | 3/1986 | WIPO . |
| WO 87/05934 | 10/1987 | WIPO . |
| WO 87/06263 | 10/1987 | WIPO . |
| WO 87/06836 | 11/1987 | WIPO . |
| WO 88/01649 | 3/1988 | WIPO . |
| WO 88/03559 | 5/1988 | WIPO . |
| WO 89/09817 | 10/1989 | WIPO . |
| 91/09967 | 11/1991 | WIPO . |

OTHER PUBLICATIONS

Butte, A.N. et al., "$\alpha_2$–Antiplasmin Causes Thrombi to Resist Fibrinolysis Induced by Tissue Plasminogen Activator in Experimental Pulmonary Embolism," *Circulation* 95:1886–1891 (Apr. 1997).

Jones, P.T. et al., "Replacing the complementarity–determining regions in a human antibody with those from a mouse," *Nature* 321:522–525 (1986).

Reed, G.L., "Functional Characterization of Monoclonal Antibody Inhibitors of $\alpha$2–Antiplasmin that Accelerate Fibrinolysis in Different Animal Plasmas," *Hybridoma* 16:281–286 (Jun. 1997).

Reed, G.L., "Monoclonal Antibodies: 77 (anti $\alpha$22 antiplasmin)," *Hybridoma* 16:392 (Aug. 1997).

Sakata, Y. et al., "Clot Lysis Induced by a Monoclonal Antibody Against $\alpha_2$–Plasmin Inhibitor," *Blood* 74:2692–2697 (1989).

Soe, G. et al., "A rapid latex immunoassay for the detection of plasmin–$\alpha_2$–plasmin inhibitor complex. Utilization of two monoclonal antibodies differentially recognizing respective components of the complex," *Blood Coagulation & Fibrinolysis* 6:249–258 (May 1995).

Agnelli, G. et al., "The Comparative Effects of Recombinant Hirudin (CGP 39393) and Standard Heparin on Thrombus Growth in Rabbits," *Thrombosis and Hemostasis* 63 (2):204–207 (1990).

Agnelli, G. et al., "A comparison of the thrombolytic and hemorrhagic effects of tissue–type plasminogen activator and streptokinase in rabbits," *Circulation* 72(1):178–182 (1985).

Agnelli, G. et al., "Sustained Thrombolysis With DNA–Recombinant Tissue Type Plasminogen Activator in Rabbits," *Blood* 66 (2):399–401 (1985).

(List continued on next page.)

*Primary Examiner*—Yvonne Eyler
*Assistant Examiner*—Minh-Tam Davis
*Attorney, Agent, or Firm*—Sterne, Kessler, Goldstein & Fox P.L.L.C.

[57] ABSTRACT

The present invention relates to a novel alpha-2-antiplasmin-binding molecules and treatment for pulmonary embolism, myocardial infarction, thrombosis or stroke in a patient which comprises administering an alpha-2-antiplasmin-binding molecule capable of preventing inhibition of plasmin by endogenous alpha-2-antiplasmin. The invention also relates to a treatment for pulmonary embolism, myocardial infarction, thrombosis or stroke in a patient comprising coadministrating an alpha-2-antiplasmin-binding molecule of the invention together with a thrombolytic agent.

8 Claims, 22 Drawing Sheets

OTHER PUBLICATIONS

Angles–Cano, E. R., "Tissue plasminogen activator determination with a fibrin–supported film," *Chem. Abstracts* 104:307–308, Abstract No. 144639d (1986).

Aoki, N. et al., "Fibrin–Associated Plasminogen Activation in $\alpha_2$–Plasmin Inhibotor Deficiency," *Blood* 62(5):1118–1122 (1983).

Bates, E. R. et al., "A Monoclonal Antibody Against the Platelet Glycoprotein IIb/IIIa Receptor Complex Prevents Platelet Aggregation and Thrombosis in a Canine Model of Coronary Angioplasty," *Circulation* 84 (6):2463–2469 (1991).

Bode, C. et al., "Conjugation to Antifibrin Fab' Enhances Fibrinolytic Potency of Single–Chain Urokinase Plasminogen Activator," *Circulation* 81(6):1974–1980 (1990).

Bode, C., et al., "Antibody–Directed Urokinase: A Specific Fibrinolytic Agent," *Science* 229:765–767 (1985).

Bode, C. et al., "Thrombolysis by a Fibrin–specific Antibody Fab'–Urokinase Conjugate," *J. Mol. Cell. Cardiol.* 19:335–341 (1987).

Bode, C. et al., "Antibody–directed Fibrinolysis: An Antibody Specific For Both Fibrin and Tissue Plasminogen Activators," *J. Biol. Chem.* 264(2):944–948 (1989).

Boulianne, G. L. et al., "Production of functional chimaeric mouse/human antibody," *Nature* 312:643–646 (1984).

Branscomb, E. E. et al., "Bispecific Monoclonal Antibodies Produced by Somatic Cell Fusion Increase the Potency of Tissue Plasminogen Activator," *Thrombosis and Haemostasis* 64(2):260–266 (1990).

Brennan, M. et al., "Preparation of Bispecific Antibodies by Chemical Recombination of Monoclonal Immunoglobulin $G_1$ Fragments," *Science* 229:81–83 (1985).

Carrasquillo, J. A. et al., "Radioimmunodetection of Human Melanoma with Monoclonal Antibodies and Fab Fragments," in: *Radioimmunoimaging and Radioimmunotherapy*, Burchiel, S. and B. Rhodes, Eds, Elsevier Science Publishing Co., Inc.; Amsterdam, pp. 357–368 (1983).

Charpie, J. R. et al., "A Bispecific Antibody Enhances the Fibrinolytic Potency of Single–Chain Urokinase," *Biochemistry* 29(27):6374–6378 (1990).

Collen, D. et al., "Thrombolysis with Human Extrinsic (Tissue–Type) Plasminogen Activator in Rabbits with Experimental Jugular Vein Thrombosis," *J. Clin. Invest.* 71:368–376 (1983).

Collen, D. et al., "Thrombolytic and Pharmacokinetic Properties of Chimeric Tissue–Type and Urokinase–Type Plasminogen Activators," *Circulation* 84(3):1216–1234 (1991).

Collen, D. et al., "Synergism of thrombolytic agents in vivo," *Circulation* 74(4):838–842 (1986).

DeWood, M. A. et al., "Prevalence of Total Coronary Occlusion During the Early Hours of Transmural Myocardial Infarction," *New England J. Med.* 303(16):897–902 (1980).

Dorai, H. and G. P. Moore, "The Effect of Dihydrofolate Reductase–Mediated Gene Amplification on the Expression of Transfected Immunoglobulin Genes," *J. Immunol.* 139(12):4232–4241 (1987).

Duberstein, R., "Scientists Develop New Technique for Producing Bispecific Monoclonals," *Genetic Engineering News* 6:22–24 (1986).

Emeis, J. J. and J. H. Verheijen, "Thrombolytic Properties in a Rabbit Jugular Vein Thrombosis Model of a Tissue–type Plasminogen Activator Mutant Lacking the Growth Factor– and Kringle One–Domains," *Arzneim.–Forsch./Drug Res.* 42(3):358–362 (1992).

Fisher, R. et al., "Isolation and Characterization of the Human Tissue–type Plasminogen Activator Structural Gene Including Its 5' Flanking Region," *J. Biol. Chem.* 260(20):11223–11230 (1985).

Gardell, S. J. et al., "Effective Thrombolysis Without Marked Plasminemia After Bolus Intravenous Administration of Vampire Bat Salivary Plasminogen Activator in Rabbits," *Circulation* 84(1):244–253 (1991).

Gold, H. K. et al., "Acute coronary reocclusion after thrombolysis with recombinant human tissue–type plasminogen activator: prevention by a maintenance infusion," *Circulation* 73(2):347–352 (1986).

Harris, W.J. and S. Emery, "Therapeutic Antibodies—The Coming of Age," *T. Biotech.* 111:42–44 (1993).

Hattey, E. et al., "Monoclonal Antibodies Against Plasminogen and Alpha–2–Antiplasmin: Binding to Native and Modified Antigens," *Thrombosis Res.* 45:485–495 (1987).

Hessel, B. et al., "Primary Structure of Human Fibrinogen and Fibrin: Structural Studies on $NH_2$–terminal Part of $B\beta$ Chain," *Eur. J. Biochem.* 98:521–534 (1979).

Houranieh, A. et al., "Monoclonal Antibodies to Human Cross–Linked Fibrin," *Fed. Proc.* 44:1846, Abstract No. 8381 (1985).

Hui, K. Y. et al., "Immunodetection of Human Fibrin Using Monoclonal Antibody–64C5 in an Extracorporeal Chicken Model," *Thrombosis and Haemostasis* 54(2):524–527 (1985).

Hui, K. Y. et al., "Monoclonal Antibodies of Predetermined Specificity for Fibrin: A Rational Approach to Monoclonal Antibody Research," *Hybridoma* 5(3):215–222 (1986).

Hui, K. Y. et al., "Monoclonal Antibodies to a Synthetic Fibrin–Like Peptide Bind to Human Fibrin but not Fibrinogen," *Science* 222:1129–1132 (1983).

Ito, R. K. et al., "Fibrinolysis Studies: Fibrinogen–Specific Antibody as Carriers for Fibrinolytic Agents," *Fed. Proc.* 44:1846, Abstract No. 8382 (1985).

Kabnick, K. S. and D. E. Housman, "Determinants That Contribute to Cytoplasmic Stability of Human c–fos and $\beta$–Globin mRNAs Are Located at Several Sites in Each mRNA," *Mol. Cell. Biol.* 8(8):3244–3250 (1988).

Kato, K. et al., "A specific immunoassay system for hybrid type antigens," *Chem. Abstracts* 94:325, Abstract No. 61048j (1981).

Kimura, S. et al., "Acceleration of Fibrinolysis by the N–Terminal Peptide of $\alpha_2$–Plasmin Inhibitor," *Blood* 66(1):157–160 (1985).

Kudryk, B. et al., "A Monoclonal Antibody With Ability to Distinguish Between $NH_2$–Terminal Fragments Derived From Fibrinogen and Fibrin," *Mol. Immunol.* 20(11):1191–1200 (1983).

Kudryk, B. et al., "Specificity of a Monoclonal Antibody for the $NH_2$–Terminal Region of Fibrin," *Mol. Immunol.* 21(1):89–94 (1984).

Kumada, T. and Y. Abiko, "Physiological Role of $\alpha_2$–Plasmin Inhibitor in Rats," *Thrombisis Res.* 36:153–163 (1984).

Laffel, G. L. and E. Braunwald, "Thrombolytic Therapy: A New Strategy for the Treatment of Acute Myocardial Infarction (First of Two Parts)," *New England J. Med.* 311(11):710–717 (1984).

Laffel, G. L. and E. Braunwald, "Thrombolytic Therapy: A New Stragegy for the Treatment of Acute Myocardial Infarction (Second of Two Parts)," *New England J. Med.* 311(12):770–776 (1984).

Lanzavecchia, A. and D. Scheidegger, "The use of hybrid hybridomas to target human cytotoxic T lymphocytes," *Eur. J. Immunol.* 17:105–111 (1987).

Larsen, G. R. et al., "Protein Engineering of Novel Plasminogen Activators with Increased Thrombolytic Potency in Rabbits Relative to Activase," *J. Biol. Chem.* 266(13):8156–8161 (1991).

Lawn, R. M. et al., "The Nucleotide Sequence of the Human β–Globin Gene," *Cell* 21:647–651 (1980).

Lijnen, H. R. et al., "Comparative Fibrinolytic Properties of Staphylokinase and Streptokinase in Animal Models of Venous Thrombosis," *Thrombosis and Haemostasis* 66(4):468–473 (1991).

Lijnen, H. R. et al., "Biochemical and Thrombolytic Properties of a Low Molecular Weight Form (Comprising Leu$^{144}$ through Leu$^{411}$) of Recombinant Single–chain Urokinase–type Plasminogen Activator," *J. Biol. Chem.* 263(12):5594–5598 (1988).

Liu, M. A. et al., "Heteroantibody duplexes target cells for lysis by cytotoxic T lymphocytes," *Proc. Natl. Acad. Sci. USA* 82:8648–8652 (1985).

Love, T. W. et al., "Recombinant Antibodies Possessing Novel Effector Functions," *Meth. Enzymol.* 178:515–527 (1989).

Lukacova, D. et al., "Inhibition of Factor XIII Activation by an Anti–Peptide Monoclonal Antibody," *Biochemistry* 30(42):10164–10170 (1991).

Martin, U. et al., "Properties of a Novel Plasminogen Ativator (BM 06.022) produced in *Escherichia coli*," *Z. Kardiol.* 79(Suppl. 3):167–170 (1990).

Matsueda, G. R. et al., "A Monoclonal Antibody Specific for the C Terminus of Fibrinogen and Fibrin Gamma Chains," *FASEB J.* 2(5):A1411, Abstract No. 6480 (1988).

Matsueda, G. R. et al., "Fibrin–Specific Monoclonal Antibodies are Elicited by Immunization with a Synthetic Fibrin–Like Peptide," *Fibrinogen:Structural Variants and Interactions*, vol. 3, Henschen, A. et al., Eds., Walter de Gruyter, Berlin, (1985).

Matsueda, G. R. et al., "Monoclonal Antibodies Specific for Human Fibrin Monomer," *Fed. Proc.* 42(7):1992, Abstract No. 1375 (1983).

Matsueda, G. R. et al., "Detection of Thrombi: A Chicken Model Using Monoclonal Antibody Which Binds to Human Fibrin but not Fibrinogen," *Haemostasis* 14(1):44, Abstract No. 75 (1984).

Matsueda, G. R. et al., "Synthetic Fibrin–Like Peptides Used as Antigens Yield Fibrin–Specific Antibodies," *Peptides: Structure and Function. Proceedings of the Eighth American Peptide Symposium*, Hruby, V. J. and D. H. Rich, Eds., Pierce Chemical Company, Rockford, IL pp. 873–876 (1983).

Matsuo, D. et al., "Thrombolytic Effect of Single–Chain Pro–Urokinase in a Rabbit Jugular Vein Thrombosis Model," *Thrombosis Res.* 42:187–194 (1986).

Matsuo, O. et al., "Comparison of the Relative Fibrinogenolytic, Fibrinolytic and Thrombolytic Properties of Tissue Plasminogen Activator and Urokinase in Vitro," *Thrombos. Haemostas.* 45(3):225–229 (1981).

McCabe, R. P. et al., "A Diagnostic–Prognostic Test for Bladder Cancer Using a Monoclonal Antibody–based Enzyme–linked Immunoassay for Detection of Urinary Fibrin(ogen) Degradation Products," *Cancer Res.* 44:5886–5893 (1984).

Miles, L. A. et al., "A Bleeding Disorder Due to Deficiency of $\alpha_2$–Antiplasmin," *Blood* 59(6):1246–1251 (1982).

Milstein, C. and A. C. Cuello, "Hybrid hybridomas and their use in immunohistochemistry," *Nature* 305:537–540 (1983).

Morrison, S. L. and V. T. Oi, "Genetically Engineered Antibody Molecules," *Adv. Immunol.* 44:65–92 (1989).

Morrison, S. L., "Transfectomas Provide Novel Chimeric Antibodies," *Science* 229:1202–1207 (1985).

Morrison, S. L. et al., "Chimeric human antibody molecules: Mouse antigen–binding domains with human constant region domains," *Proc. Natl. Acad. Sci. USA* 81:6851–6855 (1984).

Munro, A., "Uses of chimeric antibodies," *Nature* 312:597 (1984).

Neuberger, M. S. et al., "Recombinant antibodies possessing novel effector functions," *Nature* 312:604–608 (1984).

Neuberger, M. S. et al., "A hapten–specific chimaeric IgE antibody with human physiological effector functions," *Nature* 314:268–270 (1985).

Nisonoff, A. and W. J. Mandy, "Quantitative Estimation of the Hybridization of Rabbit Antibodies," *Nature* 194:355–359 (1962).

Nossel, H. L., "Relative proteolysis of the fibrinogen Bβ chain by thrombin and plasmin as a determinant of thrombosis," *Nature* 291:165–167 (1981).

Oi, V. T. and S. L. Morrison, "Chimeric Antibodies," *BioTechniques* 4(3):214–221 (1986).

Pacella, B. L. et al., "Induction of Fibrin–Specific Antibodies by Immunization with Synthetic Peptides That Correspond to Amino Termini of Thrombin Cleavage Sites," *Mol. Immunol.* 20(5):521–527 (1983).

Philpott, G. W. et al., "Selective Cytotoxicity of Hapten–Substituted Cells With an Antibody–Enzyme Conjugate," *J. Immunol.* 111(3):921–929 (1973).

Philpott, G. W. et al., "Selective Binding and Cytotoxicity of Rat Basophilic Leukemia Cells (RBL–1) with Immunoglobulin E–Biotin and Avidin–Glucose Oxidase Conjugates," *J. Immunol.* 125(3):1201–1209 (1980).

Pizzo, S. V. et al., "The Effect of Plasmin on the Subunit Structure of Human Fibrin," *J. Biol. Chem.* 248(13):4574–4583 (1973).

Plow, E. F. et al., "Changes in Antigenic Structure and Conformation of $\alpha_2$–Antiplasmin Induced by Interaction with Plasmin," *J. Biol. Chem.* 255(7):2902–2906 (1980).

Rajagopalan, S. et al., "A Nonantigenic Covalent Streptokinase–Polyethylene Glycol Complex with Plasminogen Activator Function," *J. Clin. Invest.* 75:413–419 (1985).

Reed, G. L. et al., "Inhibition of Clot–Bound $\alpha_2$–Antiplasmin Enhances in Vivo Thrombolysis," *Circulation* 82(1):164–168 (1990).

Reed, G. L. et al., "Acceleration of Plasma Clot Lysis by an Antibody to $\alpha_2$–Antiplasmin," *Trans. Assoc. Am. Phys.* 101:250–256 (1988).

Reed, G. L. et al., "Synergisitic fibrinolysis: Combined effects of plasminogen activators and an antibody that inhibits $\alpha_2$–antiplasmin," *Proc. Natl. Acad. Sci. USA* 87(3):1114–1118 (1990).

Reed, G. L. et al., "Selective Inhibition of $\alpha_2$–Antiplasmin Augments the Potency and Specificity of Plasminogen Activators," *J. Am. Coll. Cardiol.* 13(2):2A (1989).

Rosebrough, S. F. et al., "Radioimmunoimaging of Venous Thrombi Using Iodine–131 Monoclonal Antibody," *Radiology* 156:515–517 (1985).

Runge, M. S. et al., "Antibody–Enhanced Thrombolysis: Capture of Tissue Plasminogen Activator by a Bispecific Antibody and Direct Targeting by an Antifibrin–Tissue Plasminogen Activator Conjugate In vivo," *Trans. Assoc. Am. Phys.* 100:250–255 (1987).

Runge, M. S. et al., "Conjugation to an Antifibrin Monoclonal Antibody Enhances the Fibrinolytic Potency of Tissue Plasminogen Activator in Vitro," *Biochemistry* 27:1153–1157 (1988).

Runge, M. S. et al., "Increasing Selectivity of Plasminogen Activators with Antibodies," *Clin. Res.* 36(5):501–506 (1988).

Runge, M. S. et al., "Antibody–enhanced thrombolysis: Targeting of tissue plasminogen activator in vivo," *Proc. Natl. Acad. Sci. USA* 84:7659–7662 (1987).

Runge, M. S. et al., "Antibody–Directed Fibrinolysis: A Bispecific (Fab')$_2$ That Binds to Fibrin and Tissue Plasminogen Activator," *Bioconjugate Chemistry* 1(4):274–277 (1990).

Sakata, Y. and N. Aoki, "Significance of Cross–Linking of $\alpha_2$–Plasmin Inhibitor to Fibrin in Inhibition of Fibrinolysis and in Hemostasis," *J. Clin. Invest.* 69:536–542 (1982).

Scheefers–Borchel, U. et al., "Discrimination between fibrin and fibrinogen by a monoclonal antibody against a synthetic peptide," *Proc. Natl. Acad. Sci. USA* 82:7091–7095 (1985).

Schnee, J. M. et al., "Construction and expression of a recombinant antibody–targeted plasminogen activator," *Proc. Natl. Acad. Sci. USA* 84:6904–6908 (1987).

Sevilla, C. L. et al., "Plasminogen Activator–Anti–Human Fibrinogen Conjugate," *Fed. Proc.* 44(4):1073, Abstract No. 3872 (1985).

Sevilla, C. L. et al., "Plasminogen Activator–Anti–Human Fibrinogen Conjugate," *Biochem. Biophys. Res. Commun.* 130(1):91–96 (1985).

Sharma, G. V. R. K. et al., "Medical Intelligence: Thrombolytic Therapy," *N. England. J. Med.* 306(21):1268–1276 (1982).

Sharon, J. et al., "Expression of a $V_H C_K$ chimaeric protein in mouse myeloma cells," *Nature* 309:364–367 (1984).

Sobel, B. E. et al., "Augmented and Sustained Plasma Concentrations After Intramuscular Injections of Molecular Variants and Deglycosylated Forms of Tissue–Type Plasminogen Activators," *Circulation* 81(4):1362–1373 (1990).

Sobel, J. H. et al., "Characterization of a Crosslink–Containing Fragment Derived from the $\alpha$ Polymer of Human Fibrin and Its Application in Immunologic Studies using Monoclonal Antibodies," *Thrombos. and Haemostas.* 46(1):240, Abstract No. 0758 (1981).

Soria, J. et al., "Monoconal Antibodies that React Preferentially With Fibrinogen Degradation Products or With Cross–Linked Fibrin Split Products," *Ann. N. Y. Acad. Sci* 408:665–666 (1983).

Staerz, U. D. and M. J. Bevan, "Hybrid hybridoma producing a bispecific monoclonal antibody that can focus effector T–cell activity," *Proc. Natl. Acad. Sci. USA* 83:1453–1457 (1986).

Stump, D. C. et al., "Comparative Thrombolytic Properties of Single–Chain Forms of Urokinase–Type Plasminogen Activator," *Blood* 69(2):592–596 (1987).

Thorpe, R. et al., "Single Shot Intrasplenic Immunization: An Advantageous Procedure for Production of Monoclonal Antibodies Specific for Human Fibrin Fragments," *Hybridoma* 3(4):381–385 (1984).

Tucker, P. W. et al., "Sequence of the Cloned Gene for the Constant Region of Murine $\gamma$2b Immunoglobulin Heavy Chain," *Science* 206:1303–1306 (1979).

van Zonneveld, A. et al., "Structure and Function of Human Tissue–Type Plasminogen Activator (t–PA)," *J. Cell. Biochem.* 32:169–178 (1986).

Verde, P. et al., "Identification and primary sequence of an unspliced human urokinase poly(A)$^+$ RNA," *Proc. Natl. Acad. Sci. USA* 81:4727–4731 (1984).

Waldmann, T. A., "Monoclonal Antibodies in Diagnosis and Therapy," *Science* 252:1657–1662 (1991).

Whitaker, A. N. et al., "Measurement of Crosslinked Fibrin Degradation Products Using Monoclonal Antibodies: Use in the Study of Intravascular Coagulation," *Pathology* 16:357–358 (1984).

Williams, G. T. and M. S. Neuberger, "Production of antibody–tagged enzymes by myeloma cells: application to DNA polymerase I Klenow fragment," *Gene* 43:319–324 (1986).

Wiman, B. et al., "Determination of plasmin–$\alpha_2$–antiplasmin complex in plasma samples by means of a radioimmunoassay," *Scand. J. Clin. Lab. Invest.* 43:27–33 (1983).

Wojta, J. et al., "Anwendung monoklonaler Antikörper in der Fibrinolysediagnostik," *Wiener klinische Wochenschrift* 97(5):244–248 (1985).

Zamarron, C. et al., "Influence of Exogenous and Endogenous Tissue–Type Plasminogen Activator on the Lysability of Clots in a Plasma Milieu In Vitro," *Thrombosis Res.* 35:335–345 (1984).

English language abstract of Japanese Patent No. 61–268630 (Document AP3), WPI Acc. No. 87–010915/02.

English Language Translation of Wojta, J. et al. (Reference No. AT36).

Declaration under 37 C.F.R. § 1.132 of Dr. Guy L. Reed, submitted on Aug. 10, 1992 in U.S. Application No. 07/589,003, filed Sep. 27, 1990 (Abandoned), a file–wrapper continuation of 07/589,003 was filed Sep. 10, 1992 and given U.S. Application No. 07/943,372, now U.S. Patent No. 5,372,812, issued Dec. 13, 1994, pp 5.

| MAb Light Chain | Amino Terminal Sequence |
|---|---|
| 49C9 | xIQMTQSPASLSASV |
| 70B11 | DIQMT |
| 77A3 | xIQMTQSPASLSASV |

FIG.10

```
         10         20         30         40         50         60
          *          *        G *          *          *          *
ATGAGTGTGC TCACTCAGGT CCTGGCGTTG CTGCTGCTGT GGCTTACAGG TGCCAGATGT
 M  S  V   L  T  Q  V  L  G  L   L  L  L   W  L  T  G  A  R  C>
                          A 70         80         90        100        110        120
          *          *          *          *          *          *
GACATCCAGA TGACTCAGTC TCCAGCCTCC CTATCTGCAT CTGTGGGAGA AACTGTCACC
 D  I  Q   M  T  Q  S  P  A  S   L  S  A   S  V  G  E  T  V  T>

130        140        150        160        170        180
          *          *          *          *          *          *
ATCACATGTC GAGCAAGTGG GAATATTCAC AATTATTTAG CATGGTATCA GCAGAAACAG
 I  T  C   R  A  S  G  N  I  H   N  Y  L   A  W  Y  Q  Q  K  Q>

190        200        210        220        230        240
          *          *          *          *          *          *
GGAAAATCTC CTCAGCTCCT GGTCTATAAT GCAAAAACCT TAGCAGATGG TGTGCCATCA
 G  K  S   P  Q  L  L  V  Y  N   A  K  T   L  A  D  G  V  P  S>

250        260        270        280        290        300
          *          *          *          *          *          *
AGGTTCAGTG GCAGTGGATC AGGAACACAA TTTTCTCTCA GGATCAACAG CCTGCAGCCT
 R  F  S   G  S  G  S  G  T  Q   F  S  L   R  I  N  S  L  Q  P>

310        320        330        340        350        360
          *          *          *          *          *          *
GAAGATTTTG GGAGTCATTA CTGTCAACAT TTTTGGACCA CTCCGTGGAC GTTCGGTGGA
 E  D  F   G  S  H  Y  C  Q  H   F  W  T   T  P  W  T  F  G  G>

370        380
          *          *
GGCACCAAGC TGGAAATCAA A
 G  T  K   L  E  I  K
```

FIG.11

```
         10         20         30         40         50         60
         *          *          *          *          *          *
ATGAGTGTGC TCACTCAGGT CCTGGGGTTG CTGCTGCTGT GGCTTACAGG TGCCAGATGT
 M  S  V   L  T  Q  V   L  G  L   L  L  L   W  L  T   G  A  R  C>

70         80         90        100        110        120
         *          *          *          *          *          *
GACATCCAGA TGACTCAGTC TCCAGCCTCC CTATCTGCAT CTGTGGGAGA AACTGTCACC
 D  I  Q   M  T  Q  S   P  A  S   L  S  A   S  V  G  E   T  V  T>

130        140        150        160        170        180
         *          *          *          *          *          *
GTCACATGTC GAGCAAGTGG GAATATTCAC AATTATTTAG CATGGTATCA GCAGAAACAG
 V  T  C   R  A  S  G   N  I  H   N  Y  L   A  W  Y  Q   Q  K  Q>

190        200        210        220        230        240
         *          *          *          *          *          *
GGAAAATCTC CTCAGCTCCT GGTCTATAAT GCAAGAACCT TAGCAGATGG TGTGCCATCA
 G  K  S   P  Q  L  L   V  Y  N   A  R  T   L  A  D  G   V  P  S>

250        260        270        280        290        300
         *          *          *          *          *          *
AGGTTCAGTG GCAGTGGATC AGGAACACAA TATTCTCTCA AGATCAACAG CCTGCAGCCT
 R  F  S   G  S  G  S   G  T  Q   Y  S  L   K  I  N  S   L  Q  P>

310        320        330        340        350        360
         *          *          *          *          *          *
GAAGATTTTG GGAGTTATTA CTGTCAACAT TTTTGGAGTA ATCCGTGGAC GTTCGGTGGA
 E  D  F   G  S  Y  Y   C  Q  H   F  W  S   N  P  W  T   F  G  G>

370        380
         *          *
GGCACCAAGC TGGAAATCAA
 G  T  K   L  E  I  K
```

FIG.12

```
          10         20         30         40         50         60
           *          *          *          *          *          *
ATGAGTGTGC TCACTCAGGT CCTGGCGTTG CTGCTGCTGT GGCTTACAGG TGCCAGATGT
 M  S  V    L  T  Q  V  L  A  L  L  L  L  W  L  T  G   A  R  C>

70         80         90        100        110        120
           *          *          *          *          *          *
GACATCCAGA TGACTCAGTC TCCAGCCTCC CTATCTGCAT CTGTGGGAGA AACTGTCACC
 D  I  Q   M  T  Q  S  P  A  S   L  S  A   S  V  G  E  T  V  T>

130        140        150        160        170        180
           *          *          *          *          *          *
ATCACATGTC GAGCAAGTGG GAATATTCAC AATTATTTAG CATGGTATCA GCAGAAACAG
 I  T  C   R  A  S  G  N  I  H   N  Y  L   A  W  Y  Q  Q  K  Q>

190        200        210        220        230        240
           *          *          *          *          *          *
GGAAAATCTC CTCAACTCCT GGTCTATAAT GCAAAAACCT TAGCAGATGG TGTGCCATCA
 G  K  S   P  Q  L  L  V  Y  N   A  K  T   L  A  D  G  V  P  S>

250        260        270        280        290        300
           *          *          *          *          *          *
AGGTTCAGTG GCAGTGGATC AGGAACACAA TTTTCTCTCA AGATCAACAG CCTGCAGCCT
 R  F  S   G  S  G  S  G  T  Q   F  S  L   K  I  N  S  L  Q  P>

310        320        330        340        350        360
           *          *          *          *          *          *
GAAGATTTTG GGAGTCATTA CTGTCAACAT TTTTGGACCA CTCCGTGGAC GTTCGGTGGA
 E  D  F   G  S  H  Y  C  Q  H   F  W  T   T  P  W  T  F  G  G>

370        380
           *          *
GGCACCAAGC TGGAAATCAA A
 G  T  K   L  E  I  K
```

H2 HC (49c9 heavy chain)

```
          9         19         29         39         49         59
          *         *         *         *         *         *
ATGGMTTGG GTGTGGAMCT TGCTATTCCT GATGGCAGCT GCCCAAAGTC TCCAAGCACA
 M  A  W   V  W  N   L  L  F  L   M  A  A   A  Q  S   L  Q  A  Q>
    D      T 69         79         89         99        109        119
          *         *         *         *         *         *
GATCCAGTTG GTGCAGTCTG GACCTGAGCT GAAGAAGCCT GGAGAAACAG TCAAGATCTC
 I  Q  L   V  Q  S   G  P  E  L   K  K  P   G  E  T   V  K  I  S>

129        139        149        159        169        179
          *         *         *         *         *         *
CTGCAAGGCC TCTGGGTATA CCTTCACAAA CTATGGAATG AACTGGGTGA AGCAGGCTCC
 C  K  A   S  G  Y   T  F  T  N   Y  G  M   N  W  V   K  Q  A  P>

189        199        209        219        229        239
          *         *         *         *         *         *
AGGAAAGGGT TTAAAGTGGA TGGGCTGGAT AAACACCAAG AGTGGAGAGC CAACATATGC
 G  K  G   L  K  W   M  G  W  I   N  T  K   S  G  E   P  T  Y  A>

249        259        269        279        289        299
          *         *         *         *         *         *
TGAAGAGTTC AAGGGACGGT TTGTCTTCTC TTTGGAAACC TCTGCCAGCA CTGCCCATTT
 E  E  F   K  G  R   F  V  F  S   L  E  T   S  A  S   T  A  H  L>

309        319        329        339        349        359
          *         *         *         *         *         *
GCAGATCAAG AATTTCAGAA ATGAGGACAC GGCTACATAT TTCTGTGCAA GATGGGTACC
 Q  I  K   N  F  R   N  E  D  T   A  T  Y   F  C  A   R  W  V  P>

369        379        389        399        409
          *         *         *         *         *
TGGGACCTAT GCTATGGACT ACTGGGGTCA AGGAACCTCA GTCACCGTCT CCTCA
 G  T  Y   A  M  D   Y  W  G  Q   G  T  S   V  T  V   S  S>
```

FIG. 15

H3 HC (70B11 heavy chain)

```
         10         20         30         40         50         60
          *          *          *          *          *          *
ATGGMTTGGG TGTGGAMCTT GCTATTCCTG ATGGCAGCTG CCCAAGTAT CCAAGCACAG
 M  A  W   V  W  N  L   L  F  L    M  A  A    A  Q  S  I    Q  A  Q>
    D           T 70         80         90        100        110        120
          *          *          *          *          *          *
ATCCAGTTGG TGCAGTCTGG ACCTGAGCTG AAGAAGCCTG GAGAGACAGT CAAGATCTCC
 I  Q  L   V  Q  S  G   P  E  L    K  K  P    G  E  T  V   K  I  S>

130        140        150        160        170        180
          *          *          *          *          *          *
TGCAAGGCTT CTGGGTATAC CTTCACAAAG TATGGAATGA ACTGGGTGAA GCAGGCTCCA
 C  K  A   S  G  Y  T   F  T  K    Y  G  M    N  W  V  K   Q  A  P>

190        200        210        220        230        240
          *          *          *          *          *          *
GGAAAGGGTT TAAAGTGGAT GGGCTGGATA AACACCAACA GTGGAGAGCC AACATATGCT
 G  K  G   L  K  W  M   G  W  I    N  T  N    S  G  E  P   T  Y  A>

250        260        270        280        290        300
          *          *          *          *          *          *
GAAGAGTTCA AGGGACGGTT TGCCTTCTCT TTGGAAACCT CTGCCAGCAC TGCCTATTTG
 E  E  F   K  G  R  F   A  F  S    L  E  T    S  A  S  T   A  Y  L>

310        320        330        340        350        360
          *          *          *          *          *          *
CAGATCAACA ACCTCAAAAA TGAGGACTCG GCTACATATT TCTGTGCAAG ATGGGTACCT
 Q  I  N   N  L  K  N   E  D  S    A  T  Y    F  C  A  R   W  V  P>

370        380        390        400        410
          *          *          *          *          *
GGGACCTATG CTATGGACTA CTGGGGTCAA GGAACCTCAG TCACCGTCTC CTCA
 G  T  Y   A  M  D  Y   W  G  Q    G  T  S    V  T  V  S   S>
```

```
H4 HC (77A3 heavy chain)
         10        20        30        40        50        60
         *         *         *         *         *         *
ATGGMTTGGG TGTGGAMCTT GCTATTCCTG ATGGCAGCTG CCCAAAGTAT CCAAGCACAG
 M  A  W   V  W  N  L  L  F  L   M  A  A   A  Q  S  I   Q  A  Q>
 D         T 70        80        90       100       110       120
         *         *         *         *         *         *
ATCCAGTTGG TGCAGTCTGG ACCTGAGCTG AAGAAGCCTG GAGAAACAGT CAAGATCTCC
 I  Q  L   V  Q  S  G  P  E  L   K  K  P   G  E  T  V   K  I  S>

130       140       150       160       170       180
         *         *         *         *         *         *
TGCAAGGCTT CTGGGTATAC CTTCACAAAC TATGGAATGA ACTGGGTGAA GCAGGCTCCA
 C  K  A   S  G  Y  T  F  T  N   Y  G  M   N  W  V  K   Q  A  P>

190       200       210       220       230       240
         *         *         *         *         *         *
GGAAAGGGTT TAAAGTGGAT GGGCTGGATA AACACCAAGA GTGGAGAGCC AACATATGCT
 G  K  G   L  K  W  M  G  W  I   N  T  K   S  G  E  P   T  Y  A>

250       260       270       280       290       300
         *         *         *         *         *         *
GAAGAGTTCA AGGGACGGGT TGCCTTCTCT TTGGAAACCT CTGCCAGCAC TGCCAATTTG
 E  E  F   K  G  R  F  A  F  S   L  E  T   S  A  S  T   A  N  L>

310       320       330       340       350       360
         *         *         *         *         *         *
CAGATCAAGA ACCTCAAAAA TGAGGACACG GCTACATATT TCTGTGCAAG ATGGGTACCT
 Q  I  K   N  L  K  N  E  D  T   A  T  Y   F  C  A  R   W  V  P>

370       380       390       400       410
         *         *         *         *         *
GGGACCTATG CCATGGACTA CTGGGGTCAA GGAACCTCAG TCACCGTCTC CTCA
 G  T  Y   A  M  D  Y  W  G  Q   G  T  S   V  T  V  S   S
```

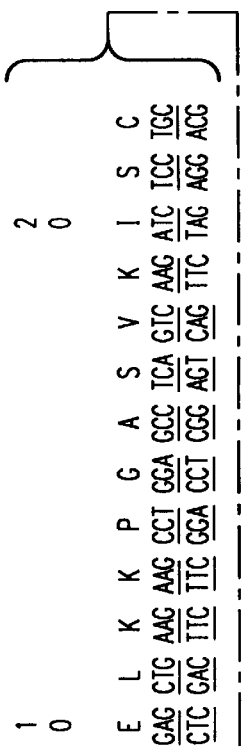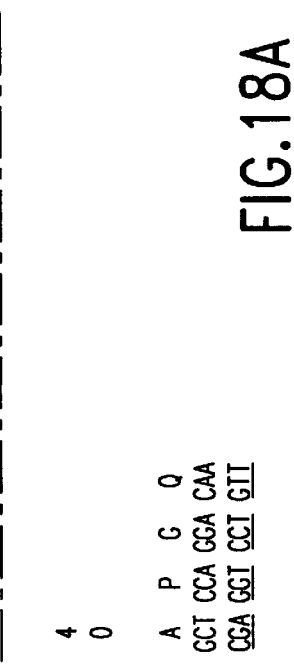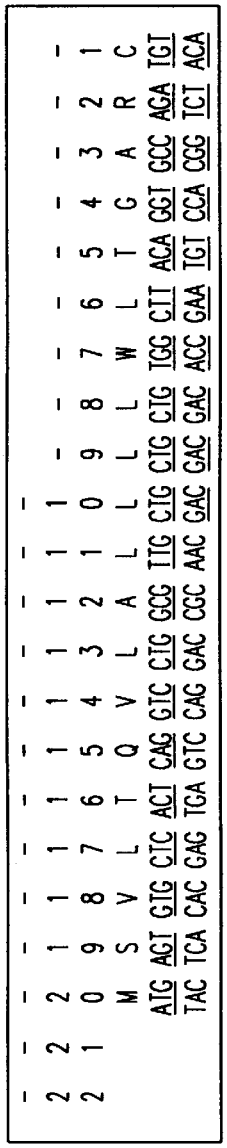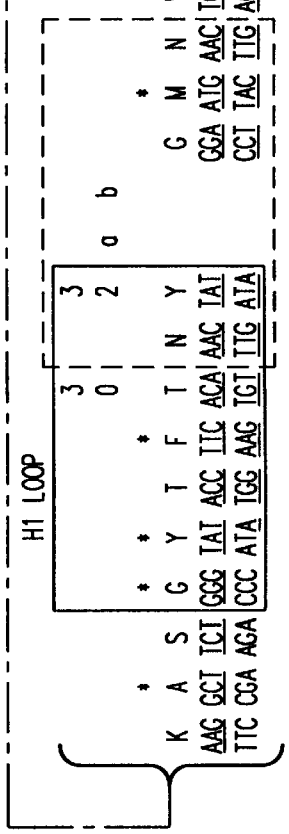
FIG.18A

FIG. 21

L1 Loop region (positions 1–34):

```
                          1         10         20         27 30 31abcdef 32 33 34
h77A3-1 and h77A3-2       D I Q M T Q S P S S L S A S V G D R V T I T C R A S G N I H N       Y L A
m77A3                     D I Q M T Q S P A S L S A S V G E T V T I T C R A S G N I H N       Y L A
m49C9                     D I Q M T Q S P A S L S A S V G E T V T I T C R A S G N I H N       Y L A
m70B11                    D I Q M T Q S P A S L S A S V G E T V T V T C R A S G N I H N       Y L A
murine consensus          D I Q M T Q S P A S L S A S V G E T V T X T C R A S G N I H N       Y L A
77A3/49C9 consensus       D I Q M T Q S P X S L S A S V G X T V T I T C R A S G N I H N       Y L A
all                       D I Q M T Q S P X S L S A S V G X X V X X T C R A S G N I H N       Y L A
```

L2 Loop region (positions 35–70):

```
                          35          40              50                60           70
h77A3-1 and h77A3-2       W Y Q Q K Q G K S P Q L L V Y   N A K T L A   S G V P S R F S G S G T D F T L T
m77A3                     W Y Q Q K Q G K S P Q L L V Y   N A K T L A   D G V P S R F S G S G S G T Q F S L K
m49C9                     W Y Q Q K Q G K S P Q L L V Y   N A K T L A   D G V P S R F S G S G S G T Q F S L R
m70B11                    W Y Q Q K Q G K S P Q L L V Y   N A R T L A   D G V P S R F S G S G S G T Q Y S L K
murine consensus          W Y Q Q K Q G K S P Q L L V Y   N A K T L A   D G V P S R F S G S G S G T Q F S L X
77A3/49C9 consensus       W Y Q Q K Q G K S P Q L L V Y   N A K T L A   X D G V P S R F S G S G S G T X X X L X
all                       W Y Q Q K Q G K S P Q L L V Y   N A X T L A   X G V P S R F S G S G S G T X X X L X
```

L3 Loop region (positions 75–97):

```
                          75          80          85      90           95 96 a 97
h77A3-1 and h77A3-2       I S S L Q P E D F G S H Y C Q   H F W T P         W T F G G G T K L E I K
m77A3                     I N S L L P E D F G S S Y C Q   H F W S N P       W T F G G G T K L E I K
m49C9                     I N S L L P E D F G S S Y C Q   H F W S N P       W T F G G G T K L E I K
m70B11                    I N S L L P E D F G S X Y C Q   H F W X T P       W T F G G G T K L E I K
murine consensus          I N S L L P E D F G S X Y C Q   H F W X T P       W T F G G G T K L E I K
77A3/49C9 consensus       I N S L L P E D F G S X Y C Q   H F W X X P       W T F G G G T K L E I K
all                       I X S L Q P E D F G S X Y C Q   H F W X X P       W T F G G G T K L E I K
```

H3 LOOP positions: 83 ... 90 ... (0 a b c d e f g h i j k 10 1) ... 94 ... 100 101

| | 83 | | | | | | 90 | | | | | | | 94 | | | | H3 LOOP 0 a b c d e f g h i j k 10 1 | | | | | | | | | | | | 100 101 |
|---|---|---|---|---|---|---|---|---|---|---|---|---|---|---|---|---|---|---|---|---|---|---|---|---|---|---|---|---|
| h77A3-1 | K A E D T A V Y F | C A R W | V P G T | Y A M D Y | W G Q G T T V T V S S |
| h77A3-2 | R S D D T A V Y F | C A R W | V P G T | Y A M D Y | W G Q G T T V T V S S |
| m77A3 | K N E D T A T Y F | C A R W | V P G T | Y A M D Y | W G Q G T S V T V S S |
| m49C9 | K R N E D T A T Y F | C A R W | V P G T | Y A M D Y | W G Q G T S V T V S S |
| m70B11 | K N E D S A T Y F | C A R W | V P G T | Y A M D Y | W G Q G T S V T V S S |
| humanized consensus 1 | X X X E D X A V Y F | C A R W | V P G T | Y A M D Y | W G Q G T T V T V S S |
| murine consensus 2 | X X N E D T A T Y F | C A R W | V P G T | Y A M D Y | W G Q G T S V T V S S |
| 77A3/49C9 consensus all | X X X X D X A X Y F | C A R W | V P G T | Y A M D Y | W G Q G T X V T V S S |

SEQUENCE LISTING (1) GENERAL INFORMATION:

(iii) NUMBER OF SEQUENCES: 81

(2) INFORMATION FOR SEQ ID NO:1:

(i) SEQUENCE CHARACTERISTICS:
      (A) LENGTH: 15 amino acids
      (B) TYPE: amino acid
      (C) STRANDEDNESS: single
      (D) TOPOLOGY: Not Relevant (ii) MOLECULE TYPE: peptide (xi) SEQUENCE DESCRIPTION: SEQ ID NO:1:

```
Xaa Ile Gln Met Thr Gln Ser Pro Ala Ser Leu Ser Ala Ser Val
1               5                   10                  15
```

(2) INFORMATION FOR SEQ ID NO:2:

(i) SEQUENCE CHARACTERISTICS:
        (A) LENGTH: 5 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:2:

```
Asp Ile Gln Met Thr
1               5
```

(2) INFORMATION FOR SEQ ID NO:3:

(i) SEQUENCE CHARACTERISTICS:
        (A) LENGTH: 15 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:3:

```
Xaa Ile Gln Met Thr Gln Ser Pro Ala Ser Leu Ser Ala Ser Val
1               5                   10                  15
```

(2) INFORMATION FOR SEQ ID NO:4:

(i) SEQUENCE CHARACTERISTICS:
        (A) LENGTH: 381 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..381

(ix) FEATURE:
        (A) NAME/KEY: sig_peptide
        (B) LOCATION: 1..60

(xi) SEQUENCE DESCRIPTION: SEQ ID NO:4:

```
ATG AGT GTG CTC ACT CAG GTC CTG GSG TTG CTG CTG TGG CTT ACA         48
Met Ser Val Leu Thr Gln Val Leu Xaa Leu Leu Leu Trp Leu Thr
-20                 -15                 -10

GGT GCC AGA TGT GAC ATC CAG ATG ACT CAG TCT CCA GCC TCC CTA TCT     96
Gly Ala Arg Cys Asp Ile Gln Met Thr Gln Ser Pro Ala Ser Leu Ser
            -1              5                   10

GCA TCT GTG GGA GAA ACT GTC ACC ATC ACA TGT CGA GCA AGT GGG AAT    144
Ala Ser Val Gly Glu Thr Val Thr Ile Thr Cys Arg Ala Ser Gly Asn
        15                  20                  25

ATT CAC AAT TAT TTA GCA TGG TAT CAG CAG AAA CAG GGA AAA TCT CCT    192
Ile His Asn Tyr Leu Ala Trp Tyr Gln Gln Lys Gln Gly Lys Ser Pro
        30                  35                  40

CAG CTC CTG GTC TAT AAT GCA AAA ACC TTA GCA GAT GGT GTG CCA TCA    240
Gln Leu Leu Val Tyr Asn Ala Lys Thr Leu Ala Asp Gly Val Pro Ser
    45                  50                  55                  60

AGG TTC AGT GGC AGT GGA TCA GGA ACA CAA TTT TCT CTC AGG ATC AAC    288
Arg Phe Ser Gly Ser Gly Ser Gly Thr Gln Phe Ser Leu Arg Ile Asn
```

```
                65                   70                   75
AGC CTG CAG CCT GAA GAT TTT GGG AGT CAT TAC TGT CAA CAT TTT TGG       336
Ser Leu Gln Pro Glu Asp Phe Gly Ser His Tyr Cys Gln His Phe Trp
                80                   85                   90

ACC ACT CCG TGG ACG TTC GGT GGA GGC ACC AAG CTG GAA ATC AAA           381
Thr Thr Pro Trp Thr Phe Gly Gly Gly Thr Lys Leu Glu Ile Lys
                95                  100                  105
```

(2) INFORMATION FOR SEQ ID NO:5:

(i) SEQUENCE CHARACTERISTICS:
        (A) LENGTH: 127 amino acids
        (B) TYPE: amino acid
        (D) TOPOLOGY: linear (ii) MOLECULE TYPE: protein (ix) FEATURE:
        (A) NAME/KEY: Modified-site
        (B) LOCATION: 9
        (D) OTHER INFORMATION: /note= "Can be either Gly or Ala"

(xi) SEQUENCE DESCRIPTION: SEQ ID NO:5:

```
Met Ser Val Leu Thr Gln Val Leu Xaa Leu Leu Leu Trp Leu Thr
-20                 -15                 -10                  -5

Gly Ala Arg Cys Asp Ile Gln Met Thr Gln Ser Pro Ala Ser Leu Ser
                -1                   5                  10

Ala Ser Val Gly Glu Thr Val Thr Ile Thr Cys Arg Ala Ser Gly Asn
                15                  20                  25

Ile His Asn Tyr Leu Ala Trp Tyr Gln Gln Lys Gln Gly Lys Ser Pro
                30                  35                  40

Gln Leu Leu Val Tyr Asn Ala Lys Thr Leu Ala Asp Gly Val Pro Ser
45                  50                  55                  60

Arg Phe Ser Gly Ser Gly Ser Gly Thr Gln Phe Ser Leu Arg Ile Asn
                65                  70                  75

Ser Leu Gln Pro Glu Asp Phe Gly Ser His Tyr Cys Gln His Phe Trp
                80                  85                  90

Thr Thr Pro Trp Thr Phe Gly Gly Gly Thr Lys Leu Glu Ile Lys
                95                 100                 105
```

(2) INFORMATION FOR SEQ ID NO:6:

(i) SEQUENCE CHARACTERISTICS:
        (A) LENGTH: 381 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..381

(ix) FEATURE:
        (A) NAME/KEY: sig_peptide
        (B) LOCATION: 1..60

(xi) SEQUENCE DESCRIPTION: SEQ ID NO:6:

```
ATG AGT GTG CTC ACT CAG GTC CTG GGG TTG CTG CTG CTG TGG CTT ACA       48
Met Ser Val Leu Thr Gln Val Leu Gly Leu Leu Leu Leu Trp Leu Thr
-20                 -15                 -10                  -5

GGT GCC AGA TGT GAC ATC CAG ATG ACT CAG TCT CCA GCC TCC CTA TCT       96
Gly Ala Arg Cys Asp Ile Gln Met Thr Gln Ser Pro Ala Ser Leu Ser
                -1                   5                  10
```

```
GCA TCT GTG GGA GAA ACT GTC ACC GTC ACA TGT CGA GCA AGT GGG AAT        144
Ala Ser Val Gly Glu Thr Val Thr Val Thr Cys Arg Ala Ser Gly Asn
         15                  20                  25

ATT CAC AAT TAT TTA GCA TGG TAT CAG CAG AAA CAG GGA AAA TCT CCT        192
Ile His Asn Tyr Leu Ala Trp Tyr Gln Gln Lys Gln Gly Lys Ser Pro
     30                  35                  40

CAG CTC CTG GTC TAT AAT GCA AGA ACC TTA GCA GAT GGT GTG CCA TCA        240
Gln Leu Leu Val Tyr Asn Ala Arg Thr Leu Ala Asp Gly Val Pro Ser
 45                  50                  55                  60

AGG TTC AGT GGC AGT GGA TCA GGA ACA CAA TAT TCT CTC AAG ATC AAC        288
Arg Phe Ser Gly Ser Gly Ser Gly Thr Gln Tyr Ser Leu Lys Ile Asn
                 65                  70                  75

AGC CTG CAG CCT GAA GAT TTT GGG AGT TAT TAC TGT CAA CAT TTT TGG        336
Ser Leu Gln Pro Glu Asp Phe Gly Ser Tyr Tyr Cys Gln His Phe Trp
             80                  85                  90

AGT AAT CCG TGG ACG TTC GGT GGA GGC ACC AAG CTG GAA ATC AAA            381
Ser Asn Pro Trp Thr Phe Gly Gly Gly Thr Lys Leu Glu Ile Lys
         95                 100                 105
```

(2) INFORMATION FOR SEQ ID NO:7:

(i) SEQUENCE CHARACTERISTICS:
        (A) LENGTH: 127 amino acids
        (B) TYPE: amino acid
        (D) TOPOLOGY: linear (ii) MOLECULE TYPE: protein (xi) SEQUENCE DESCRIPTION: SEQ ID NO:7:

```
Met Ser Val Leu Thr Gln Val Leu Gly Leu Leu Leu Leu Trp Leu Thr
-20                 -15                 -10                  -5

Gly Ala Arg Cys Asp Ile Gln Met Thr Gln Ser Pro Ala Ser Leu Ser
             -1                   5                  10

Ala Ser Val Gly Glu Thr Val Thr Val Thr Cys Arg Ala Ser Gly Asn
         15                  20                  25

Ile His Asn Tyr Leu Ala Trp Tyr Gln Gln Lys Gln Gly Lys Ser Pro
     30                  35                  40

Gln Leu Leu Val Tyr Asn Ala Arg Thr Leu Ala Asp Gly Val Pro Ser
 45                  50                  55                  60

Arg Phe Ser Gly Ser Gly Ser Gly Thr Gln Tyr Ser Leu Lys Ile Asn
                 65                  70                  75

Ser Leu Gln Pro Glu Asp Phe Gly Ser Tyr Tyr Cys Gln His Phe Trp
             80                  85                  90

Ser Asn Pro Trp Thr Phe Gly Gly Gly Thr Lys Leu Glu Ile Lys
         95                 100                 105
```

(2) INFORMATION FOR SEQ ID NO:8:

(i) SEQUENCE CHARACTERISTICS:
        (A) LENGTH: 381 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..381

(ix) FEATURE:
        (A) NAME/KEY: sig_peptide
        (B) LOCATION: 1..60

(xi) SEQUENCE DESCRIPTION: SEQ ID NO:8:

| | | | | | | | | | | | | | | | |
|---|---|---|---|---|---|---|---|---|---|---|---|---|---|---|---|
| ATG | AGT | GTG | CTC | ACT | CAG | GTC | CTG | GCG | TTG | CTG | CTG | TGG | CTT | ACA | 48 |
| Met | Ser | Val | Leu | Thr | Gln | Val | Leu | Ala | Leu | Leu | Leu | Trp | Leu | Thr | |
| -20 | | | | -15 | | | | -10 | | | | | | -5 | |

| | | | | | | | | | | | | | | | |
|---|---|---|---|---|---|---|---|---|---|---|---|---|---|---|---|
| GGT | GCC | AGA | TGT | GAC | ATC | CAG | ATG | ACT | CAG | TCT | CCA | GCC | TCC | CTA | TCT | 96 |
| Gly | Ala | Arg | Cys | Asp | Ile | Gln | Met | Thr | Gln | Ser | Pro | Ala | Ser | Leu | Ser |
| | | | -1 | | | | | 5 | | | | | 10 | | |

GCA TCT GTG GGA GAA ACT GTC ACC ATC ACA TGT CGA GCA AGT GGG AAT    144
Ala Ser Val Gly Glu Thr Val Thr Ile Thr Cys Arg Ala Ser Gly Asn
         15                  20                  25

ATT CAC AAT TAT TTA GCA TGG TAT CAG CAG AAA CAG GGA AAA TCT CCT    192
Ile His Asn Tyr Leu Ala Trp Tyr Gln Gln Lys Gln Gly Lys Ser Pro
     30                  35                  40

CAA CTC CTG GTC TAT AAT GCA AAA ACC TTA GCA GAT GGT GTG CCA TCA    240
Gln Leu Leu Val Tyr Asn Ala Lys Thr Leu Ala Asp Gly Val Pro Ser
 45                  50                  55                  60

AGG TTC AGT GGC AGT GGA TCA GGA ACA CAA TTT TCT CTC AAG ATC AAC    288
Arg Phe Ser Gly Ser Gly Ser Gly Thr Gln Phe Ser Leu Lys Ile Asn
             65                  70                  75

AGC CTG CAG CCT GAA GAT TTT GGG AGT CAT TAC TGT CAA CAT TTT TGG    336
Ser Leu Gln Pro Glu Asp Phe Gly Ser His Tyr Cys Gln His Phe Trp
         80                  85                  90

ACC ACT CCG TGG ACG TTC GGT GGA GGC ACC AAG CTG GAA ATC AAA        381
Thr Thr Pro Trp Thr Phe Gly Gly Gly Thr Lys Leu Glu Ile Lys
     95                 100                 105

(2) INFORMATION FOR SEQ ID NO:9:

(i) SEQUENCE CHARACTERISTICS:
        (A) LENGTH: 127 amino acids
        (B) TYPE: amino acid
        (D) TOPOLOGY: linear (ii) MOLECULE TYPE: protein (xi) SEQUENCE DESCRIPTION: SEQ ID NO:9:

Met Ser Val Leu Thr Gln Val Leu Ala Leu Leu Leu Trp Leu Thr
-20                 -15                 -10                 -5

Gly Ala Arg Cys Asp Ile Gln Met Thr Gln Ser Pro Ala Ser Leu Ser
            -1                   5                  10

Ala Ser Val Gly Glu Thr Val Thr Ile Thr Cys Arg Ala Ser Gly Asn
         15                  20                  25

Ile His Asn Tyr Leu Ala Trp Tyr Gln Gln Lys Gln Gly Lys Ser Pro
     30                  35                  40

Gln Leu Leu Val Tyr Asn Ala Lys Thr Leu Ala Asp Gly Val Pro Ser
 45                  50                  55                  60

Arg Phe Ser Gly Ser Gly Ser Gly Thr Gln Phe Ser Leu Lys Ile Asn
             65                  70                  75

Ser Leu Gln Pro Glu Asp Phe Gly Ser His Tyr Cys Gln His Phe Trp
         80                  85                  90

Thr Thr Pro Trp Thr Phe Gly Gly Gly Thr Lys Leu Glu Ile Lys
     95                 100                 105

(2) INFORMATION FOR SEQ ID NO:10:

(i) SEQUENCE CHARACTERISTICS:
        (A) LENGTH: 414 base pairs
        (B) TYPE: nucleic acid
        (C) STRANDEDNESS: single
        (D) TOPOLOGY: linear (ii) MOLECULE TYPE: cDNA (ix) FEATURE:
         (A) NAME/KEY: CDS
         (B) LOCATION: 1..414

(ix) FEATURE:
         (A) NAME/KEY: sig_peptide
         (B) LOCATION: 1..57

(xi) SEQUENCE DESCRIPTION: SEQ ID NO:10:

```
ATG GMT TGG GTG TGG AMC TTG CTA TTC CTG ATG GCA GCT GCC CAA AGT        48
Met Xaa Trp Val Trp Xaa Leu Leu Phe Leu Met Ala Ala Ala Gln Ser
            -15                 -10                  -5

CTC CAA GCA CAG ATC CAG TTG GTG CAG TCT GGA CCT GAG CTG AAG AAG        96
Leu Gln Ala Gln Ile Gln Leu Val Gln Ser Gly Pro Glu Leu Lys Lys
         -1                   5                  10

CCT GGA GAA ACA GTC AAG ATC TCC TGC AAG GCC TCT GGG TAT ACC TTC       144
Pro Gly Glu Thr Val Lys Ile Ser Cys Lys Ala Ser Gly Tyr Thr Phe
         15                  20                  25

ACA AAC TAT GGA ATG AAC TGG GTG AAG CAG GCT CCA GGA AAG GGT TTA       192
Thr Asn Tyr Gly Met Asn Trp Val Lys Gln Ala Pro Gly Lys Gly Leu
 30              35                  40                  45

AAG TGG ATG GGC TGG ATA AAC ACC AAG AGT GGA GAG CCA ACA TAT GCT       240
Lys Trp Met Gly Trp Ile Asn Thr Lys Ser Gly Glu Pro Thr Tyr Ala
                 50                  55                  60

GAA GAG TTC AAG GGA CGG TTT GTC TTC TCT TTG GAA ACC TCT GCC AGC       288
Glu Glu Phe Lys Gly Arg Phe Val Phe Ser Leu Glu Thr Ser Ala Ser
             65                  70                  75

ACT GCC CAT TTG CAG ATC AAG AAT TTC AGA AAT GAG GAC ACG GCT ACA       336
Thr Ala His Leu Gln Ile Lys Asn Phe Arg Asn Glu Asp Thr Ala Thr
         80                  85                  90

TAT TTC TGT GCA AGA TGG GTA CCT GGG ACC TAT GCT ATG GAC TAC TGG       384
Tyr Phe Cys Ala Arg Trp Val Pro Gly Thr Tyr Ala Met Asp Tyr Trp
     95                 100                 105

GGT CAA GGA ACC TCA GTC ACC GTC TCC TCA                               414
Gly Gln Gly Thr Ser Val Thr Val Ser Ser
110             115
```

(2) INFORMATION FOR SEQ ID NO:11:

(i) SEQUENCE CHARACTERISTICS:
        (A) LENGTH: 138 amino acids
        (B) TYPE: amino acid
        (D) TOPOLOGY: linear (ii) MOLECULE TYPE: protein (ix) FEATURE:
         (A) NAME/KEY: modified-site
         (B) LOCATION: 2
         (D) OTHER INFORMATION: /note= "Can be Ala or Asp"

(ix) FEATURE:
         (A) NAME/KEY: modified-site
         (B) LOCATION: 6
         (D) OTHER INFORMATION: /note= "Can be Asn or Thr"

(xi) SEQUENCE DESCRIPTION: SEQ ID NO:11:

```
Met Xaa Trp Val Trp Xaa Leu Leu Phe Leu Met Ala Ala Ala Gln Ser
            -15                 -10                  -5

Leu Gln Ala Gln Ile Gln Leu Val Gln Ser Gly Pro Glu Leu Lys Lys
         -1                   5                  10

Pro Gly Glu Thr Val Lys Ile Ser Cys Lys Ala Ser Gly Tyr Thr Phe
         15                  20                  25
```

```
Thr Asn Tyr Gly Met Asn Trp Val Lys Gln Ala Pro Gly Lys Gly Leu
 30                  35                  40                  45

Lys Trp Met Gly Trp Ile Asn Thr Lys Ser Gly Glu Pro Thr Tyr Ala
             50                  55                  60

Glu Glu Phe Lys Gly Arg Phe Val Phe Ser Leu Glu Thr Ser Ala Ser
                 65                  70                  75

Thr Ala His Leu Gln Ile Lys Asn Phe Arg Asn Glu Asp Thr Ala Thr
             80                  85                  90

Tyr Phe Cys Ala Arg Trp Val Pro Gly Thr Tyr Ala Met Asp Tyr Trp
         95                 100                 105

Gly Gln Gly Thr Ser Val Thr Val Ser Ser
110                 115
```

(2) INFORMATION FOR SEQ ID NO:12:

(i) SEQUENCE CHARACTERISTICS:
        (A) LENGTH: 414 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..414

(ix) FEATURE:
        (A) NAME/KEY: sig_peptide
        (B) LOCATION: 1..57

(xi) SEQUENCE DESCRIPTION: SEQ ID NO:12:

```
ATG GMT TGG GTG TGG AMC TTG CTA TTC CTG ATG GCA GCT GCC CAA AGT        48
Met Xaa Trp Val Trp Xaa Leu Leu Phe Leu Met Ala Ala Ala Gln Ser
        -15                 -10                  -5

ATC CAA GCA CAG ATC CAG TTG GTG CAG TCT GGA CCT GAG CTG AAG AAG        96
Ile Gln Ala Gln Ile Gln Leu Val Gln Ser Gly Pro Glu Leu Lys Lys
         -1              5                  10

CCT GGA GAG ACA GTC AAG ATC TCC TGC AAG GCT TCT GGG TAT ACC TTC       144
Pro Gly Glu Thr Val Lys Ile Ser Cys Lys Ala Ser Gly Tyr Thr Phe
 15                  20                  25

ACA AAG TAT GGA ATG AAC TGG GTG AAG CAG GCT CCA GGA AAG GGT TTA       192
Thr Lys Tyr Gly Met Asn Trp Val Lys Gln Ala Pro Gly Lys Gly Leu
     30                  35                  40                  45

AAG TGG ATG GGC TGG ATA AAC ACC AAC AGT GGA GAG CCA ACA TAT GCT       240
Lys Trp Met Gly Trp Ile Asn Thr Asn Ser Gly Glu Pro Thr Tyr Ala
                 50                  55                  60

GAA GAG TTC AAG GGA CGG TTT GCC TTC TCT TTG GAA ACC TCT GCC AGC       288
Glu Glu Phe Lys Gly Arg Phe Ala Phe Ser Leu Glu Thr Ser Ala Ser
                     65                  70                  75

ACT GCC TAT TTG CAG ATC AAC AAC CTC AAA AAT GAG GAC TCG GCT ACA       336
Thr Ala Tyr Leu Gln Ile Asn Asn Leu Lys Asn Glu Asp Ser Ala Thr
                 80                  85                  90

TAT TTC TGT GCA AGA TGG GTA CCT GGG ACC TAT GCT ATG GAC TAC TGG       384
Tyr Phe Cys Ala Arg Trp Val Pro Gly Thr Tyr Ala Met Asp Tyr Trp
             95                 100                 105

GGT CAA GGA ACC TCA GTC ACC GTC TCC TCA                               414
Gly Gln Gly Thr Ser Val Thr Val Ser Ser
110                 115
```

(2) INFORMATION FOR SEQ ID NO:13:

(i) SEQUENCE CHARACTERISTICS:
    (A) LENGTH: 138 amino acids
    (B) TYPE: amino acid
    (D) TOPOLOGY: linear (ii) MOLECULE TYPE: protein (ix) FEATURE:
    (A) NAME/KEY: Modified-site
    (B) LOCATION: 2
    (C) OTHER INFORMATION: /note= "Can be Ala or Asp"

(ix) FEATURE:
    (A) NAME/KEY: Modified-site
    (B) LOCATION: 6
    (C) OTHER INFORMATION: /note= "Can be Asn or Thr"

(xi) SEQUENCE DESCRIPTION: SEQ ID NO:13:

Met Xaa Trp Val Trp Xaa Leu Leu Phe Leu Met Ala Ala Ala Gln Ser
        -15             -10              -5

Ile Gln Ala Gln Ile Gln Leu Val Gln Ser Gly Pro Glu Leu Lys Lys
    -1              5                   10

Pro Gly Glu Thr Val Lys Ile Ser Cys Lys Ala Ser Gly Tyr Thr Phe
    15              20                  25

Thr Lys Tyr Gly Met Asn Trp Val Lys Gln Ala Pro Gly Lys Gly Leu
30              35                  40                      45

Lys Trp Met Gly Trp Ile Asn Thr Asn Ser Gly Glu Pro Thr Tyr Ala
                50                  55                  60

Glu Glu Phe Lys Gly Arg Phe Ala Phe Ser Leu Glu Thr Ser Ala Ser
            65                  70                  75

Thr Ala Tyr Leu Gln Ile Asn Asn Leu Lys Asn Glu Asp Ser Ala Thr
            80                  85                  90

Tyr Phe Cys Ala Arg Trp Val Pro Gly Thr Tyr Ala Met Asp Tyr Trp
            95                  100                 105

Gly Gln Gly Thr Ser Val Thr Val Ser Ser
110                 115

(2) INFORMATION FOR SEQ ID NO:14:

(i) SEQUENCE CHARACTERISTICS:
        (A) LENGTH: 414 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..414

(ix) FEATURE:
        (A) NAME/KEY: sig_peptide
        (B) LOCATION: 1..57

(xi) SEQUENCE DESCRIPTION: SEQ ID NO:14:

ATG GMT TGG GTG TGG AMC TTG CTA TTC CTG ATG GCA GCT GCC CAA AGT    48
Met Xaa Trp Val Trp Xaa Leu Leu Phe Leu Met Ala Ala Ala Gln Ser
        -15             -10              -5

ATC CAA GCA CAG ATC CAG TTG GTG CAG TCT GGA CCT GAG CTG AAG AAG    96
Ile Gln Ala Gln Ile Gln Leu Val Gln Ser Gly Pro Glu Leu Lys Lys
    -1              5                   10

CCT GGA GAA ACA GTC AAG ATC TCC TGC AAG GCT TCT GGG TAT ACC TTC   144
Pro Gly Glu Thr Val Lys Ile Ser Cys Lys Ala Ser Gly Tyr Thr Phe
    15              20                  25

-continued

```
ACA AAC TAT GGA ATG AAC TGG GTG AAG CAG GCT CCA GGA AAG GGT TTA        192
Thr Asn Tyr Gly Met Asn Trp Val Lys Gln Ala Pro Gly Lys Gly Leu
 30                  35                  40                  45

AAG TGG ATG GGC TGG ATA AAC ACC AAG AGT GGA GAG CCA ACA TAT GCT        240
Lys Trp Met Gly Trp Ile Asn Thr Lys Ser Gly Glu Pro Thr Tyr Ala
                 50                  55                  60

GAA GAG TTC AAG GGA CGG TTT GCC TTC TCT TTG GAA ACC TCT GCC AGC        288
Glu Glu Phe Lys Gly Arg Phe Ala Phe Ser Leu Glu Thr Ser Ala Ser
             65                  70                  75

ACT GCC AAT TTG CAG ATC AAG AAC CTC AAA AAT GAG GAC ACG GCT ACA        336
Thr Ala Asn Leu Gln Ile Lys Asn Leu Lys Asn Glu Asp Thr Ala Thr
         80                  85                  90

TAT TTC TGT GCA AGA TGG GTA CCT GGG ACC TAT GCC ATG GAC TAC TGG        384
Tyr Phe Cys Ala Arg Trp Val Pro Gly Thr Tyr Ala Met Asp Tyr Trp
     95                 100                 105

GGT CAA GGA ACC TCA GTC ACC GTC TCC TCA                                414
Gly Gln Gly Thr Ser Val Thr Val Ser Ser
110                 115
```

(2) INFORMATION FOR SEQ ID NO:15:

(i) SEQUENCE CHARACTERISTICS:
        (A) LENGTH: 138 amino acids
        (B) TYPE: amino acid
        (D) TOPOLOGY: linear (ii) MOLECULE TYPE: protein (ix) FEATURE:
        (A) NAME/KEY: Modified-site
        (B) LOCATION: 2
        (C) OTHER INFORMATION: /note= "Can be Ala or Asp"

(ix) FEATURE:
        (A) NAME/KEY: Modified-site
        (B) LOCATION: 6
        (C) OTHER INFORMATION: /note= "Can be Asn or Thr"

(xi) SEQUENCE DESCRIPTION: SEQ ID NO:15:

```
Met Xaa Trp Val Trp Xaa Leu Leu Phe Leu Met Ala Ala Gln Ser
             -15                 -10                  -5

Ile Gln Ala Gln Ile Gln Leu Val Gln Ser Gly Pro Glu Leu Lys Lys
     -1                   5                  10

Pro Gly Glu Thr Val Lys Ile Ser Cys Lys Ala Ser Gly Tyr Thr Phe
 15                  20                  25

Thr Asn Tyr Gly Met Asn Trp Val Lys Gln Ala Pro Gly Lys Gly Leu
 30                  35                  40                  45

Lys Trp Met Gly Trp Ile Asn Thr Lys Ser Gly Glu Pro Thr Tyr Ala
                 50                  55                  60

Glu Glu Phe Lys Gly Arg Phe Ala Phe Ser Leu Glu Thr Ser Ala Ser
             65                  70                  75

Thr Ala Asn Leu Gln Ile Lys Asn Leu Lys Asn Glu Asp Thr Ala Thr
         80                  85                  90

Tyr Phe Cys Ala Arg Trp Val Pro Gly Thr Tyr Ala Met Asp Tyr Trp
     95                 100                 105

Gly Gln Gly Thr Ser Val Thr Val Ser Ser
110                 115
```

(2) INFORMATION FOR SEQ ID NO:16:

(i) SEQUENCE CHARACTERISTICS:
        (A) LENGTH: 411 base pairs
        (B) TYPE: nucleic acid

```
        (C) STRANDEDNESS: double
        (D) TOPOLOGY: linear (ii) MOLECULE TYPE: cDNA (ix) FEATURE:
        (A) NAME/KEY: CDS
        (B) LOCATION: 31..411

(ix) FEATURE:
        (A) NAME/KEY: sig_peptide
        (B) LOCATION: 31..90

(xi) SEQUENCE DESCRIPTION: SEQ ID NO:16:

ATTTAAATTG ATATCTCCTT AGGTCTCGAG ATG AGT GTG CTC ACT CAG GTC CTG          54
                                Met Ser Val Leu Thr Gln Val Leu
                                -20                 -15

GCG TTG CTG CTG CTG TGG CTT ACA GGT GCC AGA TGT GAC ATC CAG ATG          102
Ala Leu Leu Leu Leu Trp Leu Thr Gly Ala Arg Cys Asp Ile Gln Met
        -10                  -5                  1

ACT CAG TCT CCA TCC TCC CTA TCT GCA TCT GTG GGA GAC AGA GTC ACC          150
Thr Gln Ser Pro Ser Ser Leu Ser Ala Ser Val Gly Asp Arg Val Thr
  5                  10                  15                  20

ATC ACA TGT CGA GCA AGT GGG AAT ATT CAC AAT TAT TTA GCA TGG TAT          198
Ile Thr Cys Arg Ala Ser Gly Asn Ile His Asn Tyr Leu Ala Trp Tyr
              25                  30                  35

CAG CAG AAA CAG GGA AAA TCT CCT CAA CTC CTG GTC TAT AAT GCA AAA          246
Gln Gln Lys Gln Gly Lys Ser Pro Gln Leu Leu Val Tyr Asn Ala Lys
          40                  45                  50

ACC TTA GCA AGT GGT GTG CCA TCA AGG TTC AGT GGC AGT GGA TCA GGA          294
Thr Leu Ala Ser Gly Val Pro Ser Arg Phe Ser Gly Ser Gly Ser Gly
      55                  60                  65

ACA GAT TTT ACT CTC ACC ATC AGC AGC CTG CAG CCT GAA GAT TTT GGG          342
Thr Asp Phe Thr Leu Thr Ile Ser Ser Leu Gln Pro Glu Asp Phe Gly
  70                  75                  80

AGT CAT TAC TGT CAA CAT TTT TGG ACC ACT CCG TGG ACG TTC GGT GGA          390
Ser His Tyr Cys Gln His Phe Trp Thr Thr Pro Trp Thr Phe Gly Gly
 85                  90                  95                 100

GGC ACC AAG CTG GAA ATC AAA                                              411
Gly Thr Lys Leu Glu Ile Lys
                105

(2) INFORMATION FOR SEQ ID NO:17:

(i) SEQUENCE CHARACTERISTICS:
        (A) LENGTH: 127 amino acids
        (B) TYPE: amino acid
        (D) TOPOLOGY: linear (ii) MOLECULE TYPE: protein (xi) SEQUENCE DESCRIPTION: SEQ ID NO:17:

Met Ser Val Leu Thr Gln Val Leu Ala Leu Leu Leu Trp Leu Thr
-20                 -15                 -10                 -5

Gly Ala Arg Cys Asp Ile Gln Met Thr Gln Ser Pro Ser Ser Leu Ser
                  1                   5                  10

Ala Ser Val Gly Asp Arg Val Thr Ile Thr Cys Arg Ala Ser Gly Asn
             15                  20                  25

Ile His Asn Tyr Leu Ala Trp Tyr Gln Gln Lys Gln Gly Lys Ser Pro
         30                  35                  40

Gln Leu Leu Val Tyr Asn Ala Lys Thr Leu Ala Ser Gly Val Pro Ser
 45                  50                  55                  60

Arg Phe Ser Gly Ser Gly Ser Gly Thr Asp Phe Thr Leu Thr Ile Ser
```

```
                    65                  70                  75
Ser Leu Gln Pro Glu Asp Phe Gly Ser His Tyr Cys Gln His Phe Trp
                80                  85                  90

Thr Thr Pro Trp Thr Phe Gly Gly Gly Thr Lys Leu Glu Ile Lys
            95                  100                 105
```

(2) INFORMATION FOR SEQ ID NO:18:

(i) SEQUENCE CHARACTERISTICS:
        (A) LENGTH: 417 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..417

(ix) FEATURE:
        (A) NAME/KEY: sig_peptide
        (B) LOCATION: 1..60

(xi) SEQUENCE DESCRIPTION: SEQ ID NO:18:

```
ATG AGT GTG CTC ACT CAG GTC CTG GCG TTG CTG CTG CTG TGG CTT ACA        48
Met Ser Val Leu Thr Gln Val Leu Ala Leu Leu Leu Leu Trp Leu Thr
-20                 -15                 -10                 -5

GGT GCC AGA TGT CAG ATC CAG TTG GTG CAG TCT GGA TCT GAG CTG AAG        96
Gly Ala Arg Cys Gln Ile Gln Leu Val Gln Ser Gly Ser Glu Leu Lys
                1                   5                   10

AAG CCT GGA GCC TCA GTC AAG ATC TCC TGC AAG GCT TCT GGG TAT ACC       144
Lys Pro Gly Ala Ser Val Lys Ile Ser Cys Lys Ala Ser Gly Tyr Thr
            15                  20                  25

TTC ACA AAC TAT GGA ATG AAC TGG GTG CGA CAG GCT CCA GGA CAA GGT       192
Phe Thr Asn Tyr Gly Met Asn Trp Val Arg Gln Ala Pro Gly Gln Gly
        30                  35                  40

TTA GAG TGG ATG GGC TGG ATA AAC ACC AAG AGT GGA GAG CCA ACA TAT       240
Leu Glu Trp Met Gly Trp Ile Asn Thr Lys Ser Gly Glu Pro Thr Tyr
45                  50                  55                  60

GCT GAA GAG TTC AAG GGA CGG TTT GTC TTC TCT TTG GAC ACC TCT GTC       288
Ala Glu Glu Phe Lys Gly Arg Phe Val Phe Ser Leu Asp Thr Ser Val
                65                  70                  75

ACC ACT GCC TAT TTG CAG ATC AGC AGC CTC AAA GCT GAG GAC ACG GCT       336
Thr Thr Ala Tyr Leu Gln Ile Ser Ser Leu Lys Ala Glu Asp Thr Ala
            80                  85                  90

GTG TAT TTC TGT GCA AGA TGG GTA CCT GGG ACC TAT GCC ATG GAC TAC       384
Val Tyr Phe Cys Ala Arg Trp Val Pro Gly Thr Tyr Ala Met Asp Tyr
        95                  100                 105

TGG GGT CAA GGA ACC ACG GTC ACC GTC TCC TCA                            417
Trp Gly Gln Gly Thr Thr Val Thr Val Ser Ser
    110                 115
```

(2) INFORMATION FOR SEQ ID NO:19:

(i) SEQUENCE CHARACTERISTICS:
        (A) LENGTH: 139 amino acids
        (B) TYPE: amino acid
        (D) TOPOLOGY: linear (ii) MOLECULE TYPE: protein (xi) SEQUENCE DESCRIPTION: SEQ ID NO:19:

```
Met Ser Val Leu Thr Gln Val Leu Ala Leu Leu Leu Leu Trp Leu Thr
-20                 -15                 -10                 -5
```

```
Gly Ala Arg Cys Gln Ile Gln Leu Val Gln Ser Gly Ser Glu Leu Lys
            1               5                   10

Lys Pro Gly Ala Ser Val Lys Ile Ser Cys Lys Ala Ser Gly Tyr Thr
        15                  20                  25

Phe Thr Asn Tyr Gly Met Asn Trp Val Arg Gln Ala Pro Gly Gln Gly
        30                  35                  40

Leu Glu Trp Met Gly Trp Ile Asn Thr Lys Ser Gly Glu Pro Thr Tyr
45                  50                  55                  60

Ala Glu Glu Phe Lys Gly Arg Phe Val Phe Ser Leu Asp Thr Ser Val
                65                  70                  75

Thr Thr Ala Tyr Leu Gln Ile Ser Ser Leu Lys Ala Glu Asp Thr Ala
            80                  85                  90

Val Tyr Phe Cys Ala Arg Trp Val Pro Gly Thr Tyr Ala Met Asp Tyr
        95                  100                 105

Trp Gly Gln Gly Thr Thr Val Thr Val Ser Ser
        110                 115
```

(2) INFORMATION FOR SEQ ID NO:20:

(i) SEQUENCE CHARACTERISTICS:
        (A) LENGTH: 447 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 31..447

(ix) FEATURE:
        (A) NAME/KEY: sig_peptide
        (B) LOCATION: 31..90

(xi) SEQUENCE DESCRIPTION: SEQ ID NO:20:

```
CGATTGGAAT TCTTGCGGCC GCTTGCTAGC ATG AGT GTG CTC ACT CAG GTC CTG        54
                                Met Ser Val Leu Thr Gln Val Leu
                                    -20                 -15

GCG TTG CTG CTG CTG TGG CTT ACA GGT GCC AGA TGT CAG ATC CAG TTG        102
Ala Leu Leu Leu Leu Trp Leu Thr Gly Ala Arg Cys Gln Ile Gln Leu
    -10                 -5                  1

GTG CAG TCT GGA GCT GAG GTG AAG AAG CCT GGA GCC TCA GTC AAG ATC        150
Val Gln Ser Gly Ala Glu Val Lys Lys Pro Gly Ala Ser Val Lys Ile
 5                  10                  15                  20

TCC TGC AAG GCT TCT GGG TAT ACC TTC ACA AAC TAT GGA ATG AAC TGG        198
Ser Cys Lys Ala Ser Gly Tyr Thr Phe Thr Asn Tyr Gly Met Asn Trp
                25                  30                  35

GTG CGA CAG GCT CCA GGA CAA GGT TTA GAG TGG ATG GGC TGG ATA AAC        246
Val Arg Gln Ala Pro Gly Gln Gly Leu Glu Trp Met Gly Trp Ile Asn
            40                  45                  50

ACC AAG AGT GGA GAG CCA ACA TAT GCT GAA GAG TTC AAG GGA CGG TTT        294
Thr Lys Ser Gly Glu Pro Thr Tyr Ala Glu Glu Phe Lys Gly Arg Phe
        55                  60                  65

ACC TTC ACC TTG GAC ACC TCT ACG AGC ACT GCC TAT TTG GAG ATC AGG        342
Thr Phe Thr Leu Asp Thr Ser Thr Ser Thr Ala Tyr Leu Glu Ile Arg
    70                  75                  80

AGC CTC AGA TCT GAC GAC ACG GCT GTG TAT TTC TGT GCA AGA TGG GTA        390
Ser Leu Arg Ser Asp Asp Thr Ala Val Tyr Phe Cys Ala Arg Trp Val
85                  90                  95                  100

CCT GGG ACC TAT GCC ATG GAC TAC TGG GGT CAA GGA ACC ACG GTC ACC        438
```

```
Pro Gly Thr Tyr Ala Met Asp Tyr Trp Gly Gln Gly Thr Thr Val Thr
            105                 110                 115

GTC TCC TCA                                                                  447
Val Ser Ser
```

(2) INFORMATION FOR SEQ ID NO:21:

(i) SEQUENCE CHARACTERISTICS:
        (A) LENGTH: 139 amino acids
        (B) TYPE: amino acid
        (D) TOPOLOGY: linear (ii) MOLECULE TYPE: protein (xi) SEQUENCE DESCRIPTION: SEQ ID NO:21:

```
Met Ser Val Leu Thr Gln Val Leu Ala Leu Leu Leu Trp Leu Thr
-20             -15                 -10                 -5

Gly Ala Arg Cys Gln Ile Gln Leu Val Gln Ser Gly Ala Glu Val Lys
             1               5                  10

Lys Pro Gly Ala Ser Val Lys Ile Ser Cys Lys Ala Ser Gly Tyr Thr
        15                  20                  25

Phe Thr Asn Tyr Gly Met Asn Trp Val Arg Gln Ala Pro Gly Gln Gly
        30                  35                  40

Leu Glu Trp Met Gly Trp Ile Asn Thr Lys Ser Gly Glu Pro Thr Tyr
45                  50                  55                  60

Ala Glu Glu Phe Lys Gly Arg Phe Thr Phe Thr Leu Asp Thr Ser Thr
             65                  70                  75

Ser Thr Ala Tyr Leu Glu Ile Arg Ser Leu Arg Ser Asp Asp Thr Ala
            80                  85                  90

Val Tyr Phe Cys Ala Arg Trp Val Pro Gly Thr Tyr Ala Met Asp Tyr
            95                  100                 105

Trp Gly Gln Gly Thr Thr Val Thr Val Ser Ser
            110                 115
```

(2) INFORMATION FOR SEQ ID NO:22:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

```
NNNNNNGAAT TCACTGGATG GTGGGAAGAT GGA                                          33
```

(2) INFORMATION FOR SEQ ID NO:23:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

```
NNNNNNGAAT TCAYCTCCAC ACACAGGRRC CAGTGGATAG AC                                42
```

(2) INFORMATION FOR SEQ ID NO:24:

(i) SEQUENCE CHARACTERISTICS:

```
        (A) LENGTH: 40 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

ACTAGTCGAC ATGAGTGTGC TCACTCAGGT CCTGGSGTTG                             40

(2) INFORMATION FOR SEQ ID NO:25:

(i) SEQUENCE CHARACTERISTICS:
        (A) LENGTH: 88 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

TAGGGAGACC CAAGCTTGGT ACCAATTTAA ATTGATATCT CCTTAGGTCT CGAGTCTCTA       60

GATAACCGGT CAATCGATTG GGATTCTT                                         88

(2) INFORMATION FOR SEQ ID NO:26:

(i) SEQUENCE CHARACTERISTICS:
        (A) LENGTH: 88 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

GACACTATAG AATAGGGCCC TTCCGCGGTT GGATCCAACA CGTGAAGCTA GCAAGCGGCC       60

GCAAGAATTC CAATCGATTG ACCGGTTA                                         88

(2) INFORMATION FOR SEQ ID NO:27:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

GATCTGCTAG CCCGGGTGAC CTGAGGCGCG CCTTTGGCGC C                          41

(2) INFORMATION FOR SEQ ID NO:28:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

GATCGGCGCC AAAGGCGCGC CGCAGGTCAC CCGGGCTAGC A                          41

(2) INFORMATION FOR SEQ ID NO:29:

(i) SEQUENCE CHARACTERISTICS:
```

```
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

CCGGGCCTCT CAAAAAAGGG AAAAAAAGCA TG                                 32

(2) INFORMATION FOR SEQ ID NO:30:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

CTTTTTTTCC CTTTTTTGAG AGGC                                          24

(2) INFORMATION FOR SEQ ID NO:31:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

CGCGCCGGCT TCGAATAGCC AGAGTAACCT TTTTTTTTAA TTTTATTTTA TTTTATTTTT   60

GAGATGGAGT TTGG                                                    74

(2) INFORMATION FOR SEQ ID NO:32:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:32:

CGCCAAACTC CATCTCAAAA ATAAAATAAA ATAAAATTAA AAAAAAAGGT TACTCTGGCT   60

ATTCGAAGCC GG                                                      72

(2) INFORMATION FOR SEQ ID NO:33:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:33:

ATCGATGCTA GCACCAAGGG CCCA                                          24

(2) INFORMATION FOR SEQ ID NO:34:

(i) SEQUENCE CHARACTERISTICS:
```

(A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:34:

CTCGAGGGGT CACCACGCTG CTGA                                          24

(2) INFORMATION FOR SEQ ID NO:35:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:35:

AACAGCTATG ACCATGATTA C                                             21

(2) INFORMATION FOR SEQ ID NO:36:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:36:

CACCCAGCCT GTGCCTGCCT G                                             21

(2) INFORMATION FOR SEQ ID NO:37:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:37:

CGATTGGAAT TCTTGCGGCC GCTTGCTAGC                                    30

(2) INFORMATION FOR SEQ ID NO:38:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:38:

CTTGCGGCCG CTTGCTAGCA TGGATTGGGT GTGGAACTTG CTATTCCTGA TGGCAGCTGC    60

CCAAAGTATC CAAGCACAGA                                               80

(2) INFORMATION FOR SEQ ID NO:39:

(i) SEQUENCE CHARACTERISTICS:
        (A) LENGTH: 80 base pairs
        (B) TYPE: nucleic acid (C) STRANDEDNESS: single
        (D) TOPOLOGY: linear (ii) MOLECULE TYPE: cDNA (xi) SEQUENCE DESCRIPTION: SEQ ID NO:39:

CTTGACTGTT TCTCCAGGCT TCTTCAGCTC AGGTCCAGAC TGCACCAACT GGATCTGTGC    60

TTGGATACTT TGGGCAGCTG    80

(2) INFORMATION FOR SEQ ID NO:40:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:40:

CTGAAGAAGC CTGGAGAAAC AGTCAAGATC TCCTGCAAGG CTTCTGGGTA TACCTTCACA    60

AACTATGGAA TGAACTGGGT    80

(2) INFORMATION FOR SEQ ID NO:41:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:41:

TCTTGGTGTT TATCCAGCCC ATCCACTTTA AACCCTTTCC TGGAGCCTGC TTCACCCAGT    60

TCATTCCATA GTTTGTGAAG    80

(2) INFORMATION FOR SEQ ID NO:42:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:42:

AGTGGATGGG CTGGATAAAC ACCAAGAGTG GAGAGCCAAC ATATGCTGAA GAGTTCAAGG    60

GACGGTTTGC CTTCTCTTTG    80

(2) INFORMATION FOR SEQ ID NO:43:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:43:

TCCTCATTTT TGAGGTTCTT GATCTGCAAA TTGGCAGTGC TGGCAGAGGT TTCCAAAGAG    60

AAGGCAAACC GTCCCTTGAA    80

(2) INFORMATION FOR SEQ ID NO:44:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:44:

```
GCAGATCAAG AACCTCAAAA ATGAGGACAC GGCTACATAT TTCTGTGCAA GATGGGTACC      60

TGGGACCTAT GCCATGGACT                                                 80
```

(2) INFORMATION FOR SEQ ID NO:45:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:45:

```
TGGGCCCTTG GTGCTAGCTG AGGAGACGGT GACTGAGGTT CCTTGACCCC AGTAGTCCAT      60

GGCATAGGTC CCAGGTACCC                                                 80
```

(2) INFORMATION FOR SEQ ID NO:46:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:46:

```
GGGAAGACGG ATGGGCCCTT GGTGCTAGC                                       29
```

(2) INFORMATION FOR SEQ ID NO:47:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:47:

```
ATTTAAATTG ATATCTCCTT AGGTCTCGAG                                      30
```

(2) INFORMATION FOR SEQ ID NO:48:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:48:

```
ATTTAAATTG ATATCTCCTT AGGTCTCGAG ATGAGTGTGC TCACTCAGGT CCTGGCGTTG      60
```

```
CTGCTGCTGT GGCTTACAG                                                        79

(2) INFORMATION FOR SEQ ID NO:49:

(i) SEQUENCE CHARACTERISTICS:
         (A) LENGTH: 78 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:49:

AGATGCAGAT AGGGAGGCTG GAGACTGAGT CATCTGGATG TCACATCTGG CACCTGTAAG        60

CCACAGCAGC AGCAACGC                                                       78

(2) INFORMATION FOR SEQ ID NO:50:

(i) SEQUENCE CHARACTERISTICS:
         (A) LENGTH: 78 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:50:

GTCTCCAGCC TCCCTATCTG CATCTGTGGG AGAAACTGTC ACCATCACAT GTCGAGCAAG        60

TGGGAATATT CACAATTA                                                       78

(2) INFORMATION FOR SEQ ID NO:51:

(i) SEQUENCE CHARACTERISTICS:
         (A) LENGTH: 78 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:51:

TATAGACCAG GAGCTGAGGA GATTTTCCCT GTTTCTGCTG ATACCATGCT AAATAATTGT        60

GAATATTCCC ACTTGCTC                                                       78

(2) INFORMATION FOR SEQ ID NO:52:

(i) SEQUENCE CHARACTERISTICS:
         (A) LENGTH: 78 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:52:

AAATCTCCTC AGCTCCTGGT CTATAATGCA AAAACCTTAG CAGATGGTGT GCCATCAAGG        60

TTCAGTGGCA GTGGATCA                                                       78

(2) INFORMATION FOR SEQ ID NO:53:

(i) SEQUENCE CHARACTERISTICS:
         (A) LENGTH: 78 base pairs
         (B) TYPE: nucleic acid
         (C) STRANDEDNESS: single
         (D) TOPOLOGY: linear
```

(ii) MOLECULE TYPE: cDNA (xi) SEQUENCE DESCRIPTION: SEQ ID NO:53:

CTCCCAAAAT CTTCAGGCTG CAGGCTGTTG ATCCTGAGAG AAAATTGTGT TCCTGATCCA     60

CTGCCACTGA ACCTTGAT     78

(2) INFORMATION FOR SEQ ID NO:54:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:54:

GCCTGCAGCC TGAAGATTTT GGGAGTCATT ACTGTCAACA TTTTTGGACC ACTCCGTGGA     60

CGTTCGGTGG AGGCACCA     78

(2) INFORMATION FOR SEQ ID NO:55:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:55:

TTCCAATCGA TTGACCGGTT ATCTAGAGAC TCGAGACTTA CGTTTGATTT CCAGCTTGGT     60

GCCTCCACCG AACGTCCACG G     81

(2) INFORMATION FOR SEQ ID NO:56:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:56:

TCGATTGACC GGTTATCTAG AGACTCGAGA     30

(2) INFORMATION FOR SEQ ID NO:57:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:57:

CTTGCGGCCG CTTGCTAGCA TGAGTGTGCT CACTCAGGTC CTGGCGTTGC TGCTGCTGTG     60

GCTTACAGGT GCCAGATGTC     80

(2) INFORMATION FOR SEQ ID NO:58:

(i) SEQUENCE CHARACTERISTICS:
        (A) LENGTH: 80 base pairs

```
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:58:

GACTGAGGCT CCAGGCTTCT TCAGCTCAGA TCCAGACTGC ACCAACTGGA TCTGACATCT    60

GGCACCTGTA AGCCACAGCA                                                80

(2) INFORMATION FOR SEQ ID NO:59:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:59:

GAGCTGAAGA AGCCTGGAGC CTCAGTCAAG ATCTCCTGCA AGGCTTCTGG GTATACCTTC    60

ACAAACTATG GAATGAACTG                                                80

(2) INFORMATION FOR SEQ ID NO:60:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:60:

TGGTGTTTAT CCAGCCCATC CACTCTAAAC CTTGTCCTGG AGCCTGTCGC ACCCAGTTCA    60

TTCCATAGTT TGTGAAGGTA                                                80

(2) INFORMATION FOR SEQ ID NO:61:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:61:

TAGAGTGGAT GGGCTGGATA AACACCAAGA GTGGAGAGCC AACATATGCT GAAGAGTTCA    60

AGGGACGGTT TGTCTTCTCT                                                80

(2) INFORMATION FOR SEQ ID NO:62:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:62:

TCAGCTTTGA GGCTGCTGAT CTGCAAATAG GCAGTGCTGA CAGAGGTGTC CAAAGAGAAG    60

ACAAACCGTC CCTTGAACTC                                                80
```

(2) INFORMATION FOR SEQ ID NO:63:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:63:

```
TTTGCAGATC AGCAGCCTCA AAGCTGAGGA CACGGCTGTG TATTTCTGTG CAAGATGGGT      60

ACCTGGGACC TATGCCATGG                                                  80
```

(2) INFORMATION FOR SEQ ID NO:64:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:64:

```
GCCCTTGGTG CTAGCTGAGG AGACGGTGAC CGTGGTTCCT TGACCCCAGT AGTCCATGGC      60

ATAGGTCCCA GGTACCCATC                                                  80
```

(2) INFORMATION FOR SEQ ID NO:65:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:65:

```
TGCTGTGGCT TACAGGTGCC AGATGTCAGA TCCAGTTGGT GCAGTCTGGA GCTGAGGTGA      60

AGAAGCCTGG AGCCTCAGTC                                                  80
```

(2) INFORMATION FOR SEQ ID NO:66:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:66:

```
TAGAGTGGAT GGGCTGGATA AACACCAAGA GTGGAGAGCC AACATATGCT GAAGAGTTCA      60

AGGGACGGTT TACCTTCACC                                                  80
```

(2) INFORMATION FOR SEQ ID NO:67:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:67:

TCAGATCTGA GGCTCCTGAT CTCCAAATAG GCAGTGCTCG TAGAGGTGTC CAAGGTGAAG      60

GTAAACCGTC CCTTGAACTC      80

(2) INFORMATION FOR SEQ ID NO:68:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:68:

TTTGGAGATC AGGAGCCTCA GATCTGACGA CACGGCTGTG TATTTCTGTG CAAGATGGGT      60

ACCTGGGACC TATGCCATGG      80

(2) INFORMATION FOR SEQ ID NO:69:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:69:

AGATGCAGAT AGGGAGGATG GAGACTGAGT CATCTGGATG TCACATCTGG CACCTGTAAG      60

CCACAGCAGC AGCAACGC      78

(2) INFORMATION FOR SEQ ID NO:70:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:70:

GTCTCCATCC TCCCTATCTG CATCTGTGGG AGACAGAGTC ACCATCACAT GTCGAGCAAG      60

TGGGAATATT CACAATTA      78

(2) INFORMATION FOR SEQ ID NO:71:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:71:

AAATCTCCTC AACTCCTGGT CTATAATGCA AAAACCTTAG CAAGTGGTGT GCCATCAAGG      60

TTCAGTGGCA GTGGATCA      78

(2) INFORMATION FOR SEQ ID NO:72:

(i) SEQUENCE CHARACTERISTICS:

(A) LENGTH: 78 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:72:

CTCCCAAAAT CTTCAGGCTG CAGGCTGCTG ATGGTGAGAG TAAAATCTGT TCCTGATCCA      60

CTGCCACTGA ACCTTGAT      78

(2) INFORMATION FOR SEQ ID NO:73:

(i) SEQUENCE CHARACTERISTICS:
        (A) LENGTH: 18 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:73:

Tyr Pro Arg Ser Ile Tyr Ile Arg Arg Arg His Pro Ser Pro Ser Leu
1               5                   10                  15

Thr Thr (2) INFORMATION FOR SEQ ID NO:74:

(i) SEQUENCE CHARACTERISTICS:
        (A) LENGTH: 15 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:74:

Gly Gly Ser Gly Ser Gly Gly Ser Gly Ser Gly Gly Ser Gly Ser
1               5                   10                  15

(2) INFORMATION FOR SEQ ID NO:75:

(i) SEQUENCE CHARACTERISTICS:
        (A) LENGTH: 107 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:75:

Asp Ile Gln Met Thr Gln Ser Pro Ala Ser Leu Ser Ala Ser Val Gly
1               5                   10                  15

Glu Thr Val Thr Xaa Thr Cys Arg Ala Ser Gly Asn Ile His Asn Tyr
                20                  25                  30

Leu Ala Trp Tyr Gln Gln Lys Gln Gly Lys Ser Pro Gln Leu Leu Val
            35                  40                  45

Tyr Asn Ala Xaa Thr Leu Ala Asp Gly Val Pro Ser Arg Phe Ser Gly
        50                  55                  60

Ser Gly Ser Gly Thr Gln Xaa Ser Leu Xaa Ile Asn Ser Leu Gln Pro
65                  70                  75                  80

Glu Asp Phe Gly Ser Xaa Tyr Cys Gln His Phe Trp Xaa Xaa Pro Trp
                85                  90                  95

Thr Phe Gly Gly Gly Thr Lys Leu Glu Ile Lys (2) INFORMATION FOR SEQ ID NO:76:

(i) SEQUENCE CHARACTERISTICS:
        (A) LENGTH: 107 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:76:

```
Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Phe Ser Leu Xaa Ile Asn Ser Leu Gln Pro
65                  70                  75                  80

Glu Asp Phe Gly Ser His Tyr Cys Gln His Phe Trp Thr Thr Pro Trp
                85                  90                  95

Thr Phe Gly Gly Gly Thr Lys Leu Glu Ile Lys
                100                 105
```

(2) INFORMATION FOR SEQ ID NO:77:

(i) SEQUENCE CHARACTERISTICS:
        (A) LENGTH: 107 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:77:

```
Asp Ile Gln Met Thr Gln Ser Pro Xaa Ser Leu Ser Ala Ser Val Gly
1               5                   10                  15

Xaa Xaa Val Thr Xaa Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Xaa Thr Leu Ala Xaa Gly Val Pro Ser Arg Phe Ser Gly
    50                  55                  60

Ser Gly Ser Gly Thr Xaa Xaa Xaa Leu Xaa Ile Xaa Ser Leu Gln Pro
65                  70                  75                  80

Glu Asp Phe Gly Ser Xaa Tyr Cys Gln His Phe Trp Xaa Xaa Pro Trp
                85                  90                  95

Thr Phe Gly Gly Gly Thr Lys Leu Glu Ile Lys
                100                 105
```

(2) INFORMATION FOR SEQ ID NO:78:

(i) SEQUENCE CHARACTERISTICS:
        (A) LENGTH: 119 amino acids
        (B) TYPE: amino acid
        (C) STRANDEDNESS: single
        (D) TOPOLOGY: linear (ii) MOLECULE TYPE: cDNA (xi) SEQUENCE DESCRIPTION: SEQ ID NO:78:

Gln Ile Gln Leu Val Gln Ser Gly Xaa Glu Xaa Lys Lys Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Lys Ser Gly Glu Pro Thr Tyr Ala Glu Glu Phe
    50                  55                  60

Lys Gly Arg Phe Xaa Phe Xaa Leu Asp Thr Ser Xaa Ser Thr Ala Tyr
65                  70                  75                  80

Leu Xaa Ile Xaa Ser Leu Xaa Xaa Xaa Asp Thr Ala Val Tyr Phe Cys
            85                  90                  95

Ala Arg Trp Val Pro Gly Thr Tyr Ala Met Asp Tyr Trp Gly Gln Gly
            100                 105                 110

Thr Thr Val Thr Val Ser Ser
            115

(2) INFORMATION FOR SEQ ID NO:79:

(i) SEQUENCE CHARACTERISTICS:
        (A) LENGTH: 119 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:79:

Gln Ile Gln Leu Val Gln Ser Gly Pro Glu Leu Lys Lys Pro Gly Glu
1               5                   10                  15

Thr Val Lys Ile Ser Cys Xaa Ala Ser Gly Tyr Thr Phe Thr Xaa Tyr
            20                  25                  30

Gly Met Asn Trp Val Lys Gln Ala Pro Gly Lys Gly Leu Lys Trp Met
        35                  40                  45

Gly Trp Ile Asn Thr Xaa Ser Gly Glu Pro Thr Tyr Ala Glu Glu Phe
    50                  55                  60

Lys Gly Arg Phe Xaa Phe Ser Leu Glu Thr Ser Ala Ser Thr Ala Xaa
65                  70                  75                  80

Leu Gln Ile Xaa Asn Xaa Xaa Asn Glu Asp Xaa Ala Thr Tyr Phe Cys
            85                  90                  95

Ala Arg Trp Val Pro Gly Thr Tyr Ala Met Asp Tyr Trp Gly Gln Gly
            100                 105                 110

Thr Ser Val Thr Val Ser Ser
            115

(2) INFORMATION FOR SEQ ID NO:80:

(i) SEQUENCE CHARACTERISTICS:
        (A) LENGTH: 119 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:80:

Gln Ile Gln Leu Val Gln Ser Gly Pro Glu Leu Lys Lys Pro Gly Glu

-continued

```
1               5               10              15
Thr Val Lys Ile Ser Cys Xaa Ala Ser Gly Tyr Thr Phe Thr Asn Tyr
            20              25              30

Gly Met Asn Trp Val Lys Gln Ala Pro Gly Lys Gly Leu Lys Trp Met
        35              40              45

Gly Trp Ile Asn Thr Lys Ser Gly Glu Pro Thr Tyr Ala Glu Glu Phe
    50              55              60

Lys Gly Arg Phe Xaa Phe Ser Leu Glu Thr Ser Ala Ser Thr Ala Xaa
65              70              75              80

Leu Gln Ile Lys Asn Xaa Xaa Asn Glu Asp Thr Ala Thr Tyr Phe Cys
            85              90              95

Ala Arg Trp Val Pro Gly Thr Tyr Ala Met Asp Tyr Trp Gly Gln Gly
        100             105             110

Thr Ser Val Thr Val Ser Ser
        115
```

(2) INFORMATION FOR SEQ ID NO:81:

(i) SEQUENCE CHARACTERISTICS:
        (A) LENGTH: 119 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:81:

```
Gln Ile Gln Leu Val Gln Ser Gly Xaa Glu Xaa Lys Lys Pro Gly Xaa
1               5               10              15

Xaa Val Lys Ile Ser Cys Xaa Ala Ser Gly Tyr Thr Phe Thr Xaa Tyr
            20              25              30

Gly Met Asn Trp Val Xaa Gln Ala Pro Gly Xaa Gly Leu Xaa Trp Met
        35              40              45

Gly Trp Ile Asn Thr Xaa Ser Gly Glu Pro Thr Tyr Ala Glu Glu Phe
    50              55              60

Lys Gly Arg Phe Xaa Phe Xaa Leu Xaa Thr Ser Xaa Ser Thr Ala Xaa
65              70              75              80

Leu Xaa Ile Xaa Xaa Xaa Xaa Xaa Asp Xaa Ala Xaa Tyr Phe Cys
            85              90              95

Ala Arg Trp Val Pro Gly Thr Tyr Ala Met Asp Tyr Trp Gly Gln Gly
        100             105             110

Thr Xaa Val Thr Val Ser Ser
        115
```

1

COMPOSITION AND METHOD FOR ENHANCING FIBRINOLYSIS

CROSS-REFERENCE TO RELATED APPLICATIONS

This application claims priority benefit to U.S. appl. Ser. No. 60/026,356, filed Sep. 20, 1996, which disclosure is hereby incorporated by reference.

BACKGROUND OF THE INVENTION

Statement as to Rights to Inventions Made Under Federally-Sponsored Research and Development This invention was made in part with Government support under Contract #HL-02348 awarded by the National Institutes of Health. The Government has certain rights in this invention.

FIELD OF THE INVENTION

The present invention relates to a composition and method of treatment for pulmonary embolism, myocardial infarction, thrombosis, and stroke in a patient, and more specifically to a therapy which enhances fibrinolysis comprising administering an alpha-2-antiplasmin-binding molecule. The invention also relates to a treatment for enhancing fibrinolysis comprising administering an alpha-2-antiplasmin-binding molecule together with a thrombolytic agent.

DESCRIPTION OF BACKGROUND ART

Venous thrombosis and pulmonary embolism are major causes of morbidity and mortality in the United States, accounting for about 270,000 hospitalizations a year (Anderson, F. A., Jr. et al., *Arch. Intern. Med.* 151:933–938 (1991)). In addition, it is estimated that about 50,000–200,000 patients a year die from pulmonary embolism (Lilienfeld, D. E. et al., *Chest* 98:1067–1072 (1990)). In surprising contrast with the mortality rate for myocardial infarction, the mortality rate for pulmonary embolism (estimated at 9.2% in treated patients) has not improved in the last 30 years (Lilienfeld, D. E. et al., *Chest* 98:1067–1072 (1990); Giuntini, C. et al., *Chest* 107:3S–9S (1995)). Moreover, survivors of venous thromboembolism are known to be at risk for recurrent thrombosis, postphlebitic syndrome, and pulmonary hypertension (Sutton, G. C. et al., *Br. Heart J.* 39:1135–1192 (1977); Salzman, E. W. and Hirsch J., "The Epidemiology, Pathogenesis and Natural History of Venous Thrombosis," in *Hemostasis and Thrombosis: Basic Principles and Clinical Practice,* Coleman, R. W. et al., eds., 3rd ed. Philadelphia, Pa. (1994), pp. 1275–1296).

A. Mechanism of Clot Formation and Lysis

Clots (or thrombi in a patient) are composed of fibrin and blood platelets in various ratios. The fundamental reaction in blood clotting involves the conversion of a soluble plasma protein (fibrinogen) into insoluble fibrin. The conversion of fibrinogen into fibrin is catalyzed by the enzyme, thrombin, which is a serine protease.

Clot lysis is mediated by plasmin. Under natural conditions, plasminogen is converted to plasmin by plasminogen activators. Natural plasmin inhibitors include $\alpha$2-antiplasmin, $\alpha$2-macroglobulin and $\alpha$-1-antitrypsin, all glycoproteins. Alpha-2-antiplasmin has a much higher affinity for plasmin than $\alpha$2-macroglobulin and binds specifically to plasmin in a 1:1 ratio. The larger pool of $\alpha$-macroglobulin acts as a reservoir inhibitor (Kane K. K., *Ann. Clin. Lab. Sci.* 14:443–449 (1984)). Thus, clot lysis by the administration of t-PA is limited by the rapid and irreversible inactivation of plasmin by plasmin inhibitors.

B. Treatment for Venous Thrombosis and Pulmonary Embolism

Standard therapy for venous thromboembolism is heparin, which potentiates thrombin and factor Xa inhibition by antithrombin III (Goldhaber, S., *Chest* 107:45S–51S (1995)). Although heparin decreases new thrombus (clot) S formation, clinical studies suggest that there is little early endogenous lysis of the large thrombi that often exist at the time of diagnosis in patients with venous thromboembolism (Goldhaber, S. Z. et al., *Lancet* 2:886–889 (1986); "The Urokinase Pulmonary Embolism Trial," *Circulation* 47:1–108 (1973); Goldhaber, S. Z. et al., *Am. J. Med.* 88:235–240 (1990); Goldhaber, S. Z. et al., *Lancet* 341:507–511 (1993)). Since large thrombi are associated with an increase in morbidity and mortality, several studies have examined the effects of plasminogen activators in patients with venous thromboembolism (Goldhaber, S. Z. et al., *Lancet* 2:886–889 (1986); "The Urokinase Pulmonary Embolism Trial," *Circulation* 47:1–108 (1973); Goldhaber, S. Z. et al., *Am. J Med* 88:235–240 (1990); Goldhaber, S. Z. et al., *Lancet* 341:507–511(1993)).

Compared with heparin alone, plasminogen activators cause significant increases in the lysis of venous thromboemboli, but patients are frequently left with large amounts of residual thrombi in the lungs or deep veins immediately after therapy (Goldhaber, S. Z. et al., *Lancet* 2:886–889 (1986); "The Urokinase Pulmonary Embolism Trial," *Circulation* 47:1–108 (1973); Goldhaber, S. Z. et al., *Am. J. Med.* 88:235–240 (1990); Goldhaber, S. Z. et al., *Lancet* 341:507–511 (1993)). None of the randomized, controlled trials of patients with pulmonary embolism have demonstrated a mortality benefit from plasminogen activators, although this may well be due to the small numbers of patients enrolled in these studies. Use of plasminogen activators for myocardial infarctions has shown that 45–70% of patients with coronary thrombosis have failed to achieve full 90 minutes reperfusion with these agents.

Why venous thromboemboli resist fibrinolysis is unknown. Physical characteristics such as size, retraction, exposure to blood flow, and age may affect the lysis of these large fibrin-rich thrombi (Prewitt, R. M., *Chest* 99:157S–164S (1991)). However, it is also likely that the fibrinolytic resistance of these thrombi is regulated by specific molecular factors such as factor XIII, plasminogen activator inhibitor 1 (PAI-1), and alpha-2-antiplasmin ($\alpha$2AP) (Collen, D., *Eur. J. Biochem.* 69:209–216 (1976); Moroi, M. and Aoki, N., *J. Biol. Chem.* 251:5956–5965 (1976); Mullertz, S. and Clemmensen, I., *Biochem. J.* 159:545–553 (1976); Sakata, Y. and Aoki, N., *J. Clin. Invest.* 69:536–542 (1982); Robbie, L. A. et al., *Thromb. Haemostas.* 70:301–306 (1993); Francis, C. W. and Marder, V. J., *J. Clin. Invest.* 80:1459–1465 (1987); Jansen, J. W. C. M. et al., *Thromb. Haemostas.* 57:171–175 (1987); Reed, G. L. et al., *Trans. Assoc. Am. Phys.* 104:21–28 (1991); Stringer, H. A. and Pannekoek, H., *J. Biol. Chem.* 270:11205–11208 (1995); Carmeliet, P. et al., *J. Clin. Invest.* 92:2756–2760 (1993); Lang, I. M. et al., *Circulation* 89:2715–2721 (1994); Marsh, J. J. et al., *Circulation* 90:3091–3097 (1994)).

Because $\alpha$2AP is an ultrafast covalent inhibitor of plasmin (the enzyme that degrades thrombi), $\alpha$2AP is a particularly likely cause of thrombus resistance (Collen, D., *Eur. J. Biochem.* 69:209–216 (1976); Moroi, M. and Aoki, N., *J.*

*Biol. Chem.* 251:5956–5965 (1976); Mullertz, S. and Clemmensen, I., *Biochem. J.* 159:545–553 (1976)). Moreover, α2AP is the only fibrinolytic inhibitor that is covalently crosslinked to the fibrin surface (Sakata, Y. and Aoki, N., *J. Clin. Invest.* 69:536–542 (1982)). This crosslinking (by activated factor XIII) concentrates α2AP on the fibrin surface, where it inhibits the initiation of fibrinolysis (Sakata, Y. and Aoki, N., *J. Clin. Invest.* 69:536–542 (1982)). Previous in vitro studies have shown that clots from α2AP-deficient patients lyse spontaneously, suggesting that α2AP plays a critical role in thrombus resistance to endogenous plasminogen activators (Aoki, N. et al., *Blood* 62:1118–1122 (1983); Miles, L. A. et al., *Blood* 59:1246–1251 (1982)). These observations led to the hypothesis that α2AP is a molecular mediator of the thrombus resistance seen in patients with pulmonary embolism. To test this hypothesis, we generated a specific inhibitor of α2AP and used it to determine the role played by α2AP in the regulation of lysis of experimental pulmonary emboli.

If an individual has formed a fibrin clot (thrombus) prior to the availability of medical assistance, the clot may be dissolved through the use of agents capable of lysing the fibrin thrombus, and thereby permitting blood to again flow through the affected blood vessel. Such agents include plasmin, anti-coagulants (such as, for example, heparin, hirudin and activated protein C), plasminogen activators (such as, for example, streptokinase, prourokinase, urokinase, tissue-type plasminogen activator, staphylokinase, and vampire bat plasminogen activator), and other such agents (Ganz, W. et al., *J. Amer. Coll. Cardiol.* 1:1247–1253 (1983); Rentrop, K. P. et al., *Amer. J. Cardiol.* 54:29E–31E (1984); Gold, H. K. et al., *Amer. J. Cardiol.* 53:122C–125C (1984)).

At present, treatment of pulmonary embolism, myocardial infarction, thrombosis, and stroke is partially achieved through the administration of thrombolytic agents. Use of such agents in therapy often results in incomplete lysis, and promotes the reformation of thrombi and reocclusion of the affected blood vessels. Hence, a need exists for an improvement in thrombolytic therapy which enhances fibrinolysis, while minimizing fibrinogen breakdown and preventing reformation of thrombi.

C. Alpha-2 antiplasmin Antibodies

Alpha-2-antiplasmin (α2AP) has three functional domains: the reactive site for plasmin, the plasmin(ogen) or LBS-binding site [complementary to the LBS (lysine-binding site) of plasmin(ogen)], and the crosslinking site for fibrin. Mimuro, J. et al., *Blood* 69:446–453 (1987). Mimuro et al. discloses antibodies to α2AP, one of which (JPTI-1) was specific to the reactive site of α2AP and prevented formation of α2AP complexes, thereby inhibiting antiplasmin activity. However, Mimuro et al. does not teach administration of the JPTI-1 antibody to enhance clot lysis. Other antibodies specific for α2AP are taught by Plow, E. F. et al., *J. Biol. Chem.* 255:2902–2906 (1980); Wimen, B. et al., *Scan. J. Clin. Lab. Invest.* 43:27–33 (1983); Hattey, E. et al., *Thromb. Res.* 45:485–495 (1987); Collen, U.S. Pat. No. 4,346,029 (1980); and Collen, U.S. Pat. No. 4,198,335 (1980).

SUMMARY OF THE INVENTION

The present invention relates to an improved thrombolytic therapy for the treatment of pulmonary embolism, myocardial infarction, thrombosis and stroke in patients. The invention is directed to an immunologic molecule capable of binding to both (1) human and nonhuman circulating α2-antiplasmins and (2) human and nonhuman fibrin crosslinked α2-antiplasmins. In preferred embodiments, the immunologic molecule is a chimeric antibody, a humanized antibody, or a single chain antibody. The invention is also directed to a method for treating pulmonary embolism, myocardial infarction, thrombosis and stroke in a patient comprising administering an α2-antiplasmin-binding molecule capable of binding to both (1) human and nonhuman circulating α2-antiplasmins and (2) human and nonhuman fibrin crosslinked a2-antiplasmins. The invention further provides a method of treatment for pulmonary embolism, myocardial infarction, thrombosis and stroke in a patient which comprises co-administrating to a patient in need of such treatment:

(a) a therapeutically effective amount of an immunologic molecule capable of binding to both (1) human and nonhuman circulating α2-antiplasmins and (2) human and nonhuman fibrin crosslinked α2-antiplasmins; and (b) a therapeutically effective amount of a thrombolytic agent, wherein the immunologic molecule (a) is different from the thrombolytic agent (b), thereby treating the patient.

The invention provides a monoclonal antibody or fragment thereof wherein the monoclonal antibody is capable of binding to both (1) human and nonhuman circulating α2-antiplasmins and (2) human and nonhuman fibrin crosslinked α2-antiplasmins. In one embodiment, the invention is monoclonal antibody 77A3. In another embodiment, the invention is monoclonal antibody 49C9. In another embodiment, the monoclonal antibody is 70B11.

The invention also provides a method of making the monoclonal antibody comprising:

(a) immunizing an animal with α2-antiplasmin or fragment thereof;

(b) fusing cells from the animal with tumor cells to make a hybridoma cell line;

(c) cloning the hybridoma cell line;

(d) selecting for the monoclonal antibody capable of binding to both (1) human and nonhuman circulating α2-antiplasmins and (2) human and nonhuman fibrin crosslinked α2-antiplasmins; and (e) obtaining the monoclonal antibody.

The invention provides a hybridoma cell line which produces the monoclonal antibody capable of binding to both (1) human and nonhuman circulating α2-antiplasmins and (2) human and nonhuman fibrin crosslinked α2-antiplasmins. In one embodiment, the invention is hybridoma cell line 77A3 (ATCC Accession No. HB-12192; Deposited at the American Type Culture Collection, 12301 Parklawn Drive, Rockville, Md., 20862 on Sep. 20, 1996).

The invention is directed to a method of making the hybridoma cell line comprising:

(a) immunizing an animal with α2-antiplasmin or fragment thereof;

(b) fusing the cells from the animal with tumor cells to make the hybridoma cell line; and (c) obtaining the hybridoma cell line which produces the monoclonal antibody capable of binding to both (1) human and nonhuman circulating α2-antiplasmins and (2) human and nonhuman fibrin crosslinked α2-antiplasmins.

The invention also provides a method for treating a number of diseases and conditions, including pulmonary embolism, myocardial infarction, thrombosis and stroke in a patient comprising administering a therapeutically effective amount of an immunologic molecule which is capable of binding to both (1) human and nonhuman circulating α2-antiplasmins and (2) human and nonhuman fibrin crosslinked α2-antiplasmins, thereby treating the patient.

S The invention further provides a method of treatment for pulmonary embolism, myocardial infarction, thrombosis or stroke in a patient which comprises co-administering to a patient in need of such treatment:

(a) a therapeutically effective amount of an immunologic molecule which is capable of binding to both (1) human and nonhuman circulating α2-antiplasmins and (2) human and nonhuman fibrin crosslinked α2-antiplasmins; and (b) a therapeutically effective amount of a thrombolytic agent, wherein the immunologic molecule (a) is different from the thrombolytic agent (b), thereby treating the patient.

In preferred embodiments, the thrombolytic agent is plasmin, anti-coagulant, or plasminogen activator. In one embodiment, the anti-coagulant is selected from the group consisting of heparin, hirudin and activated protein C. In another embodiment, the plasminogen activator is selected from the group consisting of staphylokinase, streptokinase, prourokinase, urokinase, tissue-type plasminogen activator, and vampire bat plasminogen activator.

Other embodiments of the invention include, the immunologic molecule provided to the patient by an intravenous infusion, by an intravenously injected bolus, or with a first bolus containing the immunologic molecule (a) and a subsequently administered second bolus containing the thrombolytic agent (b). Further embodiments include, the immunologic molecule (a) provided to the patient at a dose of between 3 to 300 nmole per kg of patient weight; and the thrombolytic agent (b) provided to the patient at a dose of between 0.01 to 3.0 mg per kg of patient weight.

The invention provides a kit useful for carrying out the method of treatment for pulmonary embolism, myocardial infarction, thrombosis or stroke in a patient, being compartmentalized in close confinement to receive two or more container means therein, which comprises:

(1) a first container containing a therapeutically effective amount of the immunologic molecule (a); and (2) a second container containing a therapeutically effective amount of the thrombolytic agent (b), wherein the immunologic molecule (a) is different from the thrombolytic agent (b).

The invention also provides nucleic acid molecules encoding immunologic molecules capable of binding to both (1) human and nonhuman circulating α2-antiplasmins and (2) human and nonhuman fibrin crosslinked α2-antiplasmins. Also provided are molecules comprising an amino acid sequence of the binding region of an immunologic molecule described herein.

BRIEF DESCRIPTION OF THE FIGURES

FIG. 10. The peptide sequences of the amino terminus of purified light chains from 49C9 (SEQ ID NO:1), 70B11 (SEQ ID NO:2) and 77A3 (SEQ ID NO:3) are shown.

FIG. 11. The cDNA sequence (SEQ ID NO:4) and corresponding deduced amino acid sequence of the signal peptide (amino acids −20 to −1 of SEQ ID NO:5) and light chain variable regions (amino acids 1 to 107 of SEQ ID NO:5) of 49C9 are shown.

FIG. 12. The cDNA sequence (SEQ ID NO:6) and corresponding deduced amino acid sequence of the signal peptide (amino acids −20 to −1 of SEQ ID NO:7) and light chain variable regions (amino acids 1 to 107 of SEQ ID NO:7) of 70B11 are shown.

FIG. 13. The cDNA sequence (SEQ ID NO:8) and corresponding deduced amino acid sequence of the signal peptide (amino acids −20 to −1 of SEQ ID NO:9) and light chain variable regions (amino acids 1 to 107 of SEQ ID NO:9) of 77A3 are shown.

FIG. 14. The cDNA sequence (SEQ ID NO:10) and corresponding deduced amino acid sequence of the signal peptide (amino acids −19 to −1 of SEQ ID NO:11) and heavy chain variable regions (amino acids 1–119 of SEQ ID NO:11) of 49C9 are shown.

FIG. 15. The cDNA sequence (SEQ ID NO:12) and corresponding deduced amino acid sequence of the signal peptide (amino acids −19 to −1 of SEQ ID NO:13) and heavy chain variable regions (amino acids 1–119 of SEQ ID NO:13) of 70B11 are shown.

FIG. 16. The cDNA sequence (SEQ ID NO:14) and corresponding deduced amino acid sequence of the signal peptide (amino acids −19 to −1 of SEQ ID NO:15) and heavy chain variable regions (amino acids 1–119 of SEQ ID NO:15) of 77A3 are shown.

FIGS. 17A–B. The cDNA sequence (SEQ ID NO:16) and corresponding amino acid sequence (SEQ ID NO:17) of humanized77A3-1 and humanized 77A3-2 light chain. Positions falling within the CDR loops are shown enclosed within the boxes with solid borders.

FIGS. 18A–B. The cDNA sequence (SEQ ID NO:18) and corresponding amino acid sequence (SEQ ID NO:19) of humanized 77A3-1 heavy chain. Positions falling within the CDR loops are shown enclosed within the boxes with solid borders.

FIG. 21. The amino acid sequences of the light chains are shown: h77A3-1 and h77A3-2 (SEQ ID NO:17); m77A3 (SEQ ID NO:9); m49C9 (SEQ ID NO:5); m70B11 (SEQ ID NO:7); murine consensus (SEQ ID NO:75), which shows the consensus between m77A3, m49C9, and m70B11; 77A3/49C9 consensus (SEQ ID NO:76), which shows the consensus between 77A3 and 49C9; and all (SEQ ID NO:77), which shows the consensus between h77A3-1, h77A3-2, m77A3, m49C9, and m70B11. Positions falling withing the CDR loops are shown enclosed within the boxes.

FIGS. 22A–B. The amino acid sequences of the heavy chains are shown. h77A3-1 (SEQ ID NO:19); h77A3-2 (SEQ ID NO:21); m77A3 (SEQ ID NO:15); m49C9 (SEQ ID NO:11); m70B11 (SEQ ID NO:13); humanized consensus (SEQ ID NO:78), which is the consensus between h77A3-1 and h77A3-2; murine consensus (SEQ ID NO:79), which is the consensus between m77A3, m49C9, and m70B11; 77A3/49C9 consensus (SEQ ID NO:80), which is the consensus between 77A3 and 49C9; and all (SEQ ID NO:81), which is the consensus between h77A3-1, h77A3-2, m77A3, m49C9, and m70B11. Positions falling withing the CDR loops are shown enclosed within the boxes.

DETAILED DESCRIPTION OF THE PREFERRED EMBODIMENTS

Figure 1:
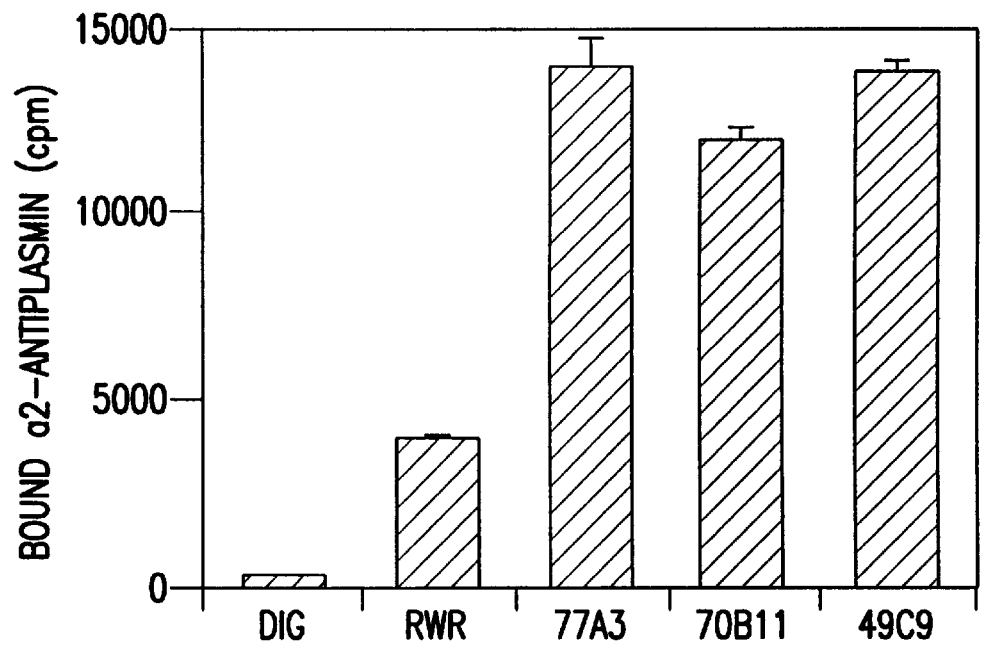
FIG. 1. Comparison of binding to $^{125}$I-α2-antiplasmin of monoclonal antibodies 49C9, 70B11, 77A3, RWR and anti-digoxin (control). Wells of a microtiter plate were coated with goat antimouse antibody. The wells were incubated in duplicate with 49C9, 70B11, 77A3, RWR or a control (antidigoxin) MAb (Mudgett-Hunter, M. et al., Mol. Immunol. 22:477–488 (1985)). After a wash, $^{125}$I-α2AP (60,000 cpm) was added for an hour. The wells were rinsed and the amount of bound $^{125}$I-α2AP was measured in a gamma counter.

Alpha-2-antiplasmin (α2AP) is a molecular mediator of the thrombus resistance in patients with pulmonary embolism. A specific inhibitor of α2AP is described which is used to determine the role played by α2AP in the regulation of fibrinolysis.

A. Immunologic Molecules

In the following description, reference will be made to various methodologies well-known to those skilled in the art of immunology. Standard reference works setting forth the general principles of immunology include Klein, J., *Immunology: The Science of Cell-Noncell Discrimination*, John Wiley & Sons, New York (1982); Kennett, R et al., *Monoclonal Antibodies, Hybridoma: A New Dimension in Biological Analyses*, Plenum Press, New York (1980); Campbell, A, "Monoclonal Antibody Technology," in *Laboratory Techniques in Biochemistry and Molecular Biology*, Vol. 13, Burdon, R., et al., eds., Elsevier, Amsterdam (1984); and Eisen, H. N., *Microbiology*, 3rd ed, Davis, B. D., et al., Harper & Row, Philadelphia (1980).

As used herein, α2AP-binding molecule includes antibodies (polyclonal or monoclonal), as well as ligands. As used herein, an "immunologic molecule" refers to polypeptides comprising the binding region of a monoclonal antibody. Thus, monoclonal antibodies, antibody fragments, chimeric antibodies, humanized antibodies, and fusion proteins comprising antibody binding regions are "immunologic molecules". The term "antibody" (Ab) or "monoclonal antibody" (MAb) is meant to include intact molecules as well as antibody fragments (such as, for example, Fv, Fab and F(ab')$_2$ fragments), single chain antigen-binding proteins, "humanized" antibodies, and chimeric antibodies which are capable of specifically binding to α2AP. Fab and F(ab')$_2$ fragments lack the Fc fragment of intact antibody, clear more rapidly from the circulation, and may have less non-specific tissue binding of an intact antibody (Wahl et al., *J. Nucl. Med.* 24:316–325 (1983)). Thus, these fragments are preferred.

An antibody is said to be "capable of binding" a molecule if it is capable of specifically reacting with the molecule to thereby bind the molecule to the antibody. As used herein, the term "hapten" is intended to refer to any molecule capable of being bound by an antibody. The term "epitope" is meant to refer to that portion of a hapten which can be recognized and bound by an antibody. A hapten or antigen may have one, or more than one epitope. An "antigen" or "immunogen" is a hapten which is additionally capable of inducing an animal to produce antibody capable of binding to an epitope of that antigen. The specific reaction referred to above is meant to indicate that the hapten will react, in a highly selective manner, with its corresponding antibody and not with the multitude of other antibodies which may be evoked by other antigens.

The antibodies of the present invention may be prepared by any of a variety of methods. For example, cells expressing α2AP (or fractions, lysates, etc. thereof) can be administered to an animal in order to induce the production of sera containing polyclonal antibodies that are capable of binding α2AP. In a preferred method, a preparation of α2AP of the present invention is prepared and purified to render it substantially free of natural contaminants. Such a preparation is then introduced into an animal in order to produce polyclonal antisera of greater specific activity.

The antibodies of the present invention may also be prepared using phage display technology. Methods of preparing antibodies using phage display are known in the art. See, for example, U.S. Pat. No. 5,565,332; Clarkson et al., Nature 352:624–628 (1991); Huse, Science 246:1275–1281 (1989); Kang, Proc. Natl. Acad. Sci. USA 88:11120–11123 (1993); Marks, J. Mol. Biol. 222:581–597 (1991); and McCafferty et al., Nature 348:552–554 (1990).

In one preferred method, the immunogenic molecules of the present invention are monoclonal antibodies (or α2AP binding molecules). Such monoclonal antibodies can be prepared using hybridoma technology (Kohler et al., Nature 256:495 (1975); Kohler et al., Eur. J. Immunol. 6:511 (1976); Kohler et al., Eur. J. Immunol. 6:292(1976); Hammerling et al., in Monoclonal Antibodies and T-Cell Hybridomas, Elsevier, N.Y., pp. 563–681 (1981)). In general, such procedures involve immunizing an animal (preferably a mouse) with the antigen or with a cell which expresses the antigen. A preferred antigen is purified α2AP. The most preferred antigen is α2AP fragment (fibrin binding region) obtained by trypsin digest of a plasma clot, then affinity purified with a SEPHAROSE-coupled monoclonal antibody, RWR (Reed, G. L. III et al., Trans. Assoc. Am. Phys. 101:250–256 (1988); U.S. Pat. No. 5,372,812, issued Dec. 13, 1994). Suitable cells can be recognized by their capacity to secrete anti-α2AP antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 μg/l of nonessential amino acids, about 1,000 U/ml of penicillin, and about 100 μg/ml of streptomycin. The splenocytes of such mice are extracted and fused with a suitable myeloma cell line. The method of somatic cell fusion is described in Galfre, G. and Milstein, C., Meth. Enzymol. 73:3–46 (1981). After fusion, the resulting hybridoma cells are selectively maintained in HAT medium, and then cloned by limiting dilution as described by Wands et al., Gastroenterology 80:225–232 (1981). The hybridoma cells obtained through such a selection are then assayed to identify clones which secrete antibodies capable of binding α2AP.

Alternatively, additional antibodies capable of binding to the α2AP antigen may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, α2AP-specific antibodies are used to immunize an animal, preferably a mouse. The splenocytes of such an animal are then used to produce hybridoma cells, and the hybridoma cells are screened to identify clones which produce an antibody whose ability to bind to the α2AP-specific antibody can be blocked by the α2AP antigen. Such antibodies comprise anti-idiotypic antibodies to the α2AP-specific antibody and can be used to immunize an animal to induce formation of further α2AP-specific antibodies.

It will be appreciated that Fab and F(ab')$_2$ and other fragments of the antibodies of the present invention may be used according to the methods disclosed herein. Such fragments are typically produced by proteolytic cleavage, using enzymes such as papain (to produce Fab fragments) or pepsin (to produce F(ab')$_2$ fragments). Alternatively, α2AP-binding fragments can be produced through the application of recombinant DNA technology, through synthetic chemistry, or biotinylation.

Also intended within the scope of the present invention are humanized or chimeric antibodies, produced using genetic constructs derived from hybridoma cells producing the MAbs described above. Humanized antibodies are antibodies in which the framework or other regions of the murine Ab is replaced with the homologous regions of a nonmurine antibody. Chimeric antibodies are antibodies in which the murine constant region has been replaced with a non-murine constant region. Methods for production of chimeric antibodies are known in the art. See, for review: Morrison, Science, 229:1202–1207 (1985); Oi et al., BioTechniques 4:214 (1986); see also, Cabilly et al., U.S. Pat. No. 4,816,567 (Mar. 28, 1989); Taniguchi et al., EP171496 (Feb. 19, 1986); Morrison et al., EP173494 (Mar. 5, 1986); Neuberger et al., WO8601533 (Mar. 13, 1986); Robinson et al., WO 8702671 (May 7, 1987); Boulianne et al., Nature 312:643–646 (1984); and Neuberger et al., Nature 314:268–270 (1985). Methods for production of humanized antibodies are known in the art. See, for example, U.S. Pat. No. 5,585,089; Jones et al., Nature 321:522–525 (1986); and Kettleborough et al., Protein Engineering 4:773–783 (1991).

Also provided in the present invention are single-chain antibodies capable of binding to both (1) human and nonhuman circulating α2-antiplasmins and (2) human and nonhuman fibrin crosslinked α2-antiplasmins. Methods of making single chain antibodies are well known in the art. See, for example, U.S. Pat. No. 4,946,778; U.S. Pat. No. 5,260,203; U.S. Pat. No. 5,091,513; and U.S. Pat. No. 5,455,030, all of which are herein incorporated by reference.

Also intended within the scope of the present invention are variants of the monoclonal antibodies described above.

The present inventors have determined the nucleotide and amino acid sequence of several immunologic molecules capable of binding to both (1) human and nonhuman circulating α2-antiplasmins and (2) human and nonhuman fibrin crosslinked α2-antiplasmins. Accordingly, the present invention provides for nucleic acid molecules comprising a nucleotide sequence encoding for an immunologic molecule of the present invention or fragment thereof.

Due to the degeneracy of the genetic code, and to the fact that the genetic code is known, all other nucleotide sequences which encode the same amino acid sequence as the nucleotides of the present invention can be determined and used in the practice of the present invention.

DNA clones containing nucleotide sequences encoding the following antibody chains were deposited at the American Type Culture Collection, 12301 Parklawn Drive, Rockville, Md., 20862 on Sep. 19, 1997: light chain of 77A3 (77A3 LC), ATCC Accession No. 209290 light chain of 49C9 (49C9 LC), ATCC Accession No. 209291 light chain of 70B11 (70B11 LC), ATCC No. 209292 heavy chain of 77A3 (77A3 HC), ATCC No. 209287 heavy chain of 49C9 (49C9 HC), ATCC No. 209289 and heavy chain of 70B11 (70B11 HC), ATCC No. 209288.

The nucleic acid molecules of the present invention include: nucleic acid molecules containing a nucleotide sequence encoding the mature light chain of 77A3 as shown in SEQ ID NO:9 or as encoded by the clone contained in the ATCC No. 209290 nucleic acid molecules containing a nucleotide sequence encoding the mature light chain of 49C9 as shown in SEQ ID NO:5 or as encoded by the clone contained in ATCC No. 209291 and nucleic acid molecules containing a nucleotide sequence encoding the mature light chain of 70B11 as shown in SEQ ID NO:7 or as encoded by the clone contained in ATCC No. 209292.

Also included in the present invention are nucleic acid molecules containing a nucleotide sequence encoding an antibody heavy chain, including: nucleic acid molecules containing a nucleotide sequence encoding the mature heavy chain of 77A3 as shown in SEQ ID NO:15 or as encoded by the clone contained in ATCC No. 209287 nucleic acid molecules containing a nucleotide sequence encoding the mature heavy chain of 49C9 as shown in SEQ ID NO:11 or as encoded by the clone contained in ATCC No. 209289 and nucleic acid molecules containing a nucleotide sequence encoding the mature heavy chain of 70B11 as shown in SEQ ID NO:13 or as encoded by the clone contained in ATCC No. 209288.

Also included are nucleic acid molecules encoding humanized antibodies including: nucleic acid molecules comprising a nucleotide sequence encoding for amino acid residues 1 to 107 of SEQ ID NO:17; nucleic acid molecules comprising a nucleotide sequence encoding for amino acid residues 1 to 119 of SEQ ID NO:19; and nucleic acid molecules comprising a nucleotide sequence encoding for amino acid residues 1 to 119 of SEQ ID NO:21.

Also intended within the scope of the invention are nucleic acid molecules encoding "consensus" amino acid sequences of heavy and light chain of antibodies, including: nucleic acid molecules comprising a nucleotide sequence encoding for amino acid residues 1 to 107 of SEQ ID NO:75; nucleic acid molecules comprising a nucleotide sequence encoding for amino acid residues 1 to 107 to of SEQ ID NO:76; nucleic acid molecules comprising a nucleotide sequence encoding for amino acid residues 1 to 107 of SEQ ID NO:77; nucleic acid molecules comprising a nucleotide sequence encoding for amino acid residues 1 to 119 of SEQ ID NO:78; nucleic acid molecules comprising a nucleotide sequence encoding for amino acid residues 1 to 119 of SEQ ID NO:79; nucleic acid molecules comprising a nucleotide sequence encoding for amino acid residues 1 to 119 of SEQ ID NO:80; and nucleic acid molecules comprising a nucleotide sequence encoding for amino acid residues 1 to 119 of SEQ ID NO:81.

Nucleic acid molecules encoding an immunologic molecule of the present invention can be used to express recombinant proteins. A nucleic acid molecule encoding an immunologic molecule of the present invention can be inserted into a vector in accordance with conventional techniques. A "vector" should be understood as a nucleic acid vehicle used for cloning or expressing a desired sequence in a host.

In one embodiment, the recombinant vector is capable of expressing the immunologic molecule of the present invention. A vector is said to be "capable of expressing" a polypeptide if it contains a nucleotide sequence that encodes for the polypeptide, as well as transcriptional and translational regulator information operably linked to the nucleotide sequence that encodes the polypeptide. Two nucleotide sequences are said to be "operably linked" if the nature of the linkage between the two nucleotide sequences does not: result in the introduction of a frame-shift mutation; interfere with the ability of the promoter region sequence to direct the transcription of the desired sequence; or interfere with the ability of the desired sequence to be transcribed by the promoter region sequence. Thus, a promoter region would be operably linked to a desired nucleotide sequence if the promoter were capable of effecting transcription of that nucleotide sequence.

Once the recombinant vector is constructed, it can be introduced into a host cell, either prokaryotic or eukaryotic, by a variety of conventional techniques including transfection, transduction, electroporation, calcium-phosphate precipitation, and microinjection. Prokaryotic hosts include bacteria such as E. coli, Bacillus, Streptomyces, and Salmonella. The most preferred prokaryotic host is E. coli. Eukaryotic hosts include yeast cells, insect cells, and mammalian cells, such as COS cells, CHO cells, and myeloma cells. In one embodiment of the invention, CHO cells are preferred.

In one embodiment of the invention, a nucleic acid molecule comprising a nucleotide sequence encoding for the light chain of an antibody is introduced into a vector, and a nucleic acid molecule comprising a nucleotide sequence encoding for the heavy chain of an antibody is introducing into another vector. Both vectors are introduced into the same host cell. Alternatively, both chains could be introduced into the same vector.

Following expression in an appropriate host, the polypeptide can be readily isolated using standard techniques, including affinity chromatography.

Also intended within the scope of the present invention are molecules comprising an amino acid sequence of the binding region of an immunologic molecule described herein. Molecules comprising an amino acid sequence of the binding region of an immunologic molecule described herein include, but are not limited to, monoclonal antibodies, humanized antibodies, chimeric antibodies, fragments of any such antibodies, single chain antibodies, fusion proteins, and the like. Such molecules can be used in the assays and methods of treatment of the present invention described below.

Figure 22A:
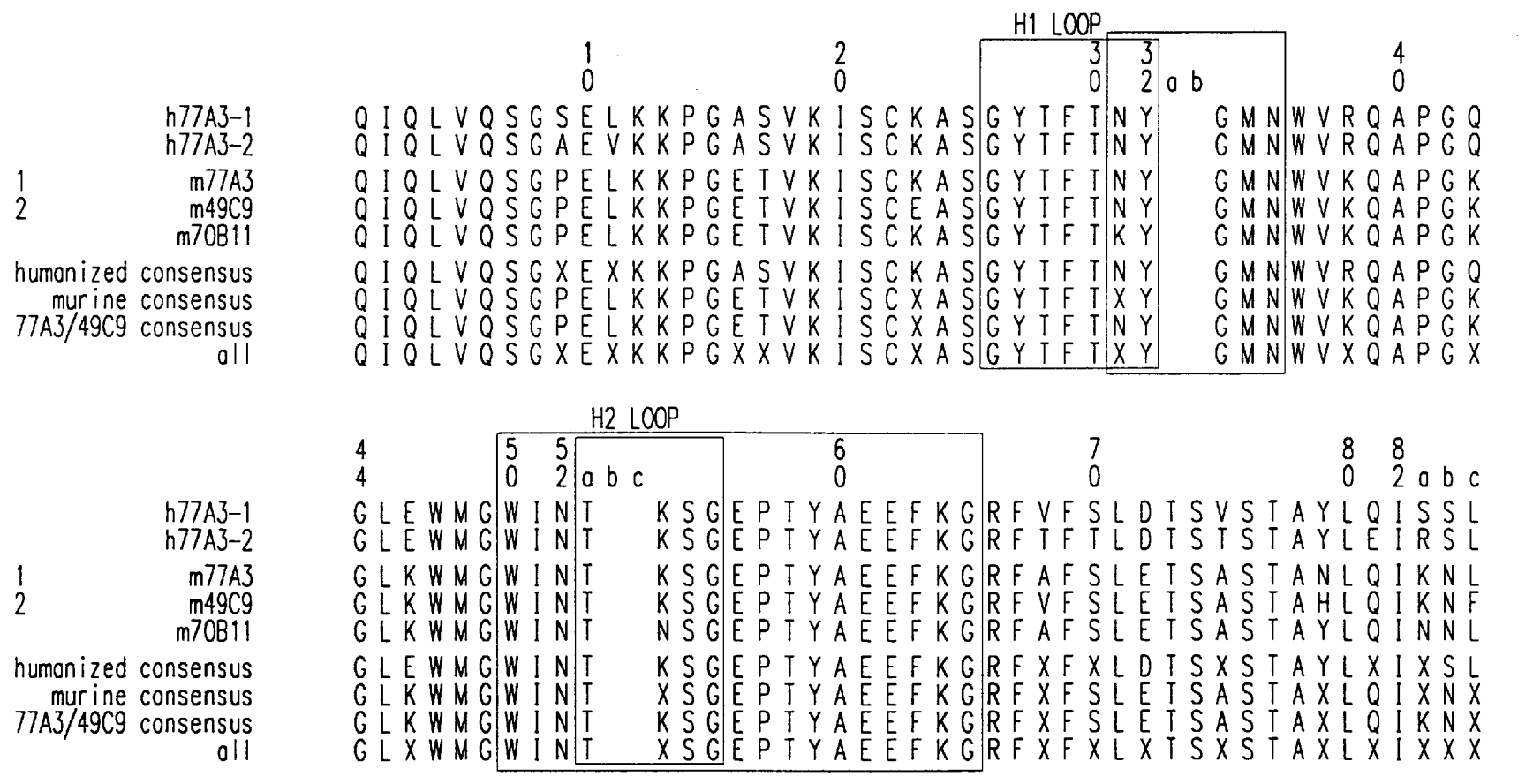

The amino acid sequence of the binding region of the immunologic molecules of the present invention are shown in FIG. 21 for the light chains and FIG. 22 for the heavy chains. In FIG. 21, the amino acid sequence of the binding regions of the light chains of h77A3-1 and h77A3-2 (amino acid residues 24 to 34, 50 to 56 and 89 to 97 of SEQ ID NO:17), m77A3 (amino acid residues 24 to 34, 50 to 56 and 89 to 97 of SEQ ID NO:9), m44C9 (amino acid residues 24 to 34, 50 to 56 and 89 to 97 of SEQ ID NO:5), m70B11 (amino acid residues 24 to 34, 50 to 56 and 89 to 97 of SEQ ID NO:7), the murine consensus (amino acid residues 24 to 34, 50 to 56 and 89 to 97 of SEQ ID NO:75), the 77A3/49C9 consensus (amino acid residues 24 to 34, 50 to 56 and 89 to 97 of SEQ ID NO:76) and the consensus of all light chains (amino acid residues 24 to 34, 50 to 56 and 89 to 97 of SEQ ID NO:77) are shown in the larger boxes.

In FIG. 22, the amino acid sequence of the binding regions of the heavy chains of h77A3-1 (amino acid residues 26 to 35, 50 to 66 and 99 to 108 of SEQ ID NO:19), h77A3-2 (amino acid residues 26 to 35, 50 to 66 and 99 to 108 of SEQ ID NO:21), m77A3 (amino acid residues 26 to 35, 50 to 66 and 99 to 108 of SEQ ID NO:15), m49C9 (amino acid residues 26 to 35, 50 to 66 and 99 to 108 of SEQ ID NO:11), m70B11 (amino acid residues 26 to 35, 50 to 66 and 99 to 108 of SEQ ID NO:13), the humanized consensus (amino acid residues 26 to 35, 50 to 66 and 99 to 108 of SEQ ID NO:78), the murine consensus (amino acid residues 26 to 35, 50 to 66 and 99 to 108 of SEQ ID NO:79), the 77A3/49C9 consensus (amino acid residues 26 to 35, 50 to 66 and 99 to 108 of SEQ ID NO:80), and the consensus of all the heavy chains (amino acid residues 26 to 35, 50 to 66 and 99 to 108 of SEQ ID NO:81) are shown in the overlapping boxes.

B. Assays

Methods for immunoblotting are known in the art (see, for example, Reed, G. L. et al., *J. Immunol.* 150:4407–4415 (1993)). In a preferred method, the α2AP is electrophoresed on a slab minigel under reducing and non-reducing conditions. The gel is electroblotted to polyvinylidene difluoride membrane. The blot is exposed to different hybridoma supernatants in the channels of a miniblotter apparatus. After washing, the bound antibody is detected by incubation with $^{125}$I-goat antimouse antibody. After additional washing, the membrane is exposed in a phosphorimager (Molecular Devices, Sunnyvale, Calif.).

Methods for radioimmunoassays are also known. For example, the wells of a microtiter plate are coated with goat antimouse antibody. The wells are washed and blocked with BSA. The hybridoma supernatants are added to the empty wells. After incubation, the wells are washed and $^{125}$I-α2AP is added. After washing, the wells are cut and the bound antibody is measured by gamma scintillation counting. For competition assays, the wells of a microtiter plate are coated with a competing MAb. In a preferred embodiment, the binding of MAbs to $^{125}$I-α2AP (preferably, the fibrin binding region fragment of α2AP, obtained by binding to RWR) is assayed by reverse solid-phase radioimmunoassay.

Methods for clot assays are also known (see, for example, Reed, G. L. III et al., *Proc. Natl. Acad Sci. USA* 87:1114–1118 (1990). In a preferred embodiment, plasma is mixed with $^{125}$I-fibrinogen, then clotted by mixing with CaCl$_2$ and thrombin. Clots are compressed and washed with Tris-buffered saline to remove unbound proteins. The supernatant is removed and the clots counted in a gamma counter. To each set of duplicate clots is added, various amounts of plasminogen activator, anti-coagulant, and Tris-buffered saline containing the MAb or no MAb. The clots are incubated and at various intervals, a portion of the solution is temporarily removed and gamma-counted to determine the amount of lysis. The percent lysis may be defined at 100× (total supernatant cpm/total clot cpm).

Fibrinogen assays are known. Blood samples and platelet-poor plasma are assayed for fibrinogen by, for example, the sodium sulfite method (Rampling, M. W. and Gaffney, P. J., *Clin. Chim. Acta.* 67:43–52 (1976)).

Alpha-2-antiplasmin levels in plasma are assayed, for example, with a chromogenic substrate assay for plasmin inhibition (Stachrom kit) as described in Reed, G. L., III et al., *Proc. Natl. Acad. Sci. USA* 87:1114–1118 (1990).

Statistical tests may be analyzed by, for example, a one way analysis of variance followed by a Bonferroni-Dunn procedure for multiple comparison testing.

In vivo pulmonary embolism experiments are described in Example 2, below.

C. Methods of Treatment

By "patient" is intended, human or nonhuman. Nonhumans include, for example, baboon, green monkey, dog, cynamologus, marmoset, ferret, guinea pig, and gerbil.

By "clot" is intended, an in vitro blood or fibrin clot, or "thrombi" in a patient. Diseases treated according to the methods of his invention include, but are not limited to pulmonary thromboembolism; acute coronary syndrome, including unstable angina pectoris and non-Q-wave myocardial infarction; various forms of thrombosis, including venous thrombosis (e.g., deep venous thrombosis), and arterial thrombosis (e.g., renal, mesenteric, and limb thrombosis); and cerebral and thrombosis embolism; renal vein and peripheral arterial thrombosis, myocardial infarction, stroke, and other thromboses. This method may also be used to treat thrombotic conditions secondary or concomitant to surgical procedures, including percutaneous transluminal coronary angioplasty, peripheral arterial angioplasty, bypass graft, and stent. The "treating" or "treatment" is by, for example, inhibiting the formation of a thrombus, dissolving a thrombus, or by enhancing fibrinolysis.

By the term "co-administration" is intended that each of the hapten-binding molecule and thrombolytic agent will be administered during a time frame wherein the respective periods of pharmacological activity overlap. The two agents may be administered simultaneously or sequentially.

The α2AP-binding molecules of the present invention may be monoclonal antibodies or fragments thereof It is preferable to employ the F(ab')$_2$ fragment of such an antibody for this purpose, in order to minimize any immunological reaction caused by the Fc portion of the immunoglobulin. Also preferred are single-chain antibodies, such as sFv. Procedures for preparing monoclonal antibodies are disclosed by Kaprowski, H. et al., U.S. Pat. No. 4,172,124, and Kohler et al., *Nature* 256:495–497 (1975). The preparation of monoclonal antibodies capable of preventing the inhibition of plasmin are taught by Mimuro, J. et al., *Blood* 69:446–453 (1987), and described in the examples section of the present application.

As used herein, an "antigen" is a molecule capable of being bound by an antibody such as, for example, α2AP. In order to be used in accordance with the present invention, the "antigen-binding molecule" must be capable of binding to a plasmin inhibitor and thereby prevent such an inhibitor from forming inhibitor-plasmin complexes. Any such antigen-binding molecule may be employed in accordance with the present invention. A preferred embodiment is α2AP-binding molecule which is capable of binding to α2AP or fragment thereof An especially preferred α2AP-binding molecule for this purpose is a monoclonal antibody. Preferred embodiments of the monoclonal antibody is 77A3, 70B11 or 49C9, described more fully below. The hybridoma producing MAb 77A3 has been deposited under the terms of the Budapest Treaty with the International Depository Authority American Type Culture Collection, 12301 Parklawn Drive, Rockville, Md. 20852, U.S.A., on Sep. 20, 1996; the ATCC Accession No. is HB-12192.

Also preferred are chimeric an humanized antibodies. An especially preferred chimeric antibody for this purpose is c77A3, described more fully below. Especially preferred humanized antibodies for this purpose are h77A3-1 and h77A3-2, described more fully below. Also preferred are antibody fragments and single-chain antibodies, including sFv77A3-1 and sFv77A3-2, described below.

The terms "thrombolytic agent" are meant to refer to any agent capable of either dissolving a fibrin and/or platelet clot (or thrombus), or inhibiting the formation of such a clot. Examples of thrombolytic agents include fibrinolytic molecules, such as plasmin, plasminogen activator (for example, staphylokinase, streptokinase, prourokinase, urokinase, tissue-type plasminogen activator, and vampire bat plasminogen activator); anti-coagulants (for example, inhibitors of fibrin formation, such as heparin, hirudin and activated protein C; and anti-platelet agents, such as ticlopidine, aspirin, and clopidigrel and inhibitors of glycoprotein IIb/IIIa function). Use of t-PA for these purposes is especially preferred. Although natural t-PA may be employed, it is preferable to employ recombinant t-PA (rt-PA). The invention may additionally employ hybrids, physiologically active fragments or mutant forms of the above thrombolytic agents. For example, the term "tissue-type plasminogen activator" as used herein is intended to include such hybrids, fragments and mutants, as well as both naturally derived and recombinantly derived tissue-type plasminogen activator.

As stated, the methods of the invention comprise the administration of the α2AP-binding molecule alone or in combination with a thrombolytic agent. When administered alone the molecule enhances endogenous fibrinolysis or thrombolysis by significantly augmenting clot lysis by endogenous plasminogen activators. Further, administration of the α2AP-binding molecule does not increase fibrinogen consumption over that obtained with equivalent doses of t-PA alone. Thus, the present method of clot-specific inhibition of α2AP enhances the potency of the plasminogen activator and preserves its fibrin selectivity.

Alternatively, the α2AP-binding molecule is administered with a thrombolytic agent. In this embodiment, the α2AP-binding molecule and the thrombolytic agent of the present invention are intended to be co-administered to the recipient. It is preferable to provide the α2AP-binding molecule to the patient prior to the administration of the thrombolytic agent.

The α2AP-binding molecule of the present invention is provided for the purpose of preventing the inhibition of plasmin by a plasmin inhibitor. It has been discovered that coadministration of the α2AP-binding molecule together with a thrombolytic agent causes a synergistic effect, and thereby enhances clot lysis (thrombolysis) to a greater extent than would be expected if the effects of α2AP-binding molecule administration and thrombolytic agent administration was merely additive.

The α2AP-binding molecule of the present invention encompasses clot-specific inhibitors of α2AP. It is demonstrated that the combination oft-PA and the specific inhibitors, particularly monoclonal antibodies to α2AP, does not increase fibrinogen consumption over that obtained with equipotent doses of plasminogen activator alone. Further, clot-specific inhibition of α2AP enhances the potency of plasminogen activators and preserves fibrin selectivity. For agents such as urokinase, which is not selective for fibrin, inhibition of clot bound α2AP would cause a similar, or more pronounced, enhancement in potency and lead to less fibrinogen consumption as well.

Thus, the inhibition of clot-bound α2AP enhances clot lysis by endogenous plasminogen activators. Further, when administered in combination with a thrombolytic agent, thrombolysis is significantly increased compared with the lysis achieved by equivalent doses of the thrombolytic agent alone. This increased lysis by the combination of the thrombolytic agent and α2AP inhibitor occurs without decreasing circulating fibrinogen or α2AP levels. The net result is a synergistic interaction between the two agents.

When used alone, an amount of α2AP-binding molecule capable of preventing inhibition of plasmin and thereby enhancing clot lysis when provided to a patient is a "therapeutically effective" amount. In order to enhance clot lysis and prevent clot reformation, it is desirable to provide between 3 to 300 nmole of α2AP-binding molecule per kilogram of patient weight. This dosage may be administered, in one embodiment, over a period of between 60 to 480 minutes, by continual intravenous infusion at a rate of 0.006 to 5 nmole/kg/min. Alternatively, it is possible to provide the α2AP-binding molecule in an intravenously injectable bolus at a dose of between 3 to 600 nmole/kg, and most preferably between 30 to 60 nmole (of α2AP-binding molecule) per kilogram of patient weight. If the α2AP-binding molecule is provided in this manner, a single bolus is sufficient to prevent potential clot reformation. The α2AP-binding molecule of the present invention may be dissolved in any physiologically tolerated liquid in order to prepare an injectable bolus. It is preferable to prepare such a bolus by dissolving the α2AP-binding molecule in normal saline.

When the α2AP-binding molecule capable of preventing inhibition of plasmin is co-administered with a thrombolytic agent, it is desirable to provide 3 to 300 nmole of α2AP-binding molecule per kilogram of patient weight. This dosage may be administered, in one embodiment, over a period of 60 to 480 minutes, by continuous intravenous infusion. Alternatively, it is possible to provide the α2AP-binding molecule in an intravenously injectable bolus at a dose of between 3 to 600 nmole/kg, and most preferably between 30 to 60 nmole/kg of patient weight. An amount of thrombolytic agent capable of causing such lysis is a "therapeutically effective" amount. It is desirable to provide between 0.01 to 3.0 mg per kilogram of patient weight. In one embodiment, the thrombolytic agent is provided over a prolonged period (i.e., from about 180 to about 1440 minutes). In a preferred embodiment, the thrombolytic agent of the present invention is provided as an intravenously injected bolus containing between 0.5 to 1.0 mg/kg, and most preferably between 0.5 to 0.75 mg/kg. For example, for pulmonary embolism, the dosage oft-PA by continuous infusion is ~100 mg for 2 hours (Goldhaber, S. C. et al., *Lancet* 341:507 (1993)). The dosage to be used of thrombolytic agent of the present invention is generally known in the art (see, e.g., *Hemostasis and Thrombosis: Basic Principles and Clinical Practice*, 3rd ed. Philadelphia, Pa. (1994)).

The thrombolytic agent of the present invention may be dissolved in any physiologically tolerated liquid in order to prepare an injectable bolus. It is, however, preferable to prepare such a bolus by dissolving the thrombolytic agent in normal saline.

A patient treated according to the preferred embodiment will, therefore, receive an intravenously injected bolus of the α2AP-binding molecule in combination with an intravenously injected bolus of the thrombolytic agent. This preferred treatment minimizes the amount of t-PA required for thrombolysis, thus reducing the extent of fibrinogen breakdown and lessening any tendency for general hemorrhage. Importantly, the use of the preferred treatment results in the dissolution of the occluding thrombus at a rate which greatly exceeds the rate of thrombus dissolution when either the α2AP-binding molecule or the thrombolytic agent is provided by infusion alone. Additionally, the risk of reocclusion is substantially reduced.

In previous models of fibrinolysis (3), the chief role assigned to α2AP has been to inactivate circulating plasmin and prevent a systemic lytic state. Thus, it may be surprising that an α2AP inhibitor can increase clot lysis without increasing fibrinogenolysis. This marked amplification of thrombolysis by α2AP inhibitor underscores the importance of fibrin bound α2AP in regulating fibrinolysis. Since the subject antibodies augment clot lysis by a fibrin-selective agent such as t-PA as well as that by the nonselective activators urokinase and streptokinase, it appears that fibrin-bound α2AP plays a critical role in determining the rate of lysis by any exogenous plasminogen activator.

S These unexpected findings are important because it had previously not been possible to accelerate the rate of clot lysis without increasing the tendency to hemorrhage. The preferred embodiment, therefore, provides a method of treatment in which the administration of a bolus of a α2AP-binding molecule in combination with the administration of a bolus of a thrombolytic agent are capable of dissolving an occluding thrombus at a faster rate than can be obtained when either compound is administered alone. Moreover, the preferred embodiment accomplishes this goal while minimizing both fibrinogen breakdown and the risk of reocclusion. Thus, the combination of agents can significantly increase the potency and specificity of thrombolytic therapy.

As would be apparent to one of ordinary skill in the art, the required dosage of the anti-α2AP binding molecule or thrombolytic agent will depend upon the severity of the condition of the patient, and upon such criteria as the patient's height, weight, sex, age, and medical history.

The α2AP-binding molecule or thrombolytic agent of the present invention can be formulated according to known methods to prepare pharmaceutically useful compositions, such as by admixture with a pharmaceutically acceptable carrier vehicle. Suitable vehicles and their formulation are described, for example, in *Remington's Pharmaceutical Sciences*, 16th Ed., Osol, A., ed., Mack, Easton Pa. (1980). In order to form a pharmaceutically acceptable composition suitable for effective administration, such compositions will contain an effective amount of the α2AP-binding molecule or thrombolytic agent, either alone, or with a suitable amount of carrier vehicle.

Additional pharmaceutical methods may be employed to control the duration of action. Controlled release preparations may be achieved by the use of polymers to complex or absorb the α2AP-binding molecule or thrombolytic agents of the present invention. The controlled delivery may be exercised by selecting appropriate macromolecules (for example, polyesters, polyamino acids, polyvinyl pyrrolidone, ethylenevinylacetate, methylcellulose, carboxymethylcellulose, or protamine sulfate). The rate of drug release may also be controlled by altering the concentration of such macromolecules. Another possible method for controlling the duration of action comprises incorporating the therapeutic agents into particles of a polymeric substance such as polyesters, polyamino acids, hydrogels, poly(lactic acid) or ethylene vinylacetate copolymers. Alternatively, it is possible to entrap the therapeutic agents in microcapsules prepared, for example, by coacervation techniques or by interfacial polymerization, for example, by the use of hydroxymethylcellulose or gelatin-microcapsules or poly(methylmethacrylate) microcapsules, respectively, or in a colloid drug delivery system, for example, liposomes, albumin microspheres, microemulsions, nanoparticles, nanocapsules, or in macroemulsions. Such teachings are disclosed in *Remington's Pharmaceutical Sciences*, 16th Ed., Osol, A., ed., Mack, Easton Pa. (1980).

The thrombolytic agent or α2AP-binding molecule may be provided to a patient by means well known in the art. Such means of introduction include oral means, intranasal means, subcutaneous means, intramuscular means, intravenous means, intra-arterial means, or parenteral means. In one preferred method of treatment for pulmonary embolism, myocardial infarction, thrombosis or stroke, a patient is provided with a bolus (intravenously injected) containing between 0.5 to 1.0 mg/kg of a thrombolytic agent.

Generally, the results reported herein demonstrate that an inhibitor, particularly a monoclonal antibody, can be used to augment the catalytic function of an enzyme by neutralizing an inhibitor of that enzyme. This approach can be applied to biological processes which are tightly governed by inhibitors. Because coagulation is a finely balanced system in which the effects of enzymes (generally serine proteases) are pitted against the effects of inhibitors, frequently serpins (serine protease inhibitors) pathological alterations in clotting can be treated by augmenting enzyme activity or by neutralizing an inhibitor.

Having now generally described this invention, the same will be better understood by reference to certain specific examples which are included herein for purposes of illustration and are not intended as limiting.

EXAMPLE 1

Preparation of an Antibody Directed to Alpha-2-antiplasmin

A. Monoclonal Antibody Production, Purification and Characterization

Two Balb/C mice were immunized subcutaneously with 25 μg of purified human α2AP fragments derived from the trypsin digest of a human plasma clot. The α2AP fragments were affinity purified with a SEPHAROSE-coupled monoclonal antibody, RWR (Reed, G. L. III et al., *Trans. Assoc. Am. Phys.* 101:250–256 (1988); U.S. Pat. No. 5,372,812, issued Dec. 13, 1994), against human α2AP. Mice were initially immunized with complete Freund's adjuvant and boosted 90 days later with 50 μg of α2AP fragment in incomplete Freund's adjuvant. The antisera titer was tested in a solid-phase radioimmunoassay (Reed, G. L. III et al., *Proc. Natl. Acad. Sci. USA* 87:1114–1118 (1990)) with α2AP immobilized in the wells of a microtiter plate. Four days before fusion, the mouse with the highest titer of α2AP antibody was hyperimmunized with 100 μg α2AP intraperitoneally. Somatic cell fusion was performed as described (Galfre, G. and Milstein, C., *Meth. Enzymol.* 73:3–46 (1981)).

Hybridomas were tested for the production of antibodies to the α2AP fragment and for their ability to inhibit α2AP as described in Reed, G. L. III et al., *Proc. Natl. Acad. Sci. USA* 87:1114–1118 (1990). The binding of monoclonal antibodies (MAbs) to $^{125}$I-α2AP was tested in a solid-phase radioimmunoassay. Wells of a microtiter plate were coated with goat antimouse antibody (25 μl, 5 μg/ml) for 2 hours. The wells were rinsed and nonspecific protein binding sites were blocked with 1% bovine serum albumin in Tris-buffered saline, pH 7.4, for 1 hour. After a wash, 25 μl of hybridoma supernatant was added to the wells and incubated for 1 hour. The wells were rinsed and $^{125}$I-α2AP was added (25 μl, 60,000 cpm) for 1 hour. The $^{125}$I-α2AP was then removed and the wells were rinsed and gamma-counted.

Cloned hybridomas (limiting dilution) were expanded into ascites in pristane-primed Balb/C mice. Antibodies were purified from filtered ascites by precipitation with 40% ammonium sulfate, dialysis into 10 mM $KH_2PO_4$, pH 7.2, and ion-exchange chromatography on DEAE-AFFIGEL BLUE SEPHAROSE (BioRad, Hercules, Calif.) with a linear gradient from 0 to 100 mM NaCl.

B. Immunoblotting

These were performed largely as described in Reed, G. L. et al., *J. Immunol.* 150:4407–4415 (1993). Purified human α2AP (5 μg, American Diagnostica, Greenwich, Conn.) was electrophoresed in a large single sample lane on a 12% slab minigel (BioRad, Hercules, Calif.) under reducing and non-reducing conditions. The sample was electroblotted (Kyhse-Anderson, 1084) to polyvinylidene difluoride membranes (Millipore, Bedford, Mass.) and nonspecific protein binding sites were blocked with 5% dry milk. The blots were exposed to different hybridomas supernatants for 1 hour in the channels of a miniblotter apparatus (Immunetics, Cambridge, Mass.). After washing, the bound antibody was detected by incubation with $^{125}$I-goat antimouse antibody (1.5 million cpm/membrane). After additional washing, the membranes were exposed in a phosphorimager (Molecular Devices, Sunnyvale, Calif.).

C. Radioimmunoassays

Wells of a microtiter plate were coated with goat anti-mouse antibody (25 µl, 5 µl/ml) for 2 hours at 21° C. They were washed and blocked with 1% BSA (bovine albumin serum) for I hour. To the empty wells in duplicate were added 25 µl of hybridoma supernatants. After incubation for 1 hour the wells were washed and 25 µl of $^{125}$I-α2AP was added to the wells for another hour. After washing the wells were cut and the bound antibody measured by gamma scintillation counting.

Competition radioimmunoassays were performed by coating wells of a microtiter plate with 25 µl of purified MAb (70B11) in duplicate (10 µg/ml) for 1 hour. The wells were washed and blocked with 1% BSA for 1 hour. After washing, 25 µl of a competitor MAb, same MAb or negative control MAb was added to different wells (50 µg/ml) followed by 25 µl of $^{125}$I-α2-antiplasmin (100,000 cpm). After 1 hour incubation, the wells were washed, cut and the radioactivity was measured in a gamma scintillation counter.

D. Plasma Clot Lysis Assays

These were performed largely as described in Reed, G. L. III et al., *Proc. Natl. Acad. Sci. USA* 87:1114–1118 (1990). Pooled fresh frozen plasma was obtained from 5 random donors to the Massachusetts General Hospital Blood Bank. The plasma was mixed with $^{125}$I-fibrinogen to achieve ~1,000 cpm/µl. The plasma was clotted for 1 hour at 37° C. in a 12×65 mm test tube by mixing 50 µ; with 50 µl of CaCl$_2$ (5 mM final) and thrombin (1 U/ml). Clots were compressed and washed in 1 ml Tris-buffered saline (pH 7.4) to remove unbound proteins. The supernatant was removed and the clots were counted in a gamma counter. To each set of duplicate clots was added 100 µl containing various amounts of urokinase, 100 µl of pooled plasma containing 1 u/ml of hirudin and 100 µl of Tris-buffered saline containing 7 µg (FIG. 4) or 21 µg (FIG. 5) of MAb or no MAb. The clots were placed in a 37° C. water bath and at various intervals 100 µl of solution was temporarily removed and gamma-counted to determine the amount of lysis. The percent lysis was defined at 100× (total supernatant cpm÷total clot cpm).

E. Results

Figure 2:
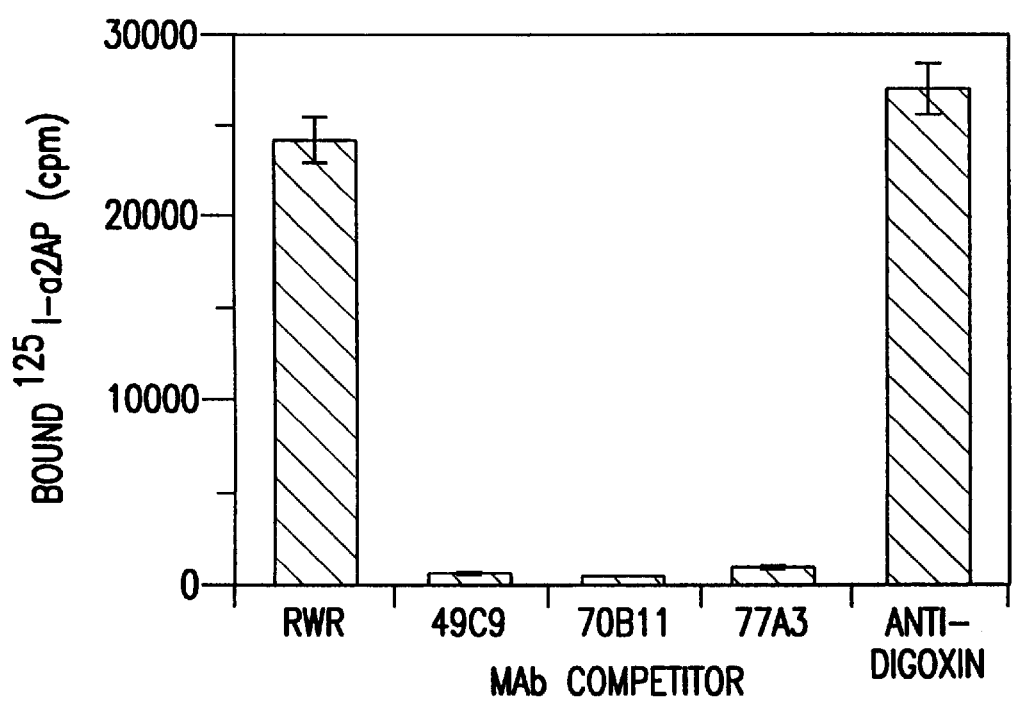
FIG. 2. Competition binding assays of monoclonal antibodies 49C9, 70B11, 77A3, RWR and anti-digoxin with immobilized 70B11. Competition radioimmunoassays were performed by coating wells of a microtiter plate with 25 μl of purified MAb (70B11) in duplicate (10 μg/ml) for 1 hour. The wells were washed and blocked with 1% BSA for 1 hour. After washing, 25 μl of a competitor MAb, same MAb or negative control MAb was added to different wells (50 μg/ml) followed by 25 μl of $^{125}$I-α2-antiplasmin (100,000 cpm). After 1 hour incubation, the wells were washed, cut and the radioactivity was measured in a gamma scintillation counter.

Three hybridomas were selected that appeared to inhibit α2AP function in screening assays. The serotypes of these MAbs were: 49C9 (Igγ2aK), 70B11 (Igγ1K), and 77A3 (Igγ2aK). FIG. 1 compares the binding of these MAbs to $^{125}$I-α2AP in a reverse solid-phase assay. When compared to the original α2AP inhibitor RWR, these MAbs bound with greater avidity. To determine if the MAbs bound to the same epitopes, competition assays is shown for 70B11 in FIG. 2. Compared to the negative control, anti-digoxin MAb, RWR had no significant inhibitory effects on the binding of $^{125}$I-α2AP to immobilized 70B11. In contrast, when 70B11 was used as a competitor, it completely inhibited the binding of $^{125}$I-α2AP to immobilized 70B11, as expected. However, 49C9 and 77A3 were also excellent competitors as well. The results of these assays are shown in tabular form in Table 1, below. MAbs 49C9, 70B11, 77A3 also fully inhibited the binding of each other to $^{125}$I-α2AP, but they had no inhibitory effects on the binding of RWR. The converse was also true, RWR as a competitor had no effect on the binding of $^{125}$I-α2AP to the other MAbs. This indicated that MAbs 49C9, 70B11 and 77A3 competed for binding to the same epitope, while RWR appeared to bind to a separate region of α2AP.

To determine if the MAbs recognized a continuous or discontinuous epitope in α2AP, immunoblotting experiments were performed with denatured and reduced α2AP. In these studies RWR bound well to denatured and reduced α2AP, indicating that it recognized an epitope which was not affected by boiling with SDS, nor reduction of disulfide bonds. In contrast, MAbs 49C9, 70B11 and 77A3 did not bind to denatured α2AP, suggesting that they recognize a conformation-dependent epitope.

Figure 3:
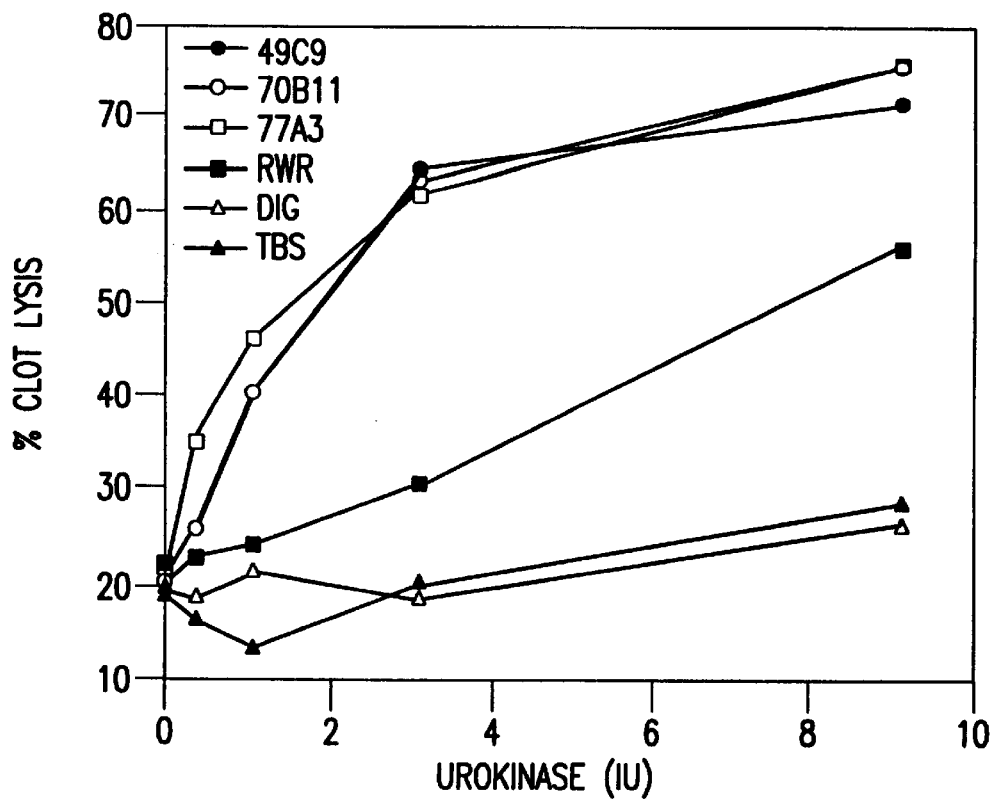
FIG. 3. Comparison of amount of lysis by different monoclonal antibodies (or TBS alone) as a function of dose of urokinase. See Example 1, below, for detailed description of the method. The amount of lysis was determined by gamma counting. The percent lysis was defined at 100×(total supernatant cpm÷total clot cpm).
Figure 4:
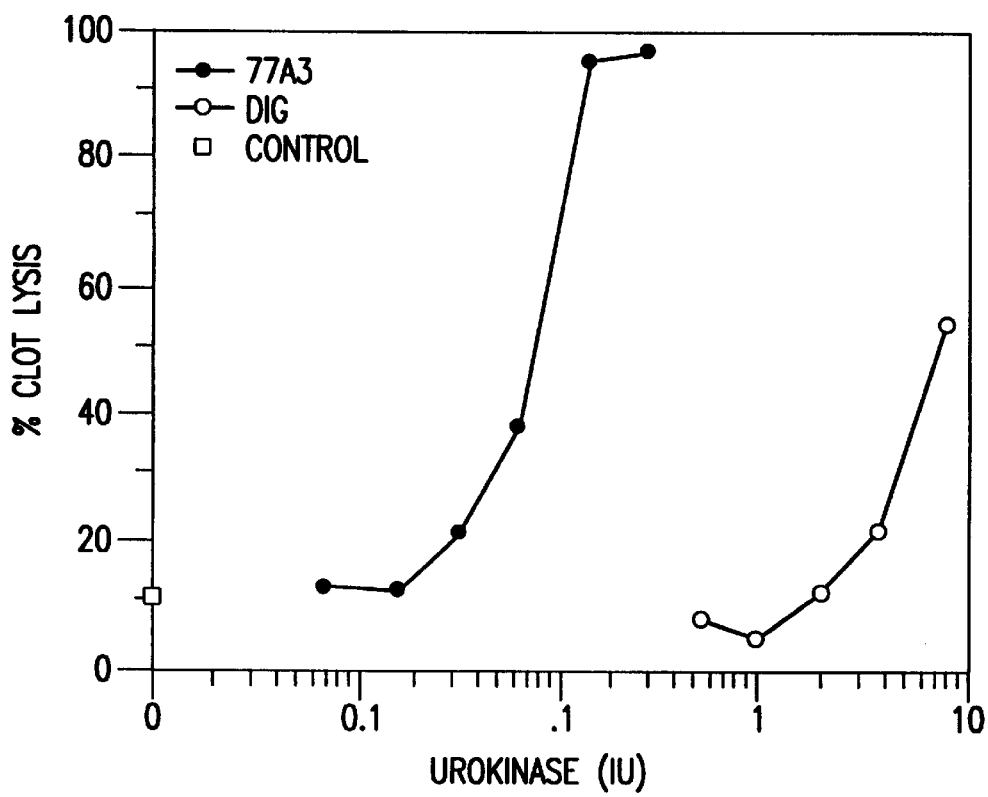
FIG. 4. Dose response studies in the absence or presence of MAb 77A3. Lysis by urokinase is increased approximately 100-fold by 77A3.

Clot lysis assays were performed to examine the relative potency of these MAbs in amplifying the fibrinolysis by urokinase. FIG. 3 compares the amount of lysis achieved by 7 µg of different purified MAbs (or TBS alone) as a function of dose of urokinase. Compared to urokinase alone (TBS) or urokinase with the control antidigoxin MAb, RWR, 49C9, 70B11 and 77A3 all accelerate clot lysis. However, 49C9, 70B11 and 77A3 appear to be significantly more potent than RWR in these assays. To examine the increase in fibrinolytic potency of urokinase achieved by one of these antibodies, dose response studies were performed in the absence or presence of MAb 77A3. FIG. 4 shows that MAb 77A3 markedly increases the potency of lysis of urokinase by roughly 100-fold.

As a means of further discriminating among the functional and epitope binding specificities of these MAbs, their ability to inhibit the α2AP from different animal species in plasma clot lysis assays was examined. The results of these assays are summarized in Table 2, below. In the different species of animal plasmas tested, RWR appeared to inhibit only human α2AP. In contrast, the other MAbs showed a broader species cross-reactivity and ability to inhibit nearly all primate and some non-primate α2APs.

TABLE 1

Effect of Different MAb Inhibitors on the binding of $^{125}$I-α2AP to Immobilized MAbs.

| | Immobilized MAb | | | |
|---|---|---|---|---|
| Inhibitor | RWR | 49C9 | 70B11 | 77A3 |
| RWR | + | – | – | – |
| 49C9 | – | + | + | + |
| 70B11 | – | + | + | + |
| 77A3 | – | + | + | + |
| anti-digoxin | – | – | – | – |

To wells of a microtiter plate containing an immobilized MAbs was added $^{125}$I-α2AP and a different competitor MAbs. A "+" indicates that the competitor inhibited the binding of $^{125}$I-α2AP to the plate, whereas a "–" indicates that there was no inhibition.

TABLE 2

The cross reactivity of MAbs with different α2-antiplasmins.

| Species | RWR | 49C9 | 70B11 | 77A3 |
|---|---|---|---|---|
| HUMAN | ++ | ++ | ++ | ++ |
| Baboon | – | ++/+ | ++/+ | ++ |
| Grn Monkey | – | ++ | ++ | ++ |
| Dog | – | + | +/– | + |
| cynamologus | – | ++ | ++ | ++ |
| marmoset | – | + | + | + |
| ferret | – | +/++ | +/– | +/++ |
| guinea pig | – | – | +/– | +/– |
| gerbil | – | – | – | – |

The crossreactivity of each MAb was determined by its ability to accelerate the lysis of that species' plasma clots. A "–" indicated that the MAb did not accelerate plasma clot lysis, a "+" indicated modest effects, and "++" indicates significant acceleration of plasma clot lysis (i.e., significant functional crossreactivity).

EXAMPLE 2

In Vivo Study of Pulmonary Embolism

A. Materials

Materials were obtained from the following suppliers: rt-PA with a specific activity of 580,000 IU/mg, Genentech (South San Francisco, Calif.); ketamine (100 mg/ml), Fort Dodge Laboratories (Fort Dodge, Iowa); acepromazine maleate, Fermenta Animal Health Co. (Kansas City, Mo.); heparin (1000 U/ml), Elkins-Sinn Inc. (Cherry Hill, N.J.); sodium iodide, Aldrich Chemical Co. (Milwaukee, Wis.); calcium chloride, Mallinckrodt (Paris, Ky.); normal saline for intravenous use, Travenol Laboratories (Deerfield, Ill.); α2AP assay kit, Stachrom (Asnières, France); purified α2AP and fibrinogen, American Diagnostica (Greenwich, Conn.); goat antimouse antibody, Cappel Organon Technika (Durham, N.C.); human plasma pooled from random donors, Massachusetts General Hospital (Boston); bovine thrombin, Parke-Davis (Morris Plains, N.J.); $Na^{125}I$, Dupont-NEN (Cambridge, Mass.); Bard Parker surgical blade, Becton Dickinson (Franklin Lake, N.J.); 4.0 silk sutures, American Cyanamid Co. (Danbury, Conn.); SURFLO IV catheter and 20 gauge 1¼-inch VENOJECT tubes with $K_3EDTA$, Terumo Medical Corp. (Elkton, Md.); sterile three-way stopcock, Mallinckrodt Critical Care (Glens Falls, N.Y.); auto syringe infusion pump, Baxter Health Care Corp. (Hooksett, N.H.); infusion pump tubing and microbore 60-inch extension set, McGaw of Puerto Rico (Sabana Grand, Puerto Rico); surgical instruments, VWR (Boston); tubing, Namic (Glens Falls, N.Y.); ferrets (~0.8–1 kg), Marshall Farms (New York, N.Y.); aprotinin, Sigma (St. Louis, Mo.); and microcentrifuge tubes, National Scientific Supply Co. (San Rafael, Calif.).

B. In Vitro Clot Lysis Assays

Pooled, fresh-frozen, citrated ferret plasma (1100 $\mu$l) was mixed with 15 $\mu$l of $^{125}$I-labeled human fibrinogen (~40,000 cpm/clot). Ferret plasma (35 $\mu$l) was mixed with 35 $\mu$l of Tris-buffered saline (TBS) containing 10 mM $CaCl_2$ and thrombin (1 U/ml) in twelve 65-mm plastic tubes and clotted for 1 hour at 37° C. The clots were washed in TBS, the supernatant was removed, and then 100 $\mu$l of TBS or 25 $\mu$g of purified MAb (RWR or 77A3) was added to tubes in duplicate. Clot lysis was initiated by adding 0.1 U of rt-PA per tube. The clots were incubated at 37° C. for 5 hours and the amount of lysis was determined by sampling for the release of radiolabeled fibrin degradation products into the supernatant, as described (Reed, G. L. III et al., *Proc. Natl. Acad Sci. USA* 87:1114–1118 (1990)).

C. Pulmonary Embolism Experiments

Male ferrets were anesthetized by intramuscular injection (0.4 ml) of a mixture of ketamine and acepromazine (two parts acepromazine [10 mg/ml] to one part ketamine [100 mg/ml]). Intraperitoneal injections were repeated as necessary to keep the animals anesthetized. After an anterior midline incision had been made in the neck, the jugular vein and the carotid artery were exposed by blunt dissection and cannulated with 20G catheters that were secured at the proximal and distal ends with 4-0 silk sutures. The catheters were capped with three-way stopcocks.

Pooled, citrated human plasma was mixed with $^{125}$I-fibrinogen to achieve ~1,000,000 cpm/ml. Individual clots were formed by mixing $^{125}$I-fibrinogen-labeled plasma (45 $\mu$l) with 2.5 $\mu$l of bovine thrombin (100 U/ml) and 2.5 $\mu$l of calcium chloride (0.4 M). These clots were incubated at 37° C. for 90 minutes, compressed, and washed thoroughly with saline three times to remove unbound proteins. The radioactive content of the clots was measured in a gamma counter immediately before clot injection. Blood samples were drawn at base line and at the end of the experiment. Sodium iodide (10 mg) was injected to block thyroid uptake. Clots were embolized into the lungs by injection through the internal jugular vein. Ferrets weighing less than 1 kg received three clots; those weighing 1 kg or more received four clots. Successful embolization was evidenced by the accumulation of radioactivity in the thorax. After the clots had been injected, the ferrets were turned on their sides to ease breathing.

All animals received weight-adjusted heparin at 100 U/kg (bolus), a dose sufficient to keep the activated partial thromboplastin time (aPTT) above 150 seconds throughout the procedure. The α2AP inhibitor (sterile-filtered, 14 mg/ml in saline) or a purified control MAb (antidigoxin) was given intravenously as a single dose (22.5 mg/kg). The rt-PA was given as a continuous infusion over 2 hours (1 or 2 mg/kg in 5 ml normal saline). Animals were observed for a total of four hours after pulmonary embolization and then killed by lethal injection of anesthesia or by $CO_2$ inhalation. The thorax was dissected and all intrathoracic structures were removed for gamma counting to detect residual thrombi. The percentage of clot lysis was determined for each ferret by dividing the total residual radioactivity in the thorax (cpm) by that in the initial thrombi.

This experimental protocol was approved by the Harvard Medical Area Standing Committee on Animals. The Harvard Medical School animal management program is accredited by the American Association of Laboratory Animal Care, and the procedures were conducted in accordance with National Institutes of Health standards, as set forth in the Guide for the Care and Use of Laboratory Animals (DHHS Publication No. [NIH] 85–23, revised 1985), the Public Health Service Policy on the Humane Care and Use of Laboratory Animals by Awardee Institutions, and the NIH Principles for the Utilization and Care of Vertebrate Animals Used in Testing, Research, and Training.

D. Statistical Tests

The data were analyzed by a one way analysis of variance followed by a Bonferroni-Dunn procedure for multiple comparison testing.

E. Fibrinogen Assays

Blood samples were collected on $K_3EDTA$ (0.15% solution final) with aprotinin (50 kallikrein U/ml). Platelet-poor plasma was obtained by centrifugation of whole blood (Mustard, J. F. et al., *Meth. Enzymol.* 169:3–11 (1989)) and assayed for fibrinogen by the sodium sulfite method (Rampling, M. W. and Gaffney, P. J., *Clin. Chim. Acta.* 67:43–52 (1976)).

F. α2-Antiplasmin Assays

To measure α2AP levels, we collected ferret blood on sodium citrate (1/10 volume) and centrifuged it to obtain plasma (Mustard, J. F. et al., *Meth. Enzymol* 169:3–11 (1989)). The plasma was tested for functional α2AP with a chromogenic substrate assay for plasmin inhibition (Stachrom kit) as described (Reed, G. L. III et al., *Proc. Natl. Acad. Sci. USA* 87:1114–1118 (1990)).

G. Results

Figure 5:
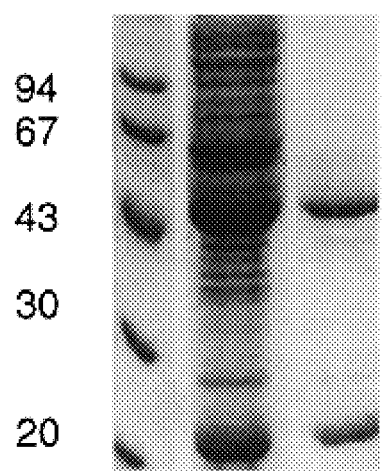
FIG. 5. Reduced SDS-polyacrylamide gel electrophoresis of 77A3 purification. Ascites containing 77A3 were harvested and purified. Lane 1, protein standards with molecular mass in kDa (left); lane 2, supernatant after precipitation with 40% ammonium sulfate; lane 3, purified 77A3. The reduced 77A3 immunoglobulin consists of bands of ~50 kDa, corresponding to the heavy chain, and ~25 kDa, corresponding to the light chain.
Figure 6:
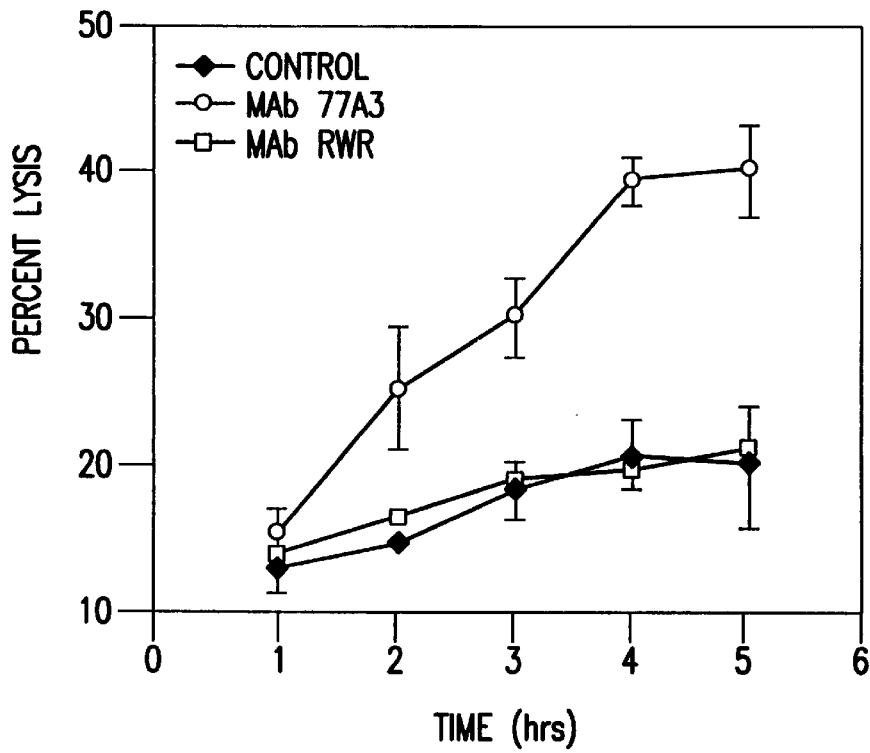
FIG. 6. Effect of 77A3 on the rate of lysis of ferret plasma clots in vitro. Ferret plasma clots formed with trace amounts of $^{125}$I-labeled human fibrinogen were incubated with 100 μl of TBS (control) or purified MAb (25 μg, 77A3 or RWR). Clot lysis was initiated by adding 0.1 unit of rt-PA per tube. The clots were incubated at 37° C. and the amount of lysis was determined by sampling for the release of radiolabeled fibrin degradation products into the supernatant as described (Reed, G. L. III et al., Proc. Natl. Acad. Sci. USA 87:1114–1118 (1990)).

From a panel of hybridomas we selected 77A3, a MAb that bound tightly to human α2AP. MAb 77A3 was purified from mouse ascites by ion exchange chromatography, and its purity was confirmed by SDS-polyacrylamide gel analysis (FIG. 5). To study the role of α2AP in experimental pulmonary embolism in vivo, we tested purified 77A3 in several different animal plasma clot lysis assays to determine whether it could bind and inhibit a non-human α2AP. Of various small animal plasmas tested (e.g. hamster, gerbil, guinea pig, rat, etc.), 77A3 significantly crossreacted with ferret plasma. FIG. 6 compares the lytic effects of 77A3 with those of another MAb inhibitor of human α2AP, RWR (Reed, G. L. III et al., *Trans. Assoc. Am. Phys.* 101:250–256 (1988); U.S. Pat. No. 5,372,812, issued Dec. 13, 1994), and with buffer alone. FIG. 6 shows that in comparison with the control (buffer alone), 77A3 accelerated the lysis of ferret plasma clots induced by a low dose of rt-PA (0.1 unit). In contrast, RWR, which inhibits human α2AP (Reed, G. L. III et al., *Trans. Assoc. Am. Phys.* 101:250–256 (1988); U.S. Pat. No. 5,372,812, issued Dec. 13, 1994) but does not crossreact with nonhuman α2AP, had no detectable effect. This experiment indicated that 77A3 inhibited ferret α2AP and amplified ferret clot lysis in vitro.

Figure 7:
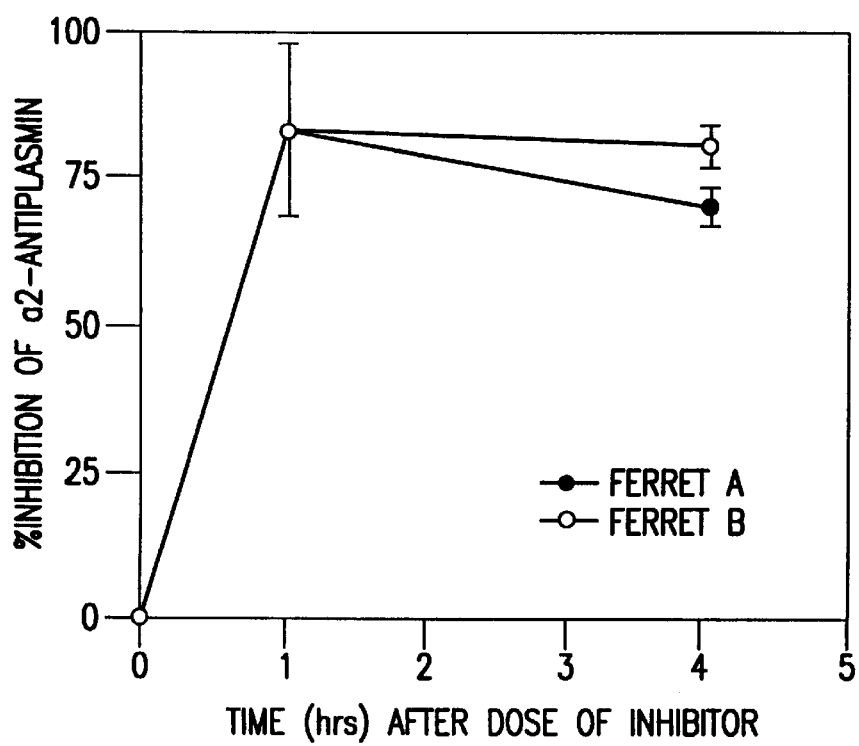
FIG. 7. Effect of in vivo administration of MAb 77A3 on functional α2AP levels in ferrets. In dose finding experiments, two anesthetized ferrets (A, B) were given 77A3 intravenously (22.5 mg/kg) and the amount of functional α2AP was measured in citrated plasma samples drawn before (time 0) and 1 and 4 hours after infusion. The data represent the mean±SD inhibition of α2AP in plasma samples.

The cross-reactivity of 77A3 allowed us to investigate the role of α2AP in a ferret model of pulmonary embolism. In humans, pulmonary embolism is usually treated with heparin (Goldhaber, S., *Chest* 107:45S–51S (1995)). Consequently, ferrets were treated with a weight-adjusted bolus dose of heparin at 100 U/kg. This dose was sufficient to keep the aPTT above 150 seconds throughout the experiment (n=3). To investigate the effects of intravenous MAb 77A3 on the activity of α2AP in the blood, we selected a dose, 22.5 mg/kg, that was in molar excess to the level of ferret α2AP. Our ex vivo measurements of ferret α2AP activity, 1 and 4 hours after intravenous dosing, showed that ~75% of ferret a2AP activity was inhibited at this dose (FIG. 7, n=2).

Figure 8:
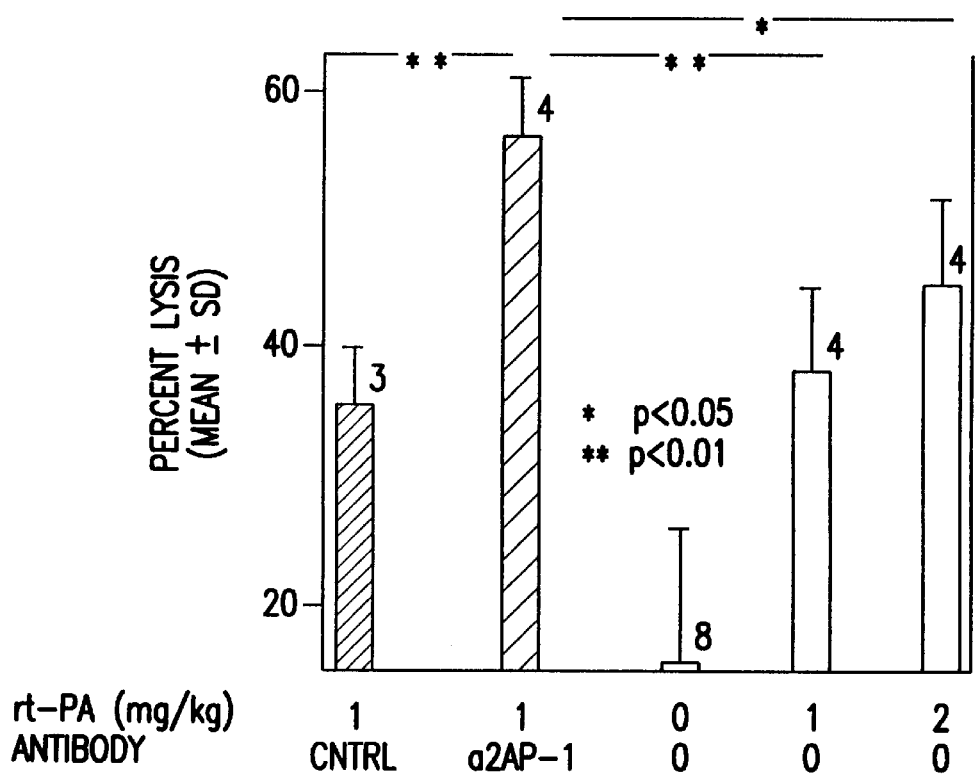
FIG. 8. Effect of rt-PA and α2AP inhibition on the lysis of pulmonary emboli in vivo. Anesthetized ferrets were given a heparin bolus (100 U/kg) and $^{125}$I-labeled fibrin clots were embolized into the lungs. After embolization, three groups of ferrets were given rt-PA (0, 1, or 2 mg/kg) over 2 hours intravenously (plain bars). Two other groups of ferrets also received rt-PA (1 mg/kg) and a control MAb (antidigoxin, black bar, 22.5 mg/kg) or a MAb that inhibits α2AP (77A3, striped bar, same dose). The graph shows the amount of lysis (mean±SD) for each treatment group. The number of ferrets in each treatment group is shown, and the P values for differences between groups are indicated.

Using heparin at 100 U/kg and 77A3 at 22.5 mg/kg, we then investigated the effect of these agents and rt-PA on the lysis of pulmonary emboli (FIG. 8). All animals received heparin. Control animals (n=8), which received no rt-PA, showed 15.6±10.5% (mean±SD) lysis of their pulmonary emboli. Animals receiving rt-PA at 1 mg/kg (n=4) over 2 hours showed 38.5±6.3% lysis, which was significantly greater than lysis obtained in those receiving heparin alone (P<0.01). Similarly, animals receiving rt-PA at 1 mg/kg and a control (antidigoxin) MAb (n=3) showed 35.2±4.6% lysis. Ferrets treated with rt-PA at 2 mg/kg (n=4) showed a minimal increase in lysis over those treated at 1 mg/kg (45.0±6.5% vs 38.5±6.3%, P<0.05). However, animals receiving rt-PA at 1 mg/kg together with the α2AP inhibitor (n=4) showed greater lysis (56.2±4.7%) than those receiving an equivalent dose of rt-PA alone (P<0.01), with or without the control (antidigoxin) MAb (P<0.01), or those receiving twice the dose of rt-PA alone (P<0.05).

Figure 9:
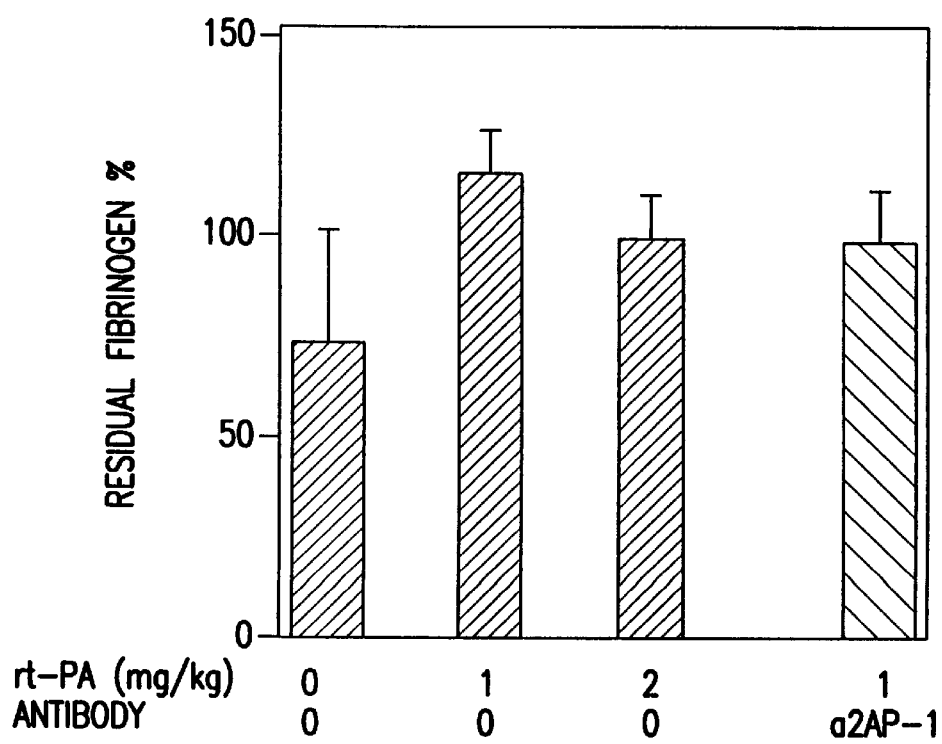
FIG. 9. Residual fibrinogen levels in animals treated with heparin, rt-PA, and an α2AP inhibitor. Blood samples were collected (on EDTA with aprotinin) from ferrets before pulmonary embolization and at the end of the experiment. Residual fibrinogen levels were measured as described (Rampling, M. W. and Gaffney, P. J., Clin. Chim. Acta. 67:43–52 (1976)). The graph shows the mean±SD percentage residual fibrinogen level for animals receiving rt-PA alone (0, 1, or 2 mg/kg; plain bars) and those receiving rt-PA and the α2AP inhibitor (striped bar).

In addition to inhibiting plasmin on the thrombus surface, α2AP and other inhibitors inactivate plasmin in the blood (Collen, D., *Eur. J Biochem.* 69:209–216 (1976); Moroi M. and Aoki, N., *J. Biol. Chem.* 251:5956–5965 (1976); Mullertz, S. and Clemmensen, I., *Biochem J.* 159:545–553 (1976)). We measured fibrinogen levels in the blood to determine if inhibition of α2AP led to nonspecific plasminolysis of a circulating clotting factor. FIG. 9 shows residual fibrinogen levels expressed as a function of their initial values in four treatment groups. In animals that received no rt-PA, fibrinogen levels varied moderately but did not diminish during the experiment. Ferrets receiving 1 mg/kg and 2 mg/kg of rt-PA alone showed no significant change in fibrinogen level. Similarly, animals receiving the combination of rt-PA and the α2AP inhibitor showed no detectable change in circulating fibrinogen levels.

H. Discussion

Clinical and experimental studies suggest that pulmonary emboli and venous thrombi resist endogenous fibrinolysis and lysis induced by plasminogen activators (Goldhaber, S., *Chest* 107:45S–51S (1995); Goldhaber, S. Z. et al., *Lancet* 2:886–889 (1986); The Urokinase Pulmonary Embolism Trial, *Circulation* 47:1–108 (1973); Goldhaber, S. Z. et al., *Am. J Med* 88:235–240 (1990); Goldhaber, S. Z. et al., *Lancet* 341:507–511 (1993)). This resistance to lysis is due in part to specific molecular factors in the thrombus that act to oppose fibrinolysis. During thrombus formation, α2AP is covalently crosslinked to fibrin by activated factor XIII (Sakata, Y. and Aoki, N., *J. Clin. Invest.* 69:536–542 (1982)). Studies in vitro indicate that when α2AP in the clot is absent or inhibited by MAbs, clots undergo spontaneous lysis (Aoki, N. et al., *Blood* 62:1118–1122 (1983); Miles, L. A. et al., *Blood* 59:1246–1251 (1982); Reed, G. L. III et al., *Trans. Assoc. Am. Phys.* 101:250–256 (1988); Reed, G. L. III et al., *Proc. Natl. Acad Sci. USA* 87:1114–1118 (1990)). Conversely, when levels of α2AP in clots are increased by supplementation in vitro, fibrinolysis is inhibited (Sakata, Y. and Aoki, N., *J. Clin. Invest.* 69:536–542 (1982)). In the present study we investigated the hypothesis that α2AP plays a major regulatory role in fibrinolysis and that it contributes to the thrombus resistance obtained in pulmonary embolism.

We measured the effect of rt-PA, with and without α2AP inhibition, on the net lysis of pulmonary emboli in ferrets. Because heparin is the established therapy for humans with pulmonary embolism, we considered animals treated with heparin alone as the control group. The weight-adjusted bolus dose of heparin given to the ferrets was sufficient to maintain a high level of anticoagulation throughout the experiment. In animals treated with rt-PA, at a dose comparable to that used in humans (1 mg/kg), lysis of pulmonary emboli was enhanced significantly in comparison with lysis in animals treated with heparin alone. Increasing the dose of rt-PA to 2 mg/kg, a dose higher than is safe in humans, led to a minimal increase in lysis. A similar plateau in the dose response for t-PA-induced lysis has been noted in experimental studies of pulmonary embolism in dogs (Werier, J. et al., *Chest.* 100:464–469 (1991)). However, specific inhibition of α2AP markedly potentiated the lysis of experimental pulmonary emboli by rt-PA (1 mg/kg), causing significantly more lysis than was seen in ferrets treated with the same dose of rt-PA: alone or with a control MAb, the lysis achieved with α2AP inhibition was also greater than that achieved in ferrets treated with high-dose rt-PA (2 mg/kg). At the same time, despite the higher total lysis obtained in animals treated with the α2AP inhibitor, there was no significant consumption of circulating fibrinogen. In these studies of experimental pulmonary embolism, α2AP played an important role in thrombus resistance to lysis induced by rt-PA. Further studies will be necessary to establish the relative quantitative roles of circulating and thrombus bound α2AP in this process.

Besides α2AP, other molecular factors may regulate the thrombus resistance of pulmonary emboli. A leading candidate is PAI-1, a serine protease inhibitor of t-PA and urinary-type plasminogen activator (u-PA or urokinase) (Stringer, H. A. and Pannekoek, H., *J. Biol. Chem.* 270:11205–11208 (1995); Carmeliet, P. et al., *J. Clin. Invest.* 92:2756–2760 (1993); Lang, I. M. et al., *Circulation* 89:2715–2721 (1994); Marsh, J. J. et al., *Circulation* 90:3091–3097 (1994)). Unlike α2AP, PAI-1 is not specifically crosslinked to fibrin in the thrombus, although it has been shown to bind to fibrin in vitro (Stringer, H. A. and Pannekoek, H., *J. Biol. Chem.* 270:11205–11208 (1995)). By adding recombinant PAI-1 to developing thrombi, Marsh et al. (Marsh, J. J. et al., *Circulation* 90:3091–3097 (1994)) have shown that PAI-1-enriched clots can suppress the spontaneous lysis of pulmonary emboli in a canine model; however, the role of PAI-1 in the lysis of autologous thrombi was not investigated. Pathologic studies of pulmonary emboli extracted by thrombectomy have suggested that PAI-1 expression increases in the endothelial cells at the margins of fresh thrombi but is not detectable in the thrombi themselves (Lang, I. M. et al., Circulation 89:2715–2721 (1994)). Since PAI-1-deficient mice (by gene deletion) are less likely than regular mice to develop venous thrombosis induced by endotoxin (Carmeliet, P. et al., J. Clin. Invest. 92:2756–2760 (1993)), the expression of PAI-1 in endothelial cells at the margin of the developing thrombus may be functionally important. Nonetheless, the role of PAI-1 in thrombus resistance to pharmacologic plasminogen activators is less clear: in patients given t-PA, the inhibitory capacity of PAI-1 is overwhelmed completely (Lucore, C. L. and Sobel, B. E., Circulation 77:660–669 (1988)), and thrombus resistance is also observed in patients given streptokinase, against which PAI-1 has no effect.

Another potential cause of thrombus resistance in pulmonary embolism is activated factor XIII. Several studies in vitro suggest that this coagulation enzyme renders the fibrin in clots more resistant to degradation by plasmin by crosslinking fibrin chains together and by crosslinking a2AP to fibrin. (Sakata, Y. and Aoki, N., J. Clin. Invest. 69:536–542 (1982); Robbie, L. A. et al., Thromb. Haemostas. 70:301–306 (1993); Francis, C. W. and Marder, V. J., J. Clin. Invest. 80:1459–1465 (1987); Jansen, J. W. C. M. et al., Thromb. Haemostas. 57:171–175 (1987); Reed, G. L. et al., Trans. Assoc. Am. Phys. 104:21–28 (1991)) However, little is known about activated factor XIII and thrombus resistance in vivo. This is probably due to the fact that a potent inhibitor of factor XIII function has only recently become available (Reed, G. L. and Lukacova, D., Thromb. Haemostas. 74:680–685 (1995)). One study has suggested that when factor XIII is partially inhibited, coronary thrombi lyse at accelerated rates in response to t-PA (Shebuski, R. J. et al., Blood 75:1455–1459 (1990)). This observation argues that factor XIII, through its effects on fibrin-fibrin and α2AP-fibrin crosslinking, also contributes to thrombus resistance.

Improving the lysis of thrombi in patients with pulmonary embolism and deep venous thrombosis remains a challenge. Unfortunately, increasing the dose of plasminogen activators is not a promising approach. High dose t-PA has been associated with an unacceptable increase in the risk of cerebral bleeding (Passamani, E. et al., J. Am. Coll. Cardiol. 10:51B–64B (1987)). In addition, in the present study and others (Werier, J. et al., Chest. 100:464–469 (1991)), high-dose t-PA ($\geq$2 mg/kg) produced only minimal increases in net lysis. The current FDA-approved doses of urokinase and streptokinase cause plasminogen "depletion"; thus, increasing the doses of these agents is also not likely to have an effect on net lysis (Onundarson, P. T. et al., J. Lab. Clin. Med. 120:120–128 (1992)). Several potent inhibitors of thrombin generation and activity are under development. Although these agents may further reduce the formation of new thrombi, they will not directly improve lysis of the large thrombi that typically exist in patients at the time they are diagnosed. These considerations suggest that fundamental insights into the molecular factors that oppose physiologic or pharmacologic lysis in thrombi will be necessary to spark improved treatments for venous thromboembolism. The results of the present study indicate that α2AP is a major contributor to thrombus resistance in experimental pulmonary embolism, and they suggest that inhibiting α2AP might improve lysis in patients with thrombotic disease.

EXAMPLE 3

Cloning and Sequencing of Antibody cDNA

A. Amino Terminal Sequences of Antibodies

Monoclonal antibodies (49C9, 70B11 and 77A3) were expanded into ascites and purified by ion exchange chromatography on DEAE Affigel Blue or by protein A agarose as described in Lukacova, D. et al., Biochemistry 30:10164–10170 (1991). The purified MAbs (15 µg) were subjected to SDS-PAGE on 10% minigels (BioRad, Hercules, Calif.). The protein samples were electroblotted to PVDF membranes (Millipore, Bedford, Mass.) using semi-dry technique (Kyhse-Anderson, J., J. Biochem. Biophys. Meth. 10:203–209 (1984)) at 4° C. for 2 hrs at 75 milliamps (Millipore electroblotter). The bands were stained with Ponceau Dye (Sigma, St. Louis) and excised. The amino terminal sequences of the light chain of the antibodies are shown in FIG. 10 (SEQ ID NOS: 1–3).

B. Molecular Cloning of Antibody cDNA

Cloned hybridoma cell lines 49C9, 70B11 and 77A3 were grown in 150 mm tissue culture plates in 20% fetal bovine serum in Dulbecco's modified Eagle's medium with 4.5 g/l of glucose and penicillin and streptomycin. The cells were harvested and centrifuged at 1200 rpm for 7 min. The cell pellet was resuspended in sterile phosphate buffered saline (pH 7.4) and re-centrifuged. Then 5 ml of RNAzol (Teltest, Friendswood, Tex.) was added and the pellet was homogenized for 2 min. Chloroform (500 µl) was added and the mixture was vortexed and left to incubate on ice for 15 min. The samples were centrifuged at 12,000 rpm for 15 min. The aqueous layer was mixed with 4.5 ml of isopropanol and vortexed. The mixture was precipitated at −70° C. for 90 min. and recentrifuged at 12,000 rpm for 15 min. The pellet was washed in 2 ml of 70% ethanol in DEPC-treated water. After repeat centrifugation, the supernatant was removed and the pellet air-dried. The pellet was dissolved in 200 µl of diethyl-pyrocarbonate (DEPC)-treated water and 20 µl of 3 M NaCl and 800 µl of ethanol were added. The mRNA was precipitated overnight at −70° C. and the pellet resuspended in DEPC-water.

The cDNA corresponding to the light and heavy chain sequences were isolated by primer guided reverse transcription followed by polymerase chain reaction as described (Gene Amp Thermostable rTth Reverse Transcriptase RNA PCR kit (Perkin-Elmer Cetus, San Francisco, Calif.). The light chain mRNA was primed for reverse transcription with a 3' primer (5' N6GAATTCACTGGATGG TGGGAA-GATGGA 3' (SEQ ID NO:22)) corresponding to the constant region of the light chain ( Coloma, M. J., et al., Biotechniques 11:152–154, 156 (1991)) and the heavy chain was primed with a 3' primer (5' N6GAATTCA(TC)CTCCACACACAGG(AG)(AG)CCAGTGGATAGAC 3' (SEQ ID NO:23)) corresponding to the constant region of the heavy chain (Coloma, M. J., et al., Biotechniques 11:152–154, 156 (1991)). Because the light chain amino terminal sequences were known, a specific primer corresponding to the likely 5' sense sequence was used (5' ACTAGTCGACATGAGTGTGCTCACTCAGGTCCTGG (GC)GTTG 3' (SEQ ID NO:24); Jones, S. T., and Bendig, M. M., Bio/Technology 9:88–89 (Erratum) (1991)) for cDNA amplification. For cloning of the heavy chain, mouse heavy chain variable primers 1–12 were used as described (Jones, S. T., and Bendig, M. M., Bio/Technology 9:88–89 (Erratum) (1991)). All heavy chains amplified best with primer 9; though lesser amplification was also seen with primers 12, 10 and 6. The PCR products were isolated by low melt agarose fractionation and ligated into a vector. The light chain PCR product was ligated into PCR II vector (Invitrogen, San Diego, Calif.) The heavy chain PCR product from primer 9 was ligated into PCR II.1 vector (Invitrogen, San Diego, Calif.). After transformation, the plasmid DNA was isolated and subjected to restriction digestion with EcoR1. Two clones from each heavy and light chain were expanded and the DNA harvested. Both strands of the cDNA clones were sequenced using T7 and M13 primers with an ABI Prism automated sequencing apparatus. The cDNA sequences and deduced amino acid sequences are shown in FIGS. 11–16 (SEQ ID NOS:4–15).

EXAMPLE 4

Preparation and Characterization of Chimeric and Humanized Antibodies

In designing the sequence for a chimeric or humanized antibody, there are many parameters to consider. In the constant regions, a whole antibody may be made, or an antibody fragment (Fab and Fab'2) can be made. The constant regions may be murine or human. It is an accepted practice to replace murine constant regions with human constant regions, thus forming a "chimeric" antibody. Chimeric antibodies are less immunogenic than murine antibodies and are thus more acceptable in the clinic.

The subclass of the antibody must also be considered. It is most common to express recombinant antibodies as IgGs, but within this class, one must choose amongst recombinant chimeric human IgG1, IgG2, IgG3, and IgG4. These subclasses have different biological properties. The present inventors took a conservative approach of using IgG2 because 1) the strong complement activating properties of IgG1 and IgG3 were not needed for this antibody and 2) IgG2 may be more straightforward to manufacture than IgG4. Any of the other subclasses could be made with the same 'specificity following similar strategies.

There are also parameters to consider in designing the variable region. The antibodies could be constructed to be chimeric or humanized. The chimeric antibody (murine V region, human constant region) is a more conservative approach, and virtually guarantees very similar antigen-binding activity to the murine antibody. With humanization, there is the risk of reducing the affinity and/or biological activity of the antibody, but it can be presumed that the antibody will be less immunogenic. The present inventors have produced chimeric antibody as well as three forms of the humanized antibody.

Depending upon the strategy taken, humanization of any particular antibody can result in many different variable regions. At the simplest level, humanization consists of choosing a human variable region to serve as a template, and then deciding which residues should be "human" and which "murine". Thus, the choice of both the human template and which residues to maintain as human will affect the final sequence.

In general, the strategy the present inventors have taken is to choose from among the human germline variable region genes for the templates. Alternatively, one can choose from rearranged variable region genes, both those which have and have not undergone somatic mutation. The rationale for the first strategy is that somatic mutations can introduce immunogenic epitopes, while germline genes would have less potential for doing so. The selection was further limited to germline genes which are known to be rearranged and expressed as functional proteins in humans.

The choice of which germline gene to use as template is governed by the overall sequence similarity between the murine sequence and the human sequence; the structural similarities between the two sequences (Chothia and Lesk, J. Mol. Biol. 196:901 (1987)); the anticipated ability of the chosen heavy chain template to pair with the chosen light chain template; and the presence of the germline gene in the majority of humans. The choice of which residues should be murine is governed by which residues are thought to come in contact with antigen and which are necessary to maintain the positioning and orientation of those residues which might contact antigen.

Variable regions were assembled from oligonucleotides and inserted into expression vectors containing the human gamma 2 constant region (for the VH region) and human kappa constant region (for the VL region). Heavy and light chain vectors were verified by nucleotide sequence and ability to direct the synthesis of antigen binding immunoglobulin (Ig) in COS cells (transient expression). Selected heavy and light chain vectors were then cotransfected into CHO cells to produce stable cell lines expressing the chimeric and humanized antibodies. Antibody was purified and tested for activity by antigen binding ELISA, ability to block the inhibitory activity of α2-AP in a plasmin assay, and ability to facilitate lysis of human clots by urokinase.

A. Construction of Chimeric and Humanized Antibody Vectors

A functional light chain variable region is formed by the rearrangement and juxtaposition of a V gene segment and J gene segment. Therefore, it was necessary to find the best match for each of these segments and combine them to form a human template. A FASTA search (using the Wisconsin Package Interface) of amino acids 1–95 (Kabat numbering system; V gene proper) of murine 77A3 (m77A3) light chain against a database of human Vk germline genes showed that m77A3 is clearly most similar to the human VkI subgroup (69.2% –71.6% identity vs less than 60% identity to sequences outside this subgroup). From among the Vk I sequences, the sequence with GenBank accession #X59312 (also known as the O2/)12 gene) was chosen as a likely candidate because of the match with structurally important positions and because of its prevalent expression in humans. The human template for the light chain was completed by the addition of the human Jk2 sequence. This J region was chosen because of its high degree of similarity with the murine J region of 77A3.

A functional heavy chain variable region is formed by the rearrangement and juxtaposition of a V gene segment, a D gene segment, and a J gene segment. Therefore, it was necessary to find the best match for each of these segments and combine them to form a human template. A FASTA search (using the Wisconsin Package Interface) of amino acids 1–94 (Kabat numbering system; V gene proper) of murine 77A3 heavy chain against a database of human VH germline genes showed that m77A3 is clearly most similar to the human VH7 family (77% identity) with the human VH1 family having the next best match (about 60% identity). The human VH7 family is mostly composed of pseudogenes; the only active gene (7-04.1, Accession #X62110) is polymorphic in the human population (i.e. not all people have it) and therefore, in some people, this V gene could be 5 more immunogenic than others. As an alternative human template for the heavy chain, the V gene with accession number Z12316 (1~14 gene) was chosen. This sequence is very similar to 7-04.1 except for the H2 loop and FR3 region. A human template for the D region was not considered because this region lies entirely within the H3 loop, the sequence of which is generally pivotal for antigen binding and therefore likely to entirely follow the murine sequence in a humanized antibody. The human template for the heavy chain was completed by the addition of the human JH5 sequence. This J region was chosen because of its high degree of similarity with the murine J region of 77A3.

Following the selection of human templates for the heavy and light chain variable regions, it was necessary to determine which positions should follow the murine sequence vs which positions should follow the human sequence. The following criteria were used in selecting positions to follow the murine sequence: all positions falling within the CDR loops; all positions known to influence the conformation and/or spatial position of CDR loops (so called structural determinants; Chothia and Lesk, *J. Mol. Biol.* 196:901 (1987), Lesk and Tramontano, in: *Antibody Engineering,* W. H. Freeman and Co., pp.7–38 (1992)); residues which were close enough to interact with residues in the CDR loops; and residues at or proximal to the VH-VL domain interface. All other residues followed the human sequence. These items are discussed in greater detail below.

Figure 18B:
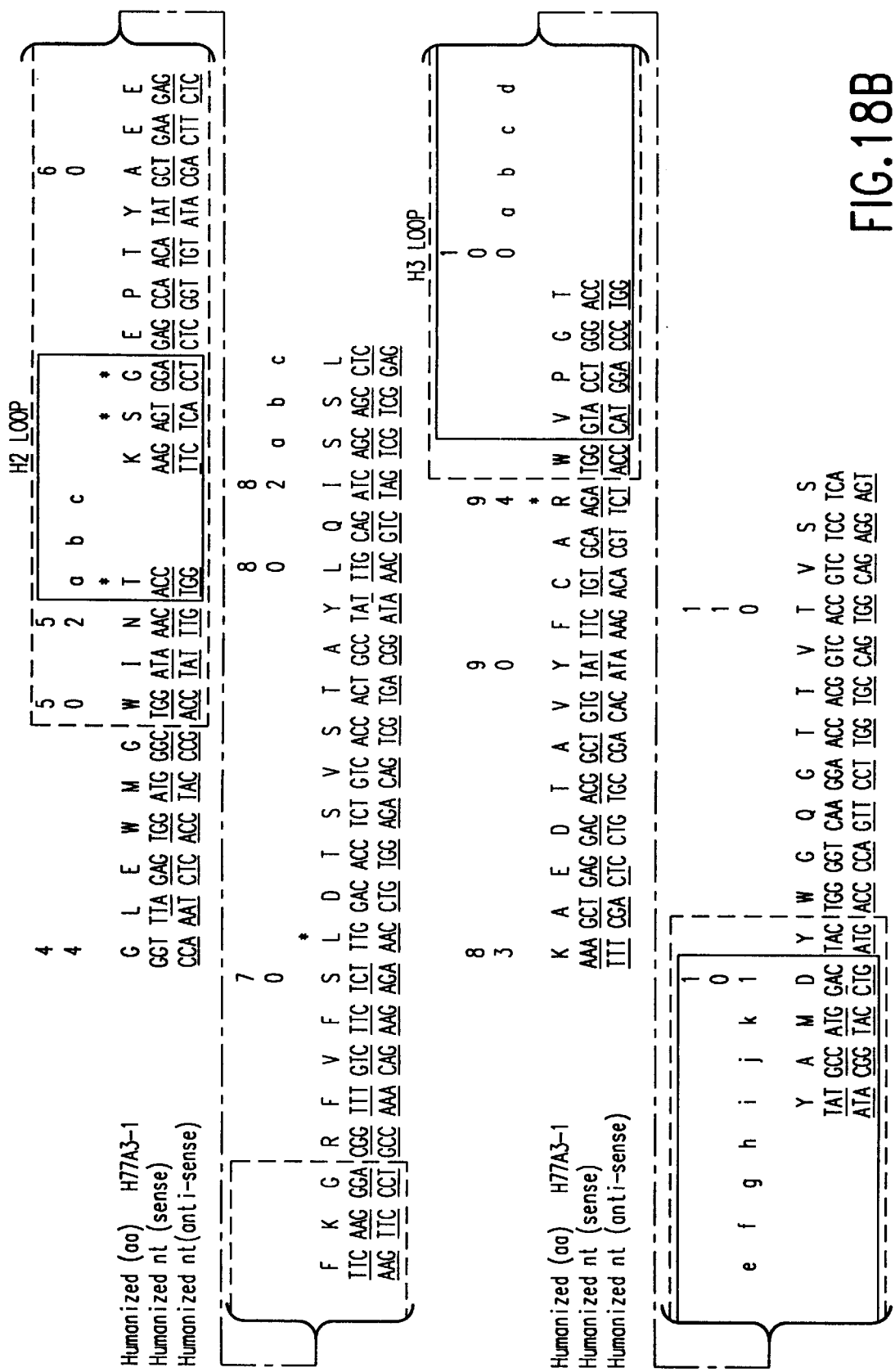
Figure 19A:
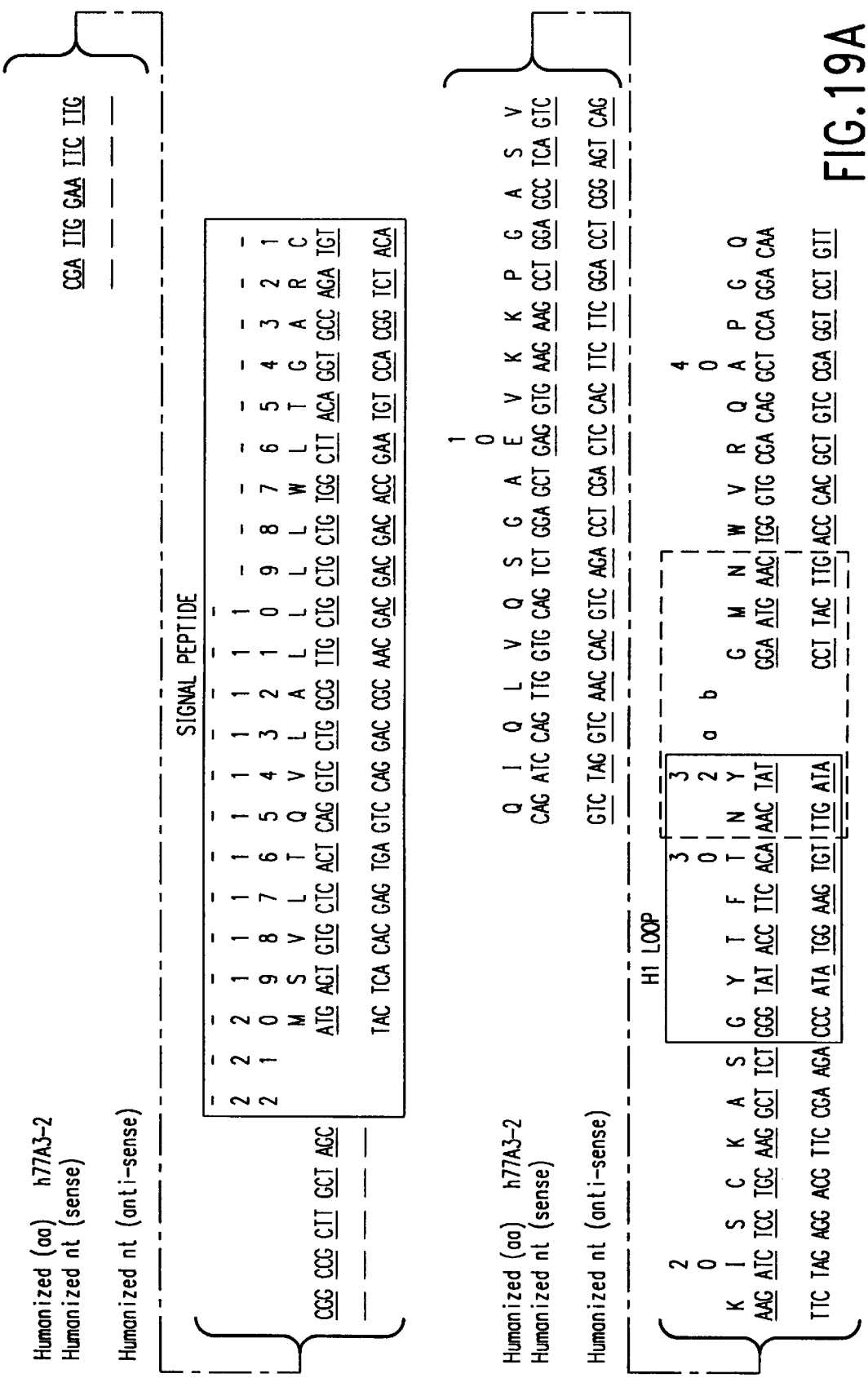
FIGS. 19A–B. The cDNA sequence (SEQ ID NO:20) and corresponding amino acid sequence (SEQ ID NO:21) of humanized 77A3-2 heavy chain. Positions falling within the CDR loops are shown enclosed within the boxes with solid borders.
Figure 19B:
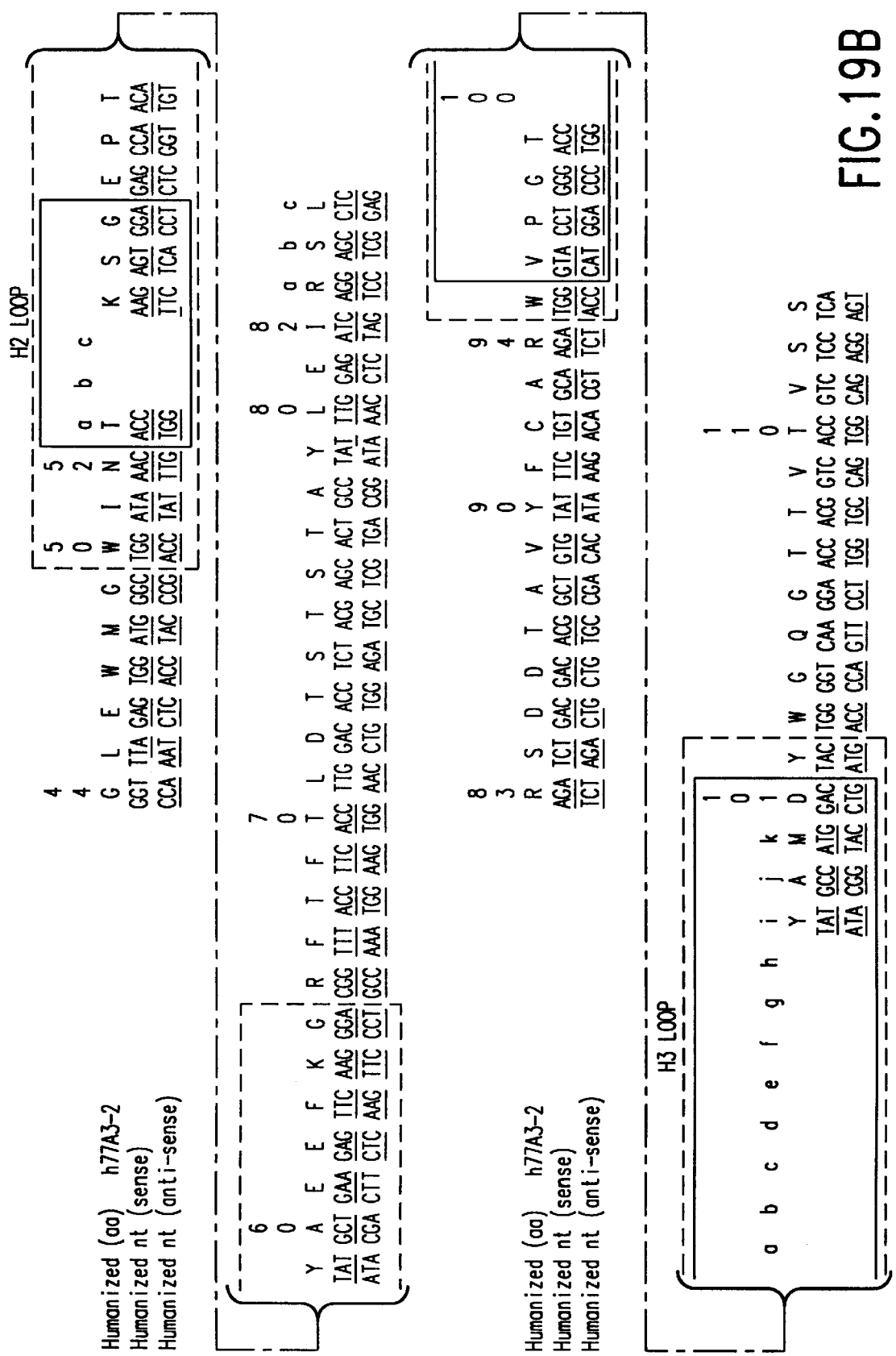

Positions falling within the CDR loops are shown enclosed within the boxes with solid borders and structural determinants are marked with an * in the row below the position number in FIGS. 17–19.

In order to determine which residues were close enough to interact with the CDR loops, it was necessary to generate an approximate molecular model of the Fv region of murine 77A3. The molecular model was built based on the combined variable light chain of an anti-lysozyme mAb (D1.3) and the variable heavy chain of an anti-neuraminidase mAb (1 ncca) as structural template. CDR loop sequences were assigned to canonical loop conformations and a possible conformation for CDR H3 was extracted form the Protein Data Bank. The modeling building protocol followed procedures described by Bajorath & Novotny (*Therapeutic Immunol.* 2:95–105 (1995)). Likewise, residues at or proximal to the VH-VL domain interface were identified and the murine residues were used for the humanized antibody. In all, for h77A3-1 heavy chain, h77A3-2 heavy chain, and for the common light chain there were 7, 18, and 11 murine residues, respectively, used outside of the CDR loops.

In order to prepare vectors encoding these chains, the amino acid sequence must be back translated into nucleotide sequence. For the most part, this was done simply by using the nucleotide sequence from the human template in cases where the amino acid residue is derived specifically from the human template; otherwise, the nucleotides from the murine sequence were used. At a few positions, silent substitutions were made in order to eliminate restriction sites.

Finally, signal peptides must be added to the sequence. For both the chimeric and humanized light chains, signal peptides corresponding to that of the murine 77A3 light chain were used. For the chimeric and humanized heavy chains, the same signal peptide as for the light chains was used. Alternatively, signal peptides corresponding to that of murine 77A3 VH or any other signal peptide can be used in the chimeric and humanized heavy chains.

Two humanized antibodies were created: h77A3-1 and h77A3-2. A third version of the humanized heavy chain was created by including an oligonucleotide designed for h77A3-1 in the construction of h77A3-2. This resulted in a hybrid molecule that was identical to h77A3-2 except for amino acids Ser and Leu at positions 9 and 11 of the heavy chain. One chimeric antibody, c77A3, was generated.

Figure 17A:
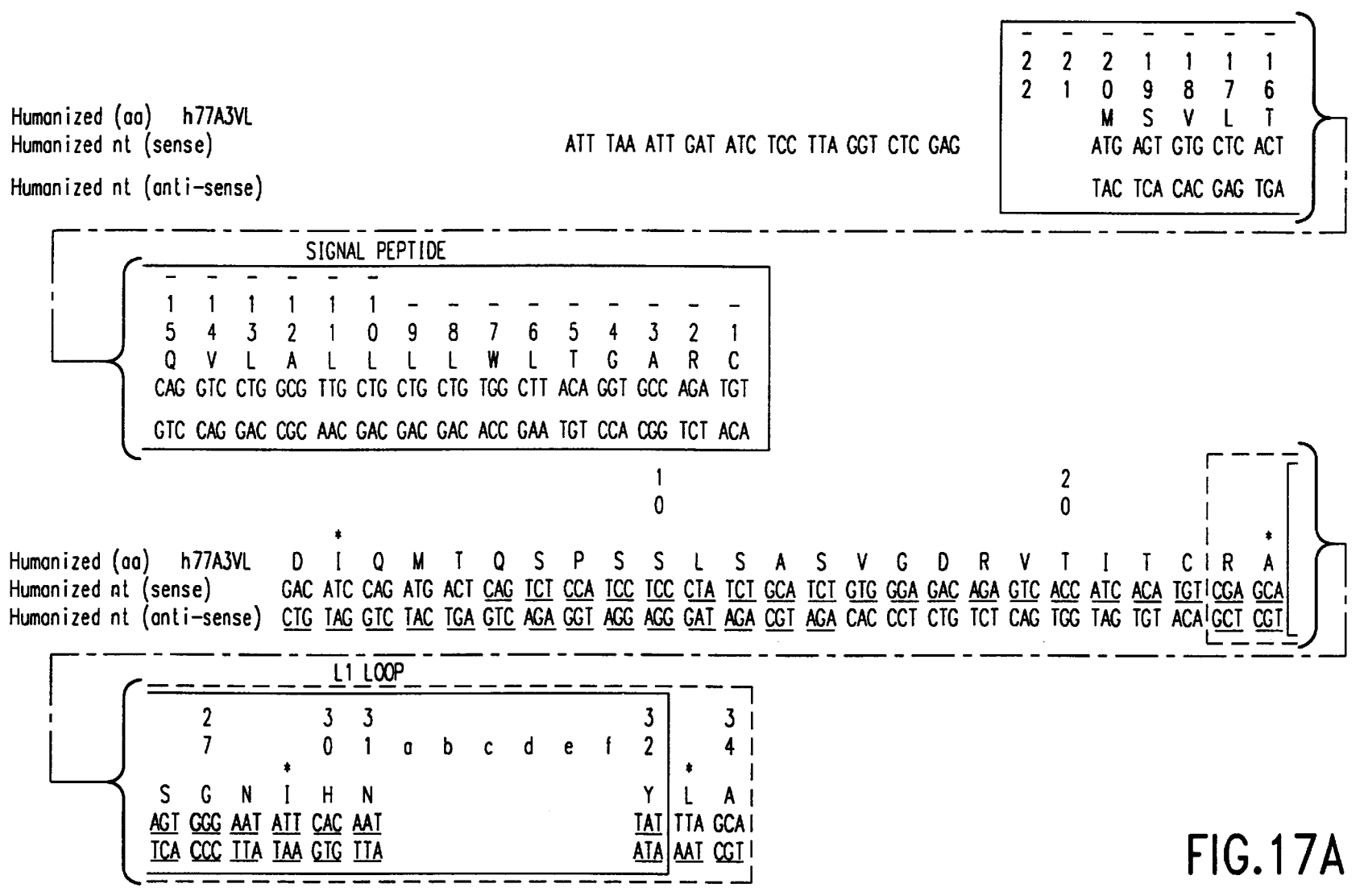
Figure 17B:
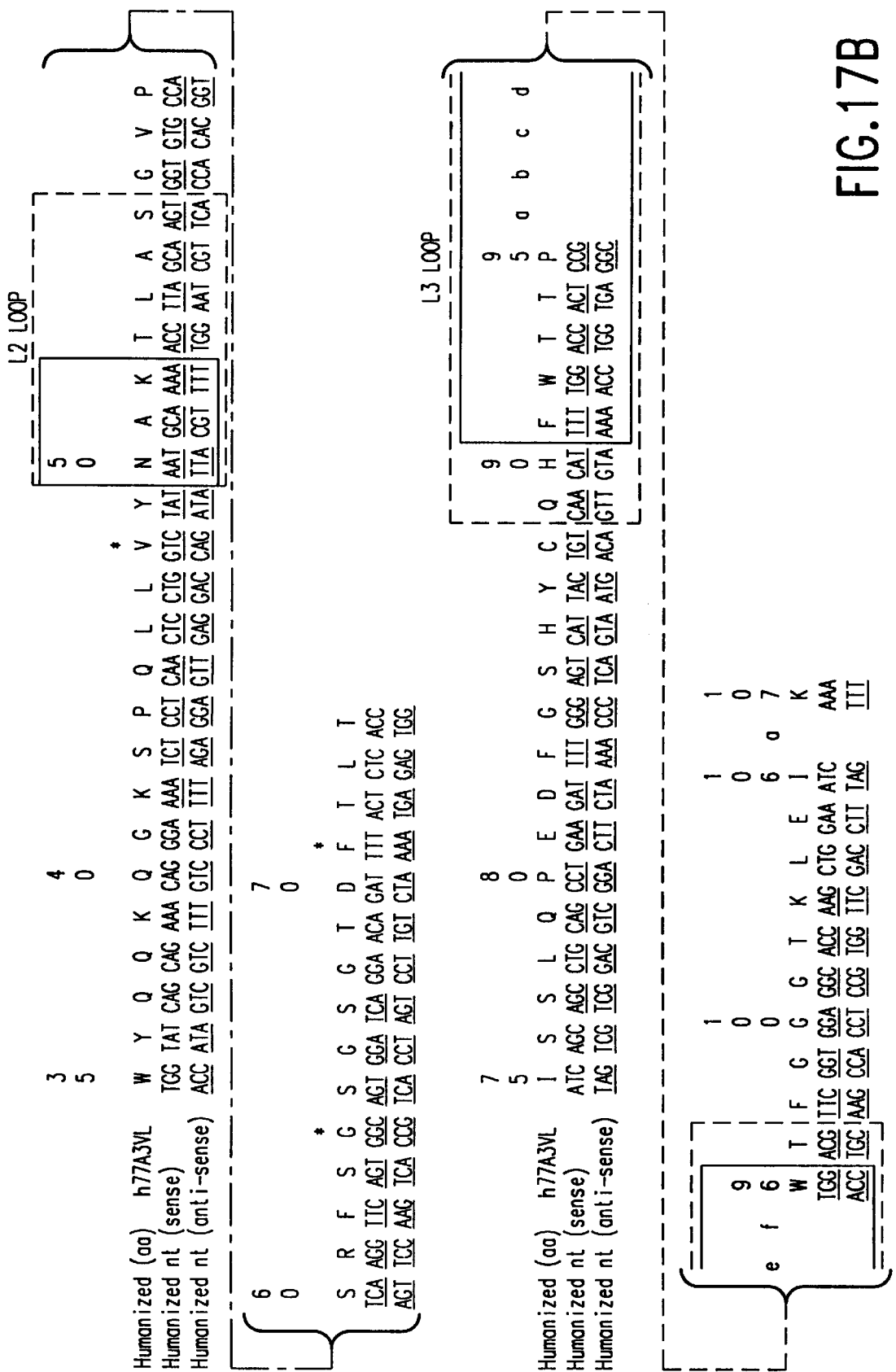

Amino acid and nucleotide sequences of h77A3-1 and h77A3-2 heavy and light chains are shown in FIGS. 17–9 (SEQ ID NOS:16–21). The common light chain is shown in FIG. 17 (mature protein is amino acid residues 1 to 107 of SEQ ID NO:17). The heavy chain of h77A3-1 is shown in FIG. 18 (mature protein is amino acid residues 1 to 119 of SEQ ID NO:19). The heavy chain of h77A3-2 is shown in FIG. 19 (mature protein is amino acid residues 1 to 123 of SEQ ID NO:21).

Expression vectors for chimeric and humanized 77A3 light and heavy chains were prepared in three stages: (1) construction of cassettes containing human light or heavy chain constant region genes (pD16-hCka and pD20-hγ2a, respectively); (2) preparation of a PCR product containing the light or heavy chain variable region; and (3) insertion of the variable region into the appropriate expression cassette.

Plasmid pD13 was constructed and derived from the pcDNA3 plasmid (Invitrogen) in two steps. The SV40 promoter/enhancer and neomycin resistance genes were removed from pcDNA3 by digestion with NaeI and isolation of the 3.82 kb fragment. These genes were replaced by the SV40 promoter/enhancer and dhfr gene from pSV2-dhfr. The DNA containing the pSV2-dhfr sequence was isolated as a 1.93 kb fragment after digestion with PvuII and BamHI. The 3.82 and 1.93 kb fragments were ligated together and used to transform MC1061 bacteria following filling in the protruding ends of the 1.93 kb fragment from pSV2-dhfr. The correct product (designated pD12) was confirmed by the release of an 890 bp fragment following HindIII digestion.

The polylinker was replaced with alternative restriction sites by digesting the resultant vector above with Asp718 and Bsp1201. The following oligonucleotides were annealed to the vector and cloned by ExoIII cloning (K. Hsiao, *Nucl. Acid. Res.* 21:5528–5529 (1993)) to complete the plasmid pD13:

5' TAGGGAGACCCAAGCTTGGTACCAATT-TAAATTGATATCTCCTT AG GTCTCGAGTCTCTA-GATAACCGGTCAATCGATTGGGATTCTT 3' (SEQ ID NO:25) and 5' GACACTATAGAATAGGGCCCTTCCGCG-GTTGGATCCAACACGT GAAGCTAGCAAGCGGC-CGCAAGAATTCCAATCGATTGACCGGTTA 3' (SEQ ID NO:26). The resulting plasmid was used to transform *competent E. coli* DH5α and the correct product was confirmed by sequencing the polylinker region.

Plasmid pD16 was derived from the pcDNA3 plasmid (Invitrogen) in a series of steps which: add a polylinker sequence upstream of the CMV promoter for linearization; delete the SV40 promoter/enhancer and neomycin resistance gene and replace them with the histone H3 transcription termination sequence, the SV40 promoter (enhancer deleted) and DHFR gene; and insert the gastrin transcription termination sequence upstream of the CMV promoter.

pcDNA3 (Invitrogen) was digested with BglII and annealed to the following oligonucleotides:
5' primer:
5'-GATCTGCTAGCCCGGGTGACCTGAGGCGCGCC TTTG GCGCC-3' (SEQ ID NO:27);and
3' primer:
3'-ACGATCGGGCCCACTGGACGCCGCGCGGAAA CCGCGG CTAG-5' (SEQ ID NO:28).

The plasmid was then ligated. After ligation, the resulting plasmid (pcDNA3-LSI) was used to transform competent *E. coli* DH5α and the correct construct was confirmed by release of a 230 bp fragment following restriction enzyme digestion with NheI and NruI.

Plasmid pcDNA3-LSI was then digested with NgoMI, PvuI and BsmI. Following digestion, a 2.0 kb NgoMI-PvuI fragment was isolated. Plasmid pD12 (described above) was digested with PvuI and SphI to remove the SV40 enhancer and a 3.6 kb fragment was isolated. The following oligonucleotides, encoding the histone I3 transcription termination sequence were annealed and then ligated with the 2.0 kb NgoMI-PvuI fragment and 3.6 kb PvuI-SphI fragment:

5' primer:
5'-CCGGGCCTCTCAAAAAAGGGAAAAAAAGCATG-3' (SEQ ID NO:29); and
3' primer: 3'-CGGAGAGTTTTTTCCCTTTTTTTC-5' (SEQ ID NO:30).

The resulting plasmid pcTwD-LS1 was confirmed by the production of 3.3, 0.95, 0.82 and 0.63 kb fragments after digestion with NheI plus NciI and the production of 4.2, 1.0, 0.26 and 0.23 kb fragments after digestion with SphI plus BstEII.

Insertion of the gastrin transcription termination sequence to form plasmid 5 pD16 was accomplished by digesting pcTwD-LS1 with BssHII and NarI and isolating the 5.7 kb fragment and ligating with the following annealed oligonucleotides:

5' primer:
5'-CGCGCCGGCTTCGAATAGCCAGAGTAACCTTT TTTTTTAA TTTTATTTTATTTTATTTTTGAGATGGAGTTTGG-3' (SEQ ID NO:3 1); and
3' primer:
3'-GGCCGAAGCTTATCGGTCTCATTGGAAAAAAA AATTAAAAT AAAAT AAAATAAAAACTCTACCTCAAACCGC-5' (SEQ ID NO:32).

After ligation, the product was used to transform competent *E. coli* MC1061 and the correct construction was confirmed by the production of 4.8, 0.66 and 0.31 kb fragments after digestion with NgoMI plus SpeI and the production of 3.3, 1.0, 0.82 and 0.67 kb fragments following digestion with NgoMI plus NcoI.

Plasmid pD17 was derived from pD16 by the removal of the NheI site from the linearization polylinker. This was accomplished by digestion of pD16 with BstII and NheI and filling the protruding ends using Klenow polymerase. The reaction mixture was self-ligated and used to transform competent *E. coli* DH5α.

pD17 was digested with Asp718I and Bsp120I to remove a polylinker which was replaced by the 113 bp Asp718I/Bsp120I polylinker from pD13. After ligation, the resulting intermediate plasmid pD20 had the NheI site required for inserting heavy chain V genes. pD20 was distinguished from pD17 by linearization with NheI, and distinguished from pD13 by linearization with BssH II which cuts only once within the linearization site polylinkers of pD16, pD17 and pD20. Finally, DNA sequencing was used to confirm the polylinker in pD20.

A 2.9 kb EcoRI fragment was isolated from pGk.11 (Walls et al., *Nucl. Acid. Res.* 21:2921–2929 (1993)) and this was ligated into the plasmid pD13 (described above) previously digested with EcoRI. This construct (pD13-hCka) containing the human Cκ exon and flanking intron sequences was used to transform *E. coli* DH5α and the correct product was confirmed by restriction digestion. Digestion with EcoRI resulted in fragments of 5.7, 2.8 and 0.3 kb and digestion with SacI resulted in fragments of 7.1, 1.1 and 0.5 kb.

Construction of the light chain expression cassette was completed by removing the Cκ fragment along with the flanking polylinker sequences from pD13 and inserting it into pD16. Plasmid pD13-hCka was digested with Asp718I and Bsp120I to release the Cκ fragment and polylinker sequences. The same enzymes were used to linearize pD16 and the Cκ, containing fragment was ligated into pD16 to form pD16-hCka. Following transformation of DH5α *E. coli* and amplification, the correct construct was confirmed by the release of 2.9 kb fragment following digestion with Asp718I and Bsp120I and linearization following digestion with a restriction enzyme present in pD16, but not pD13. The nucleotide sequence was also confirmed by sequencing various regions of the construct.

A genomic DNA fragment encoding the human 65 2 gene was preassembled in pIC, and then transferred into pD20 as follows. Phage clone Phage SA (Ellison and Hood, *Proc. Natl. Acad Sci,* 79: 1984–1988 (1982)), containing the human γ2 gene was digested with HindIII and cloned into the HindIII site of pUC18 to form the vector pγ2. In pγ2, the 5' end of the γ2 gene is adjacent to the polylinker region. pG was derived from pSV2-gpt by digestion with Hind III and Bgl II, Klenow fill in, and religation. This served to remove a 121 bp Hind III-Bgl II fragment. pγ2 was then digested with BamH I and inserted into the BamH I site of pG to form pGγ2.2. pGγ2.2 contains a BglII site 3' of the coding region that would interfere with later cloning steps. To remove this restriction site, pGγ2.2 was first digested with Bgl II, the sticky ends filled in by Klenow DNA polymerase I, then the plasmid religated. The resulting intermediate plasmid, pGγ2.3 was screened for lack of digestibility with Bgl II.

For purposes of later cloning in variable region genes, it was important to provide a restriction site in the γ2 containing cassette. This is conveniently done by mutating the nucleotides encoding the first two amino acids of the CH1 exon to encode an Nhe I site (Coloma M. J. et al., *J. Immunological Methods* 152:89–104(1992)). Previously, an Nhe I to Bst E II fragment from the human γ4 gene was cloned. In this region, human γ2 and human γ4 genes encode identical amino acids. Thus, the γ4 containing vector (pIChγ4. 1) could serve as a source for the 5' end of the γ2 gene. This vector was obtained as follows: The 8.6 kb BamH I fragment from Phage 5D (Ellison, J. et al *DNA* 1:11–18 (1981)), containing the human γ4 gene, was subcloned into pUC, resulting in the plasmid pUChγ4. pUChγ4 served as the template for a PCR reaction involving the following primers: sense primer: 5'-ATCGAT GCTAGCACCAAGGGCCCA-3' (SEQ ID NO:33); and antisense primer: 5'-CTCGAGG GGTCACCACGCTGCTGA-3' (SEQ ID NO:34). The sense primer contained a Cla1 site for subcloning the PCR product into pIC20R (Marsh J. L., et al., *Gene* 32: 481–485 (1984)) adjacent to a synthetic Nhe1 site (underlined). Note that the bases for the Nhe1 site can encode the first two amino acids (Alanine and Serine) for the human γ1, γ2, γ3 or γ4 CH1 exon. The antisense primer has an Xho I site for subcloning into pIC20R, next to a BstE II site (underlined) which is in the CH1 exon of the human γ4 and γ2 gene. The PCR product formed was restricted with Cla I+Xho I then ligated into pIC20R which had been digested by the same enzymes, to generate the intermediate pIChγ4.1.

pGγ2.3 was digested with BamH I and HinD III and a 6.1 Kb fragment including the human γ2 gene locus was isolated from a 1.4% agarose gel for purification by the Qiaex™ gel extraction kit (Qiagen, Chatsworth, Calif.). The 2.9 Kb pIChγ4.1 plasmid was treated in a similar manner, and the two fragments were ligated together to form the intermediate vector pIChγ2. 1. To screen, an EcoR I digest yielded appropriate fragment sizes of 6.3 Kb and 2.6 Kb.

pIChγ2.1 contained a duplication of the 5' portion of the human γ2/γ4 CH1 exon. In order to remove the duplicated region, it was digested with BstE II giving fragment sizes of 4.0 Kb, 1.8 Kb, 1.6 Kb, 1.1 Kb, and 0.4 Kb. The 4.0 Kb fragment was isolated from a 1.4% agarose gel, while the 1.6 Kb fragment was separated and isolated away from the 1.8

Kb fragment in 4% NuSieve™ GTG (FMC Bioproducts, Rockland, Me.) agarose. Both fragments were purified by Qiagen gel extraction prior to ligating them together to prepare pIChγ2.2. In order to confirm the proper orientation of the two fragments the following primers were used to determine that the 3' portion of the human γ4 CH1 exon's BstE II sticky end had joined with the 5' end of the human γ2 CH1 exon (thus forming a contiguous human γ2 locus in pIC20R):

sense primer: 5'-AACAGCTATGACCATGATTAC-3' (SEQ ID NO:35); and antisense primer: 5'-CACCCAGCCTGTGCCTGCCTG-3' (SEQ ID NO:36).

The sense primer is homologous to sequence 5' of the pIC20R EcoR I site that is adjacent to the Cla I site. The antisense primer was chosen to be 500 bp downstream of the sense strand primer, and is homologous to sequence within the human γ2 CH1 to CH2 intron. Thus, visualization of a 500 bp PCR product in a 1.4% agarose gel confirmed that the hybrid human γ4–γ2 CH1 exon formed and was oriented in a contiguous manner to the remainder of the locus. pIChγ2.2 was digested with EcoR I to give the expected 2.6 Kb and 1.9 Kb fragments. The entire human γ2 CH1 exon was confirmed by DNA sequencing.

The 1.8 Kb Nhe I+HinD III fragment containing the human γ2 gene locus was removed from pIChγ2.2 for ligation into plasmid pD20 opened by Nhe I+HinD III. The resulting vector is the expression cassette pD20-hγ2a.

The variable region (V) genes for both chimeric and humanized antibodies were synthesized by a modification of the non template specific PCR protocol (Prodromou C., and Pearl L. H., *Protein Eng.* 5: 827–829 (1992)). The PCR products included DNA encoding both the signal peptide and variable region proper as well as flanking sequences to facilitate insertion into the vector as well as correct splicing (light chain only).

The following primers were used:

LH1, sense chimeric 77A3 VH outer primer (30 mer), 5'-CGATTGGAATTCTTG CGGCCGCTTGCTAGC-3' (SEQ ID NO:37);

LH2, sense chimeric 77A3 VH primer 1 (80 mer), 5'-CTTGCGGCCGCTTGCTA GCATGGATTGGGT-GTGGAACTTGCTATTCCTGATGGCAGCTGCCCAA AGTATCCAAGCACAGA-3' (SEQ ID NO:38);

LH3, anti-sense chimeric 77A3 VH primer 2 (80 mer), 5'-CTTGACTGTTTC TCCAGGCTTCTTCAGCTCAG-GTCCAGACTGCACCAACTGGATCTGTGC TTGGATACTTTGGGCAGCTG-3' (SEQ ID NO:39);

LH4, sense chimeric 77A3 VH primer 3 (80 mer), 5'-CTGAAGAAGCCT GGAGAAACAGTCAA-GATCTCCTGCAAGGCTTCTGGGTATACCTTCAC AAACTATGGAATGAACTGGGT-3' (SEQ ID NO:40);

LH5, anti-sense chimeric 77A3 VH primer 4 (80 mer), 5'-TCTTGGTGTTTAT CCAGCCCATCCACTT-TAAACCCTTTCCTGGAGCCTGCTTCACCCAGTT CATTCCATAGTTTGTGAAG-3' (SEQ ID NO:41);

LH6, sense chimeric 77A3 VH primer 5 (80 mer), 5'-AGTGGATGGGCT GGATAAACACCAAGAGTG-GAGAGCCAACATATGCTGAAGAGTTCAA GGGACGGTTTGCCTTCTCTTTG-3' (SEQ ID NO:42);

LH7, anti-sense chimeric 77A3 VH primer 6 (80 mer), 5'-TCCTCATTTTTGA GGTTCTTGATCTGCAAATTG-GCAGTGCTGGCAGAGGTTTCCAAAGAG AAGGCAAACCGTCCCTTGAA-3' (SEQ ID NO:43);

LH8, sense chimeric 77A3 VH primer 7 (80 mer), 5'-GCAGATCAAGAACC TCAAAAATGAGGACACG-GCTACATATTTCTGTGCAAGATGGGTACCT GGGACCTATGCCATGGACT-3' (SEQ ID NO:44);

LH9, anti-sense chimeric 77A3 VH primer 8 (80 mer), 5'-TGGGCCCTTGGTGC TAGCTGAGGAGACGGT-GACTGAGGTTCCTTGACCCCAGTAGTCCATG GCATAGGTCCCAGGTACCC-3' (SEQ ID NO:45);

LH10, anti-sense murine 77A3 VH outer primer (29 mer), 5'-GGGAAGACGGATG GGCCCTTGGTGCTAGC-3' (SEQ ID NO:46);

LH11, sense chimeric 77A3 VL outer primer (30mer), 5'-ATTTAAATTGAT ATCTCCTTAGGTCTCGAG-3' (SEQ ID NO:47);

LH12, sense chimeric 77A3 VL primer 1(79 mer), 5'-ATTTAAATTGATATCTCC TTAGGTCTCGAGAT-GAGTGTGCTCACTCAGGTCCTGGCGTTGCTGCT GCTGTGGCTTACAG-3' (SEQ ID NO:48);

LH13, anti-sense chimeric 77A3 VL primer 2 (78 mer), 5'-AGATGCAGATAGG GAGGCTGGAGACTGAGT-CATCTGGATGTCACATCTGGCACCTGTAAG CCACAGCAGCAGCAACGC-3' (SEQ ID NO:49);

LH14, sense chimeric 77A3 VL primer 3 (78 mer), 5'-GTCTCCAGCCTCCCTA TCTGCATCTGTGG-GAGAAACTGTCACCATCACATGTCGAG-CAAGTGG GAATATTCACAATTA-3' (SEQ ID NO:50);

LH15, anti-sense chimeric 77A3 VL primer 4 (78 mer), 5'-TATAGACCAG GAGCTGAGGAGATTTTCCCT-GTTTCTGCTGATACCATGCTAAATAATT GTGAATATTCCCACTTGCTC-3' (SEQ ID NO:51);

LH16, sense chimeric 77A3 VL primer 5 (78 mer), 5-AAATCTCCTCAGCT CCTGGTCTATAATG-CAAAAACCTTAGCAGATGGTGTGCCATCAAGGT TCAGTGGCAGTGGATCA-3' (SEQ ID NO:52);

LH17, anti-sense chimeric 77A3 VL primer 6 (78 mer); 5'-CTCCCAAAATCT TCAGGCTGCAGGCTGT-TGATCCTGAGAGAAAATTGTGTTCCTGATCC ACTGCCACTGAACCTTGAT-3' (SEQ ID NO:53);

LH18, sense chimeric 77A3 VL primer 7 (78 mer), 5'-GCCTGCAGCCTGAAGATTTTGGGAGTCATTACT GTCAACATTTTTG GACCACTCCGTGGACGTTCG GTGGAGGCACCA-3' (SEQ ID NO:54);

LH19, anti-sense chimeric 77A3 VL primer 8 (81 mer), 5'-TTCCAATCGATTGA CCGGTTATCTAGAGACTC-GAGACTTACGTTTGATTTCCAGCTTGGTGC CTCCACCGAACGTCCACGG-3' (SEQ ID NO:55);

LH20, anti-sense chimeric 77A3 VL outer primer (30mer), 5'-TCGATTGA CCGGTTATCTAGAGACTCGAGA-3' (SEQ ID NO:56);

LH21, anti-sense humanized 77A3 VL primer 2 (78 mer), 5'-AGATGCAGATA GGGAGGATGGAGACTGAGT-CATCTGGATGTCACATCTGGCACCTGTA AGCCACAGCAGCAGCAACGC-3' (SEQ ID NO:69)

LH22, sense humanized 77A3 VL primer 3 (78 mer), 5'-GTCTCCATCCTCC CTATCTGCATCTGTGG-GAGACAGAGTCACCATCACATGTCGAGCAAG TGGGAATATTCACAATTA -3' (SEQ ID NO:70)

LH23, sense humanized 77A3 VL primer 5 (78 mer), 5'-AAATCTCCTCAA CTCCTGGTCTATAATG-CAAAAACCTTAGCAAGTGGTGTGCCATCAAG GTTCAGTGGCAGTGGATCA -3' (SEQ ID NO:71)

LH24, anit-sense humanized 77A3 VL primer 6 (78 mer), 5'-CTCCCAAAATC TTCAGGCTGCAGGCTGCT-GATGGTGAGAGTAAAATCTGTTCCTGATC CACT-GCCACTGAACCTTGAT -3' (SEQ ID NO:72)

LH25, sense humanized 77A3 VH -1 primer 1(80 mer), 5'-CTTGCGGCCGCTTG CTAGCATGAGTGTGCT-CACTCAGGTCCTGGCGTTGCTGCTGCTGTGG CTTACAGGTGCCAGATGTC -3' (SEQ ID NO:57);

LH26, anti-sense humanized 77A3 VH -1 primer 2 (80 mer); 5'-GACTGAGGCT CCAGGCTTCTTCAGCTCA-

GATCCAGACTGCACCAACTGGATCTGACA TCTG-
GCACCTGTAAGCCACAGCA -3' (SEQ ID NO:58);

LH27, sense humanized 77A3 VH -1 primer 3 (80 mer),
5'-GAGCTGAAGAAGC CTGGAGCCTCAGTCAA-
GATCTCCTGCAAGGCTTCTGGGTATACCTTCA
CAAACTATGGAATGAACTG -3' (SEQ ID NO:59);

LH28, anti-sense humanized 77A3 VH -1 primer 4 (80 mer)
5'-TGGTGTTTATC CAGCCCATCCACTCTAAACCT-
TGTCCTGGAGCCTGTCGCACCCAGTTC ATTCCAT-
AGTTTGTGAAGGTA -3' (SEQ ID NO:60);

LH29, sense humanized 77A3 VH -1 primer 5 (80 mer),
5'-TAGAGTGGATGGG CTGGATAAACACCAA-
GAGTGGAGAGCCAACATATGCTGAAGAGTTCA
AGGGACGGTTTGTCTTCTCT -3' (SEQ ID NO:61);

LH30, anti-sense humanized 77A3 VH -1 primer 6(80 mer),
5'-TCAGCTTTGAGG CTGCTGATCTGCAAATAG-
GCAGTGCTGACAGAGGTGTCCAAAGAGAA
GACAAACCGTCCCTTGAACTC -3' (SEQ ID NO:62);

LH31, sense humanized 77A3 VH -1 primer 7 (80 mer),
5'-TTTGCAGATCAG CAGCCTCAAAGCTGAGGA-
CACGGCTGTGTATTTCTGTGCAAGATGGG TAC-
CTGGGACCTATGCCATGG -3' (SEQ ID NO:63);

LH32, anti-sense humanized 77A3 VH -1 primer 8 (80 mer),
5'-GCCCTTGGTG CTAGCTGAGGAGACGGTGAC-
CGTGGTTCCTTGACCCCAGTAGTCCAT GGCAT-
AGGTCCCAGGTACCCATC -3' (SEQ ID NO:64);

LH33, anti-sense humanized 77A3 VH -2 primer 2 (80 mer),
5'-TGCTGTGGCT TACAGGTGCCAGATGTCAGATC-
CAGTTGGTGCAGTCTGGAGCTGAGG TGAA-
GAAGCCTGGAGCCTCAGTC -3' (SEQ ID NO:65);

LH34, sense humanized 77A3 VH -2 primer 5 (80 mer),
5'-TAGAGTGGATGGGC TGGATAAACACCAA-
GAGTGGAGAGCCAACATATGCTGAAGAGTTCAA
GGGACGGTTTACCTTCACC -3' (SEQ ID NO:66);

LH35, anti-sense humanized 77A3 VH -2 primer 6 (80 mer),
5'-TCAGATCTGAG GCTCCTGATCTCCAAATAG-
GCAGTGCTCGTAGAGGTGTCCAAGGTGA AGG-
TAAACCGTCCCTTGAACTC -3' (SEQ ID NO:67); and LH36, sense humanized 77A3 VH -2 primer 7 (80 mer,
5'-TTTGGAGATC AGGAGCCTCAGATCTGACGA-
CACGGCTGTGTATTTCTGTGCAAGATG GGTAC-
CTGGGACCTATGCCATGG -3' (SEQ ID NO:68).

Table 3 summarizes how the above primers were used in the non-template PCR protocol.

TABLE 3

Use of primers in non-template PCR

| | | Heavy chains | | | Light chains | |
|---|---|---|---|---|---|---|
| | | chimeric | humanized-1 | humanized-2 | chimeric | humanized |
| outer primer (sense) | | LH1 (SEQ ID NO: 37) | LH1 (SEQ ID NO: 37) | LH1 (SEQ ID NO: 37) | LH11 (SEQ ID NO: 47) | LH11 (SEQ ID NO: 47) |
| V1 (sense) | | LH2 (SEQ ID NO: 38) | LH25 (SEQ ID NO: 57) | LH25 (SEQ ID NO: 57) | LH12 (SEQ ID NO: 48) | LH12 (SEQ ID NO: 48) |
| V2 (antisense) | | LH3 (SEQ ID NO: 39) | LH26 (SEQ ID NO: 58) | LH33 (SEQ ID NO: 65) | LH13 (SEQ ID NO: 49) | LH21 (SEQ ID NO: 69) |
| V3 (sense) | | LH4 (SEQ ID NO: 40) | LH27 (SEQ ID NO: 59) | LH27 (SEQ ID NO: 59) | LH14 (SEQ ID NO: 50) | LH22 (SEQ ID NO: 70) |
| V4 (antisense) | | LH5 (SEQ ID NO: 41) | LH28 (SEQ ID NO: 60) | LH28 (SEQ ID NO: 60) | LH15 (SEQ ID NO: 51) | LH15 (SEQ ID NO: 51) |
| V5 (sense) | | LH6 (SEQ ID NO: 42) | LH29 (SEQ ID NO: 61) | LH34 (SEQ ID NO: 66) | LH16 (SEQ ID NO: 52) | LH23 (SEQ ID NO: 71) |
| V6 (antisense) | | LH7 (SEQ ID NO: 43) | LH30 (SEQ ID NO: 62) | LH35 (SEQ ID NO: 67) | LH17 (SEQ ID NO: 53) | LH24 (SEQ ID NO: 72) |
| V7 (sense) | | LH8 (SEQ ID NO: 44) | LH31 (SEQ ID NO: 63) | LH36 (SEQ ID NO: 68) | LH18 (SEQ ID NO: 54) | LH18 (SEQ ID NO: 54) |
| V8 (antisense) | | LH9 (SEQ ID NO: 45) | LH32 (SEQ ID NO: 64) | LH32 (SEQ ID NO: 64) | LH19 (SEQ ID NO: 55) | LH19 (SEQ ID NO: 55) |
| outer primer (antisense) | | LH10 (SEQ ID NO: 46) | LH10 (SEQ ID NO: 46) | LH10 (SEQ ID NO: 46) | LH20 (SEQ ID NO: 56) | LH20 (SEQ ID NO: 56) |

Briefly, 8 adjacent oligonucleotides which represent a synthetic light or heavy chain V gene are synthesized (V1–V8 in Table 3). Four sense strand oligonucleotides alternate with 4 overlapping antisense strand oligonucleotides of 78–81 nt in length. These PCR primers overlap each other by 24–27 nt. Note that for oligonucleotide primers V1 and V8 (Table 3), their 5' end is designed to overlap with 15 -30 nt of the vector sequence, while their 3' end overlaps 48–65 nt of the signal peptide (V1) or the V gene sequence (V8). The 8 oligonucleotide primers are all included in the same first round PCR. Reaction conditions for this 1st round PCR were 0.125 picomoles of each primer, 10 μl of 10× Pfu buffer (Stratagene Inc., San Diego, Calif.), 10 nanomoles dNTP's (Boehringer Mannheim, Indianapolis, Ind.), 10% dimethylsulfoxide (DMSO), and 2.5 units cloned Pfu DNA polymerase I (Stratagene Inc., San Diego, Calif.) in a 100 μl reaction volume. Reactants were first denatured at 95° C. for 5 min, annealed at 45° C. for 5 min, and extended at 72° C. for 1 min, followed by 25 cycles of denaturation at 94° C. for 30 sec, annealing at 55° C. for 30 sec, and extension at 72° C. for 30 sec. The 25 cycles were followed by a final extension at 72° C. for 7 min in a Perkin-Elmer DNA Thermal Cycler (Norwalk, Conn.).

The amplified PCR product was electrophoresed through a 1.4% agarose gel and the smear of DNA ruing between approximately 350 bp–500 bp was cut out prior to purification by the Qiaex™ II gel extraction kit (Qiagen, Chatsworth, Calif.). This purified non template specific PCR product served as the template for a 2nd round PCR To complete the 2nd round PCR, two additional outer primers are utilized. These outer primers are homologous to 29–30 nt of the vector sequence that is either 5' (sense primer) or 3' (antisense primer) of the linearized cloning site within the mammalian expression cassette vector. This allowed for the amplified PCR product to be subcloned into the vector by bacterial homologous recombination (Jones, D. H. and Howard, B. H., *BioTechniques* 10: 62–66 (1991)).

Thus, the reaction conditions for the 2nd round PCR were 0.125 picomoles each of outer sense and antisense primers, 10 μl of 10× Pfu buffer, 10 nanomoles dNTP's, 10% DMSO, 2.5 units Pfu DNA polymerase I, and approximately 100 ng of 1st round PCR template DNA. The reactants underwent the same thermocycle program described above. Subsequently, the amplicand from this reaction was removed from a 1.4% agarose gel and purified with the Qiagen™ II gel extraction kit.

200 ng–1000 ng of PCR product was mixed with an equal weight of linearized vector, and this mixture was used to transform 200 ml of competent E. coli DH5α cells (GIBCO BRL/Life Technologies, Gaithersburg, Md.).

Transformed cells were selected by 100 μml ampicillin in LB agarose. Typically, pD 16-hCka digested with Xho I was used for subcloning light chain V genes. pD20-hg2a digested with Nhe I served as the vehicle for heavy chain V gene constructs.

In order to confirm that the V gene of interest had been inserted into the expression vector, two screens were performed. The primary screen was by PCR, while the secondary screen was by restriction digest. Each individual colony of bacteria was picked into 5 ml of T broth (GIBCO BRL/Life Technologies, Gaithersburg, Md.) containing 100 μg/ml ampicillin and grown 8–16 hr at 37° C. with shaking. The conditions for the PCR screen were 0.125 picomoles of both outer primers (Table 3), 2 ml 10× $Mg^{+2}$ buffer (Boehringer Mannheim, Indianapolis, Ind.), 10 nanomoles dNTP' (Boehringer Mannheim, Indianapolis, Ind.) 1 unit Taq DNA polymerase I (Boehringer Mannheim, Indianapolis, Ind.), and 1 μl of the liquid culture growth (which served as the source of DNA template since the cells lysed at high temperature) in a 20 μl volume. Reactants first underwent denaturation at 94° C. for 5 min. followed by 25 cycles of denaturation at 94° C. for 25 sec, annealing at 45° C. for 25 sec, and extension at 72° C. for 12 sec. The cycles were followed by a final extension at 72° C. for 7 min. Positives were determined by size comparison relative to a DNA standard marker after electrophoresis through a 1.4% agarose gel.

For the secondary screen, midi DNA preparations (Qiagen, Chatsworth, Calif.) were made from bacterial pellets and a portion was digested with either Xho I (VL genes) or Nhe I (VH genes). Again, after electrophoresis through a 1.4% agarose gel, size comparison of the fragment released due to enzyme digestion served to identify potentially positive clones.

The above procedures were used to confirm the presence of a potentially correct insert. However, they were not specific enough to detect small errors in the sequence (insertions, deletions and substitutions). To determine which clones contained DNA encoding complete Ig genes, each potentially positive heavy chain clone was cotransfected into COS cells with each potentially positive light chain clone. Culture supernatants were screened by ELISA for the presence of human IgG, and then for the presence of IgG binding to α2-antiplasmin (see below).

DNA for COS transfections was derived from midi DNA preparations described above. COS tranfections were performed in 60 mm dishes. Complete details of the DEAE-dextran technique employed have been described (Linsley P. S. et al., J. Exp. Med 173: 721–730 (1991)). Typically, 1.5 μg–6 μg of whole antibody is derived from small scale COS transfections As a final confirmation, the V region inserts from the above clones were sequenced by the dideoxy nucleotide procedure.

B. Production of Humanized and Chimeric Antibodies

Once heavy and light chain vectors encoding each of the desired antibodies were qualified, sufficient quantities of chimeric and humanized antibody for testing in functional assays were needed. This was first done as a scale-up of the COS transfections using the selected vectors. Finally, stable cell lines were prepared by high copy number electroporation. The electroporation protocol of Barsoum (Barsoum, DNA and Cell Biology 9:293–300 (1990)) was followed with the exception that 100 μg each of the heavy and light chain vector were used (following restriction with BssHII) and the electroporation was performed in PFCHO media (PX-CELL PFCHO media, JRH Biosciences, Lenexa, Kansas).

Transfected cells were selected in media containing either 20 nM or 100 nM methotrexate (MTX). Culture supernatants were assayed for the presence of whole antibody using the non-specific IgG ELISA Cells from master wells containing the most antibody in the supernatant were expanded into larger volumes. In some cases, the methotrexate concentration was also increased in order to amplify the vector in the cell lines. The vector pairs in Table 4 were electroporated into DG44 CHO cells.

TABLE 4

Vector pairs for production of antibody

| Product | Heavy Chain Vector | Light Chain Vector |
| --- | --- | --- |
| c77A3 (chimeric 77A3) | pD20-cR1.H1 | pD16-cR1.L1 |
| h77A3-1 (humanized 77A3) | pD20-hR1.H1 | pD16-hR1.L1 |
| h77A3-2 (humanized 77A3) | pD20-hR2.H1 | pD16-hR1.L1 |
| h77A3-3 (humanized 77A3) | pD20-hR3.H1 | pD16-hR1.L1 |

C. Purification of Humanized and Chimeric Antibodies

The purification of the antibody was first performed using protein-A affinity chromatography. A Pharmacia column, sized so that 5 mg of antibody to be loaded per 1 ml of resin, was packed with Perseptive Biosystems Poros 50 A protein-A resin. The column was then sanitized according to the methods recommended by the resin supplier. The column was equilibrated with pyrogen free 10 mM sodium phosphate, 150 mM sodium chloride pH 7.0 (PBS). The cell culture supernatant was adjusted to pH of 7.0–7.5 and loaded on the column at a flow rate equal to 2–3 column volume/min (CV/min). The column was then washed with 15 CV pyrogen free PBS or until a stable base line has been achieved. The antibody was eluted with 20 mM glycine/HCl pH 3.0 elution buffer. The eluted peak was collected in a pyrogen free vessel that contained 1/20 CV of 1 M Tris base solution. The pH of the eluted antibody solution was adjusted to pH 8.0 with 1M Tris base immediately. The column was then cleaned with 5 CV 12 MM HCl solution. The column was stored in 20% ethanol/water at 4.0° C.

The antibody was next purified using anion exchange chromatography. A Pharmacia column, sized so that 5–10 mg of antibody to be loaded per 1 ml of resin, was packed with Perseptive Biosystems Poros HQ 50 anion exchange resin. The column was then sanitized according to the methods recommended by the resin supplier. The column was equilibrated with pyrogen free 50 mM Tris/HCl, 50 mM NaCl, pH 8.0. The protein-A purified antibody adjusted to pH of 8.0 was loaded on the column with flow rate equal to 1 CV/min. The column was then washed with 5 CV pyrogen free 50 mM Tris/HCl, 1M NaCl pH 8.0. The antibody does not bind to this column under the running conditions and was present in the flowthrough fraction. The column was stored in 20% ethanol/water at 4.0° C. The antibody was then concentrated and diafiltered against PBS using a 30K cut off membrane.

D. Non-specific IgG ELISA to Detect Presence of Antibody

This ELISA detects whole antibody (containing both heavy and light chain) and relies on a capture antibody specific for human IgG Fc region and a conjugate specific for human kappa chains. In this assay, Immunlon II flat bottom plates (Dynatech) were coated with goat anti-human IgG (Fc specific, adsorbed on mouse IgG) (Caltag, Inc. catalog #H10000) at 0.5 μg/ml in carb/bicarb buffer pH 9.6 and then blocked with PTB (PBS containing 0.05% Tween 20 and 1.0% BSA). Sample was added (either undiluted or diluted in PTB or Genetic Systems specimen diluent), the plates were incubated o/n at 4° C. or for a few hours at room temperature. After washing, conjugate (goat anti-human kappa conjugated with horseradish peroxidase from Southern Biotech) was added at 1:10000 in PTB. After approximately 1 hour incubation at room temperature, plates were washed and 100 μl chromagen/substrate was added (Genetic Systems chromagen diluted 1:100 into Genetic Systems substrate). After sufficient color development (usually 5 to 15 minutes) 100 μl 1 N $H_2SO_4$ was added to stop the reaction. Optical densities were determined using a Biotek plate reader set at 450 and 630 nm wavelengths.

In the occasional case that none of the samples from small COS transfections showed the presence of whole antibody, similar ELISAs were performed to determine whether any light chain was being secreted. In this case, the plates were coated with a goat anti-human kappa chain at 1 μg/ml. The rest of the assay was done exactly as above.

The assay was used for three purposes. First, to screen small COS transfections that were set up to qualify various heavy and light chain vectors. In this case, the presence or absence of a signal was sufficient and it was not necessary to quantify the amount of antibody present. Second, to determine which of many master wells from CHO transfections were producing the most antibody. In this case, culture supernatants were diluted so that relative signals could be compared and the master wells containing the most antibody could be distinguished and thus selected for cloning and expansion. Thirdly, to determine amounts of antibody, either in culture supernatants or following purification. In this case, a standard consisting of either a chimeric or human IgG1 or a human myeloma IgG2 were used. Both standard and sample were serially diluted (2×) across a plate and sample concentration relative to standard was determined by comparing position of the curves. The concentrations thus determined were used for following antibody production during the cloning and amplification process and for determining specific activity in the antigen binding ELISA and any of the functional assays.

E. ELISAs to Show That Antibody is Capable of Binding to Antigen

This ELISA relies on an antigen capture and a human kappa chain specific conjugate. It was used for two purposes. Initially, to qualify a vector, supernatants from COS transfections were screened for the ability of antibody to bind to antigen. Vectors passing this test were then submitted to DNA sequencing. Secondly, to determine relative antigen binding ability of the various chimeric and humanized antibodies. This ELISA is very similar to the non-specific IgG ELISA described above except that the plates were coated with α2-antiplasmin (obtained from American Diagnostica) at 1 μg/ml in PBS.

To determine relative antigen binding ability of various antibodies, scatter plots were used with log antibody concentration along the X axis and optical density along the Y axis. Antigen concentration was determined either from the non-specific ELISA or based on optical density of purified preparations. All three forms of humanized antibody (h77A3-1, -2, and -3) show antigen binding similar to that of the chimeric antibody. Comparisons were not made with the murine antibody (m77A3) because the m77A3 cannot be detected in the assay as described (the antibody-conjugate used in the second step recognizes only human constant regions).

F. Functional Assays

Two functional assays were performed. The first, known as the "plasmin assay with chromogenic substrate" is based on the ability of plasmin to convert Spectrozyme PL, H-D-Nle-HHT-Lys-pNA.2AcOH into pNA, which absorbs light at 405 nm. If unblocked α2-antiplasmin is present, little or no conversion occurs. Active antibody is capable of blocking the inhibitory activity of α2-antiplasmin. The second assay, the clot lysis assay, is a measure of the ability of antibody along with urokinase to lyse preformed clots.

The plasmin assay with chromogenic substrate is designed based on the action of plasmin on its chromogenic substrate according to the reaction:

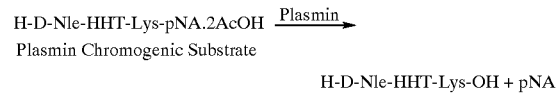

H-D-Nle-HHT-Lys-pNA.2AcOH $\xrightarrow{\text{Plasmin}}$
Plasmin Chromogenic Substrate H-D-Nle-HHT-Lys-OH + pNA The generation of pNA was monitored by the increase in absorption at 405 nm using a SpectraMax 250 spectrophotometer. The addition of α2-antiplasmin inhibits the plasmin activity and no increase in absorption at 405 nm will be observed. Premixing of α2-antiplasmin with functional antibody blocks the ability of α2-antiplasmin to inhibit the plasmin activity. Plasmin activity was measured as the initial rate of color development.

Assays are performed in 96 well microtiter plates. The chromogenic substrate Spectrozyme PL, H-D-Nle-HHT-Lys-pNA.2AcOH, human plasmin, and human α2-antiplasmin were purchased from American Diagnostica. Stock and working solutions are prepared as follows: Spectrozyme PL stock solution—10 mM in $H_2O$; Spectrozyme PL working solution—1:12.5 dilution of stock solution in $H_2O$; human plasmin stock solution—0.2 mg/ml in 50% glycerol, 50% 2 mM HCl; human plasmin working solution—1:12.5 dilution of stock solution in 0.11 mM HCl, which must be prepared immediately before use; human α2-antiplasmin stock solution—0.2 mg/ml in PBS; and human α2-antiplasmin working solution—1:15 dilution of stock solution in PBS. Stock solutions were stored at −70 and should not be refrozen after thawing.

Reagents are added in the following order, with mixing after each addition: 80 ul antibody or PBS, 40 ul α2-antiplasmin working solution, 40 ul plasmin working solution, and 40 ul Spectrazyme PL working solution. R is the rate of color development. Rp, which represents maximum plasmin activity, is determined in wells lacking both antibody and α2-antiplasmin. Ro, which represents minimal plasmin activity, is determined in wells lacking antibody. Rs is the rate of color development in the sample. Antibody activity is calculated as (Rs−Ro)/(Rp−Ro)*100. Values should range between 0% and 100%. Antibody activity was plotted vs. amount antibody (on a log scale). Curves generated by test antibody and standard (usually murine 77A3) were compared.

Figure 20:
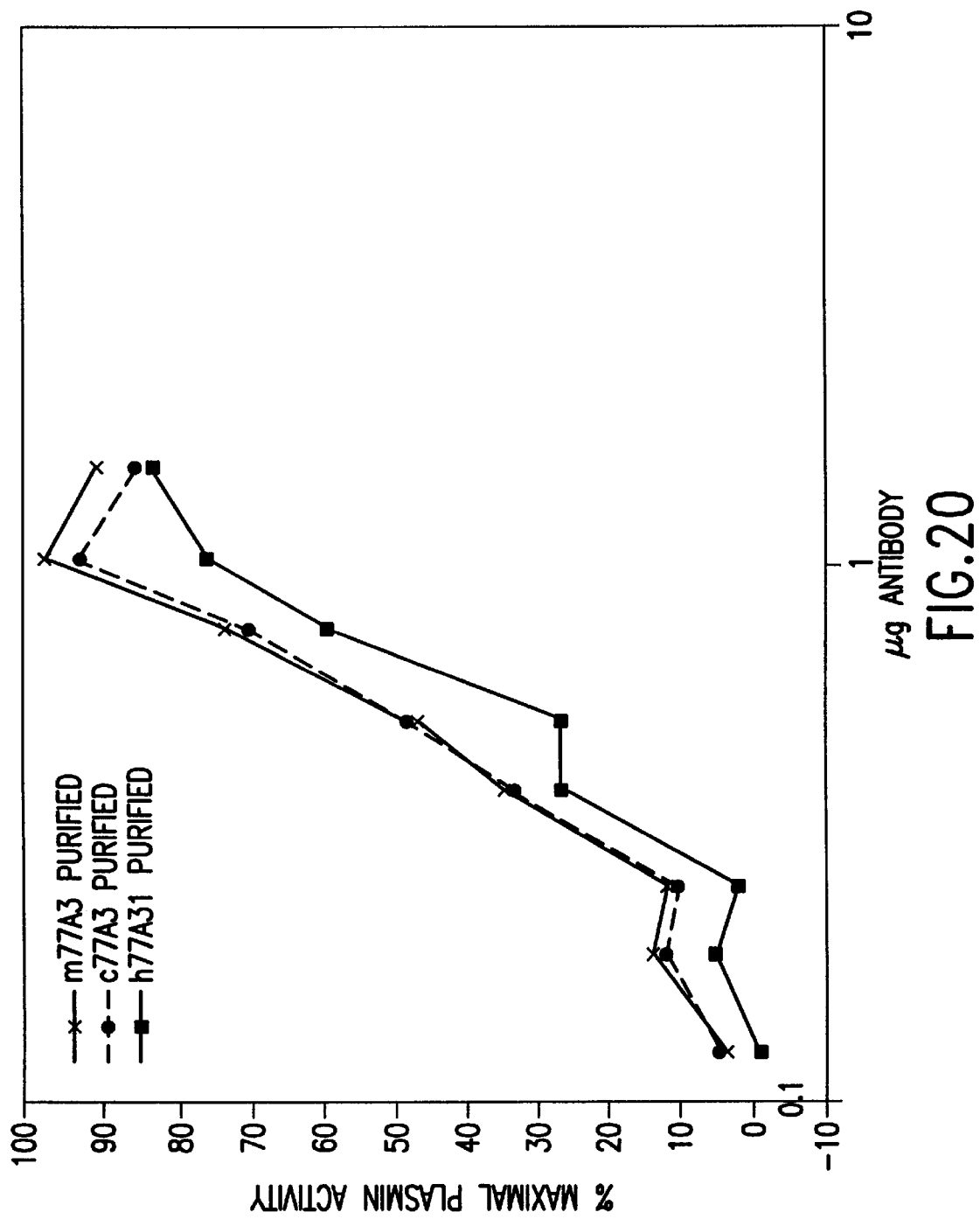
FIG. 20. Results of murine 77A3 (X), chimeric 77A3 (●) and humanized 77A3-1 (■) in the plasmin assay with chromogenic substrate are shown.

The data for murine 77A3, c77A3, and h77A3-1 are shown in FIG. 20. The curves for murine and chimeric 77A3 were superimposable. The curve for h77A3-2 indicates a potential small loss in activity (20–30%).

The clot lysis assays were performed as follows. Test clots were formed in 96-well Corning #25805 microtiter plates by mixing 25 uL 16 mM $CaCl_2$, 50 uL of pooled human plasma, and 25 uL of 4 NIH unit/ml of human alpha-thrombin (Sigma) in 30 mM Hepes buffer, pH 7.40. Plates were incubated overnight at room temperature to allow clots to achieve maximum clot turbidities. Clot lysis was initiated by adding 10 uL of antibody to give 5 or 10 ug/well and 100 uL of urokinase to give 1, 3 or 5 units of urokinase/well (Abbott Labs) at pH 7.40. Plates were mixed on a table top microplate vortexer for 30 sec before the initial reading at 405 nm to get values corresponding to 0% lysis. Plates were sealed with Corning sealing tape #430454 and incubated at 37° C. During the course of 24 hrs, the decrease of turbidity was measured at 405 nm to quantify the progress of clot lysis.

The results of a clot lysis experiment of humanized 77A3-1 indicate that h77A3-1 enhances clot lysis dramatically in comparison to buffer controls in each 5 of the conditions tested. There was significant separation between the humanized and murine 77A3 in clots containing 5 ug antibody in the presence of 1 or 3 units of urokinase indicating that humanized 77A3 was somewhat less active than murine 77A3, even though the lysis profiles were similar at the remaining four conditions tested. It should be noted that murine RWR, a monoclonal antibody with a 10-fold lower affinity than murine 77A3, causes no lysis at 10 ug per clot in the presence of 1 unit of urokinase and would give a lysis profile like buffer control.

EXAMPLE 5

Preparation and Characterization of Single Chain Fv Fragments

A. Design and Expression of sFv Form of 77A3

The sFv fragment of an antibody is most commonly obtained by the tandem expression of the variable region of the antibody heavy chain along with the variable region of the antibody light chain spaced by a linker of 15–20 amino acids. sFv fragments are expected to have superior clot penetration to parent antibodies. Two constructs, p53-6 and p52-12, were prepared using murine variable regions with a VH-(linker)-VL polarity using YPRSIYIRRRBPSPSLTT (SEQ ID NO:73) as linker I for sFv77A3-1 and GGSGSGGSGSGGSGS (SEQ ID NO:74) as linker 2 for sFv77A3-2. Both constructs were cloned into the pET-22b vector from Novagen and transformed into the BL21 (DE3) strain of *E. coli* grown in minimal M9 media. Though the majority of the His-tagged product was found in inclusion bodies, supernatants of cell lysate contained sufficient quantities of soluble sFv fragments for nickel-column purification.

sFv77A3-2 present in fractions 7–11 collected from a nickel-column gave a single Coomasie staining band with a MW about 30,000 agreeing well with the calculated MW of 29,986. A similar but more weakly staining gel was obtained for sFv77A3-1.

B. Activity of sFv77A3-1 and sFv77A3-2

Preparations of both sFv77A3-1 and sFv77A3-2 were tested for alpha2-antiplasmin binding activity in a competition binding assay. Microplate wells coated with 77A3 were treated with mixtures of biotinylated-human alpha2-antiplasmin and either sFv77A3-1 or sFv77A3-2 along with positive control 77A3 and negative control, mAb-59D8. Increasing quantities of 77A3 prevented binding of biotinylated-human alpha2-antiplasmin whereas negative control 59D8 had little effect as an competitive inhibitor. With concentrations of test samples estimated by intensity of Coomasie stained bands, both sFv77A3-1 and sFv77A3-2 completely inhibited the binding of biotinylated-human α2-antiplasmin with a profile of inhibition nearly superimposible to the parental 77A3 reference.

Idiotypic markers present on 77A3 were probed with a sandwich ELISA using a biotinylated polyclonal reagent rendered specific by multiple immunoadsorbtion steps through columns bearing immunoglobulins from man, mouse, baboon and cynomologous monkey (P Stenzel-Johnson & D Yelton, Seattle). Microplate wells were coated with 77A3 and 59D8 as controls along with sFv77A3-1 and sFv77A3-2. It is evident that 77A3 control and both sFv fragments bear idiotypic markers at each dose tested indicating that the sFv fragments "look" like the parental 77A3.

It will be clear that the invention may be practiced otherwise than as particularly described in the foregoing description and examples.

Numerous modifications and variations of the present invention are possible in light of the above teachings and, therefore, are within the scope of the appended claims.

The disclosure of all references, patent application, and patents referred to herein are hereby incorporated by reference.

What is claimed is:

1. An antibody which does not compete with the antibody RWR and binds to and inhibits both (1) human and nonhuman circulating α2-antiplasmins and (2) human and nonhuman fibrin crosslinked α2-antiplasmin; wherein said antibody augments clot lysis by fibrin-selective and nonselective plasminogen activators; and wherein said antibody comprises a human IgG constant region and a murine variable region.

2. The antibody of claim 1, wherein said antibody is c77A3.

3. An antibody which does not compete with the antibody RWR and binds to and inhibits both (1) human and nonhuman circulating α2-antiplasmins and (2) human and nonhuman fibrin crosslinked α2-antiplasmin; wherein said antibody augments clot lysis by fibrin-selective and nonselective plasminogen activators; and wherein said antibody comprises a human framework and at least one murine *Complementarity Determining Region* (CDR) region in the light chain of said antibody selected from the group consisting of:

(a) a CDR1 region comprising amino acids 26 to 32 of SEQ ID NO:17:

(b) a CDR2 region comprising amino acids 50 to 52 of SEQ ID NO:17; and (c) a CDR3 region comprising amino acids 91 to 96 of SEQ ID NO:17.

4. The antibody of claim 3, wherein said antibody comprises (a).

5. The antibody of claim 3, wherein said antibody comprises (b).

6. The antibody of claim 3, wherein said antibody comprises (c).

7. The antibody of claim 3, which is h77A3-1.

8. The antibody of claim 3, which is h77A3-2.

* * * * *